US012790645B2

(12) United States Patent
Ju et al.

(10) Patent No.: US 12,790,645 B2
(45) Date of Patent: Nov. 10, 2026

(54) AND SYNTHESIS OF CLEAVABLE FLUORESCENT NUCLEOTIDES AS REVERSIBLE TERMINATORS FOR DNA SEQUENCING BY SYNTHESIS

(71) Applicant: The Trustees of Columbia University in the City of New York, New York, NY (US)

(72) Inventors: Jingyue Ju, Englewood Cliffs, NJ (US); Huanyan Cao, Changzhou City (CN); Zengmin Li, Flushing, NY (US); Qinglin Meng, Foster City, CA (US); Jia Guo, Chandler, AZ (US); Shenglong Zhang, Fort Lee, NJ (US); Lin Yu, New York, NY (US)

(73) Assignee: THE TRUSTEES OF COLUMBIA UNIVERSITY IN THE OF NEW YORK, New York, NY (US)

( * ) Notice: Subject to any disclaimer, the term of this patent is extended or adjusted under 35 U.S.C. 154(b) by 0 days.

(21) Appl. No.: 19/288,628

(22) Filed: Aug. 1, 2025

(65) Prior Publication Data

US 2026/0209840 A1 Jul. 23, 2026

Related U.S. Application Data

(63) Continuation of application No. 19/001,296, filed on Dec. 24, 2024, which is a continuation of application (Continued)

(51) Int. Cl.

*C12Q 1/68* (2018.01)
*C07H 19/06* (2006.01)

(Continued)

(52) U.S. Cl.

CPC .......... *C12Q 1/6869* (2013.01); *C07H 19/06* (2013.01); *C07H 19/10* (2013.01); *C07H 19/14* (2013.01); *C07H 19/16* (2013.01); *C07H 19/20* (2013.01); *C12Q 2525/301* (2013.01); *C12Q 2537/157* (2013.01)

(58) Field of Classification Search

CPC ................ C12Q 1/6869; C12Q 1/6823; C12Q 2525/301; C12Q 2537/157; C07H 19/04; C07H 19/06; C07H 19/10; C07H 19/14; C07H 19/16; C07H 19/20

See application file for complete search history.

(56) References Cited

U.S. PATENT DOCUMENTS 7,883,869 B2 * 2/2011 Ju .................... C12Q 1/6869 536/26.6
8,298,792 B2 * 10/2012 Ju .................... C12Q 1/6869 536/26.6

(Continued)

OTHER PUBLICATIONS

First Information Disclosure Statement Substitute Form PTO-1449 submitted Dec. 23, 2021 and initialed by Examiner on Jan. 5, 2024 in connection with U.S. Appl. No. 17/560,928.

(Continued)

*Primary Examiner* — Jezia Riley
(74) *Attorney, Agent, or Firm* — Gary J. Gershik

(57) ABSTRACT

This invention provides novel azido linkers for deoxynucleotide analogues having a detectable marker attached thereto.

6 Claims, 46 Drawing Sheets

Specification includes a Sequence Listing.

Related U.S. Application Data

No. 17/560,928, filed on Dec. 23, 2021, now Pat. No. 12,180,544, which is a continuation of application No. 16/208,379, filed on Dec. 3, 2018, now Pat. No. 11,208,691, which is a continuation of application No. 15/596,379, filed on May 16, 2017, now Pat. No. 10,144,961, which is a continuation of application No. 14/859,853, filed on Sep. 21, 2015, now Pat. No. 9,670,539, which is a continuation of application No. 13/951,269, filed on Jul. 25, 2013, now Pat. No. 9,175,342, which is a continuation of application No. 12/734,227, filed as application No. PCT/US2008/011891 on Oct. 17, 2008, now abandoned.

(60) Provisional application No. 60/999,576, filed on Oct. 19, 2007.

(51) Int. Cl.

| | |
|---|---|
| ***C07H 19/10*** | (2006.01) |
| ***C07H 19/14*** | (2006.01) |
| ***C07H 19/16*** | (2006.01) |
| ***C07H 19/20*** | (2006.01) |
| ***C12Q 1/6869*** | (2018.01) |

(56) References Cited

U.S. PATENT DOCUMENTS

| | | | | |
|---|---|---|---|---|
| 11,098,353 | B2 * | 8/2021 | Ju | C12Q 1/6869 |
| 11,939,631 | B2 * | 3/2024 | Ju | C12Q 1/6869 |
| 12,559,797 | B2 * | 2/2026 | Ju | C12Q 1/6869 |

OTHER PUBLICATIONS

Second Information Disclosure Statement Substitute Form PTO-1449 submitted May 20, 2024 and initialed by Examiner on May 30, 2024 in connection with U.S. Appl. No. 17/560,928.

* cited by examiner

Fig. 2
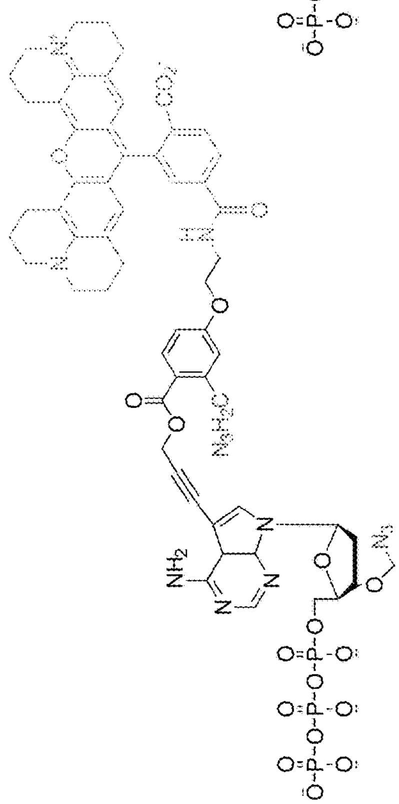
3'-O-Azido-dATP-Azido-ROX
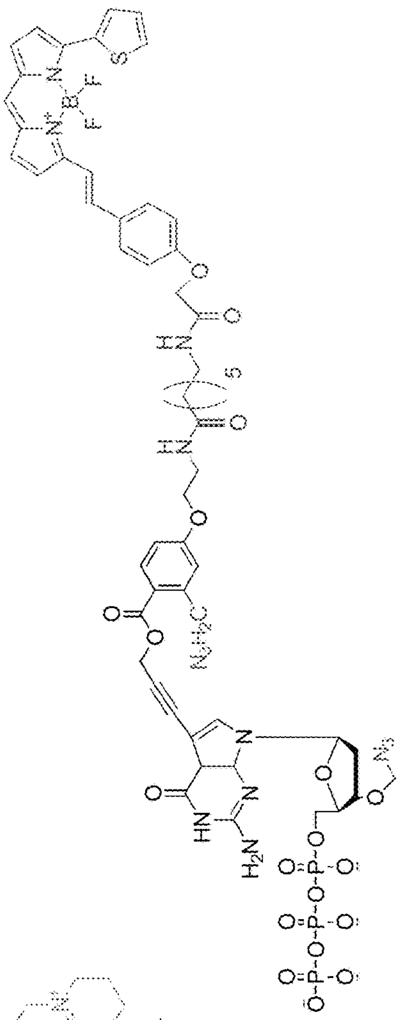
3'-O-Azido-dGTP-Azido-Bodipy650
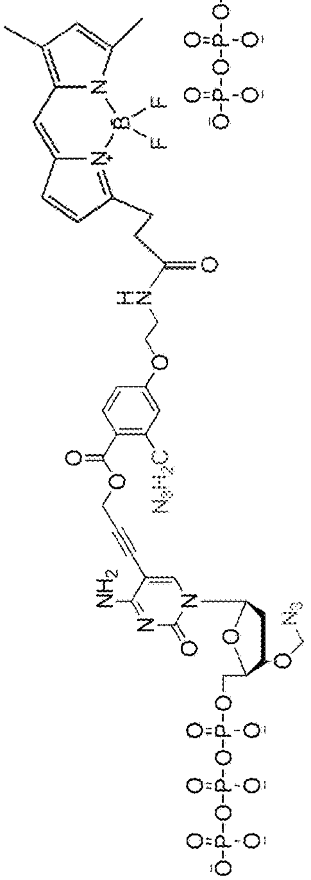
3'-O-Azido-dCTP-Azido-BodipyFl
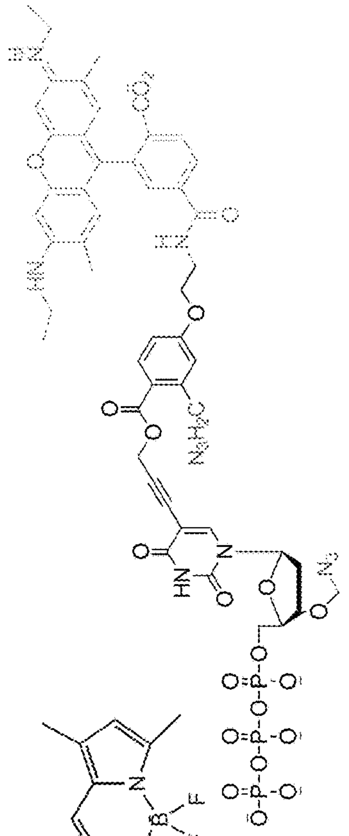
3'-O-Azido-dUTP-Azido-R6G Fig. 4
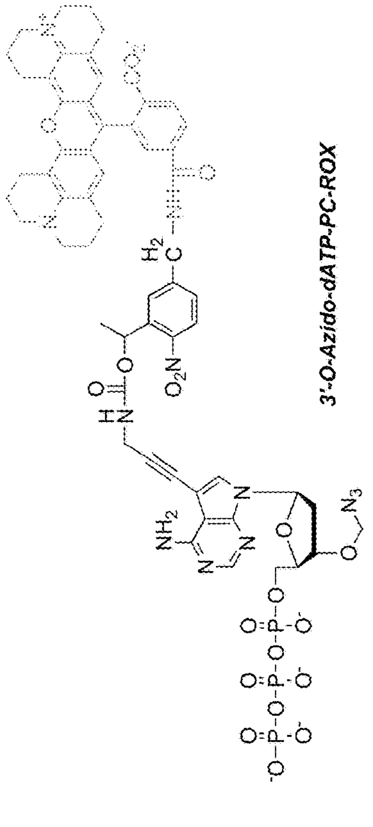
3'-O-Azido-dATP-PC-ROX
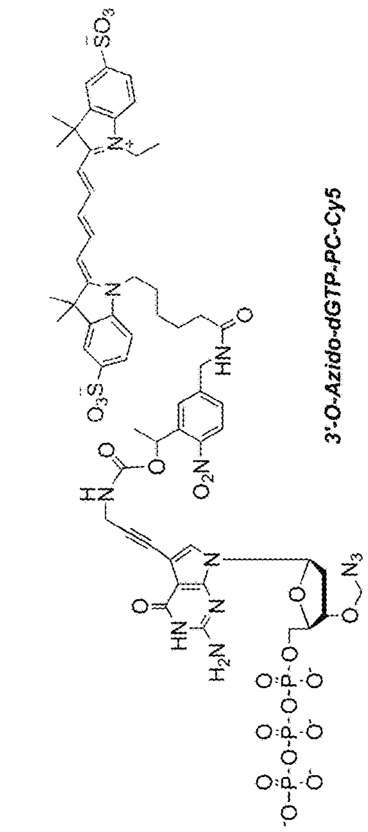
3'-O-Azido-dGTP-PC-Cy5
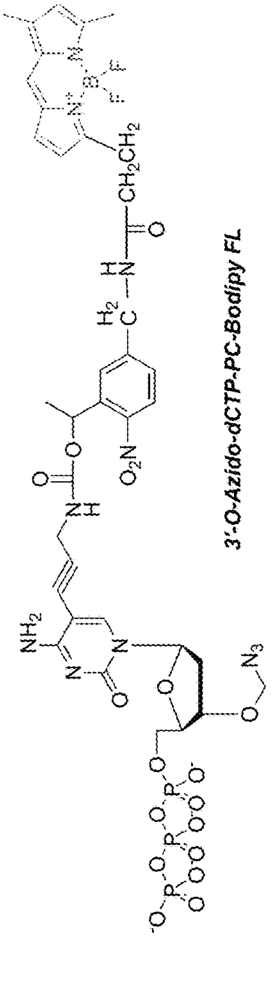
3'-O-Azido-dCTP-PC-Bodipy FL
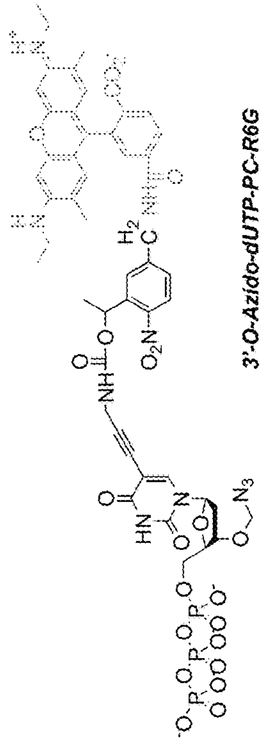
3'-O-Azido-dUTP-PC-R6G Fig. 6
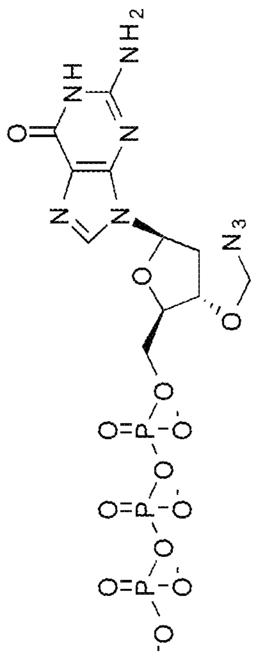
3'-O-Azido-dGTP
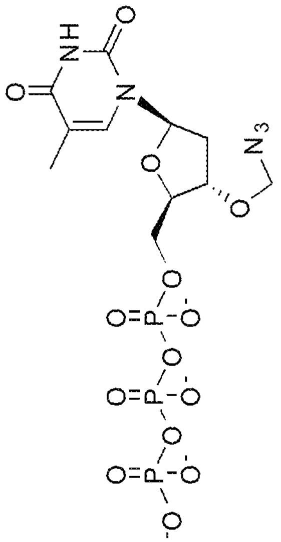
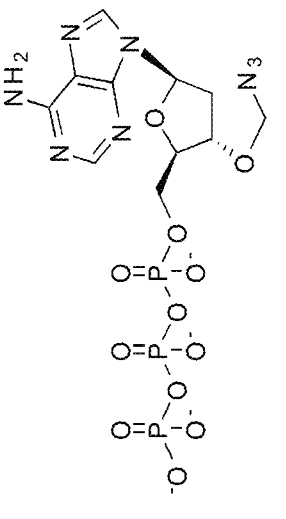
3'-O-Azido-dATP
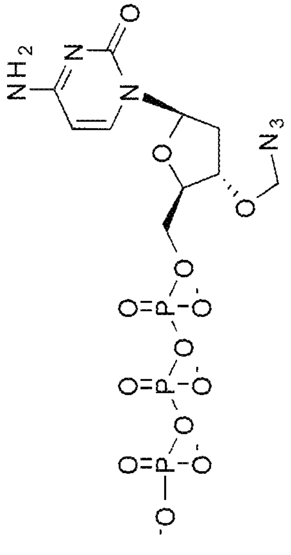

A
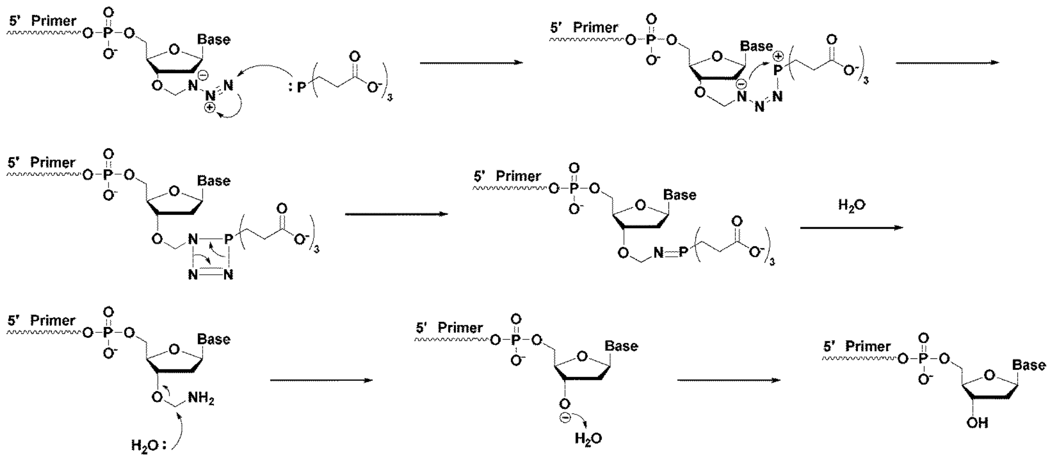
B
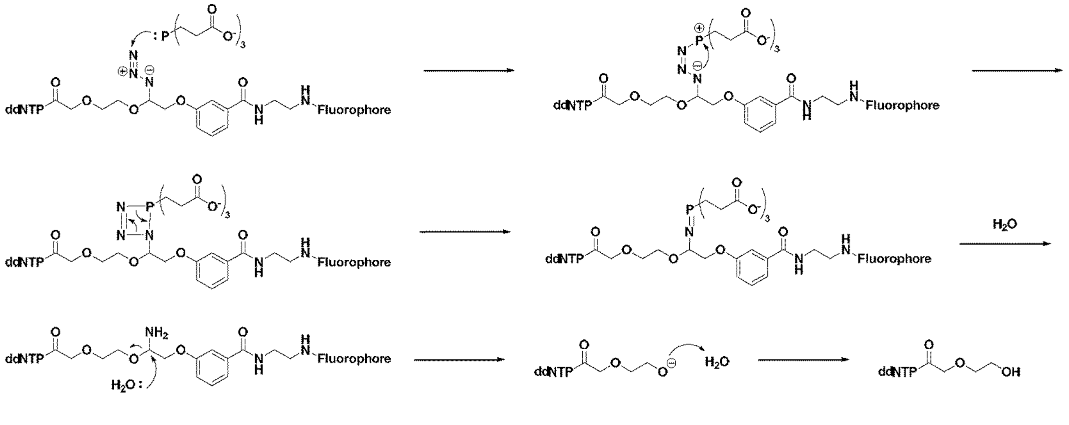
Figs. 13A-B

Fig. 14
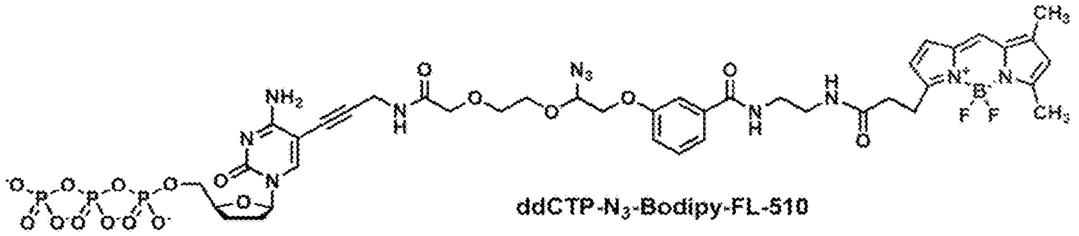
ddCTP-$N_3$-Bodipy-FL-510
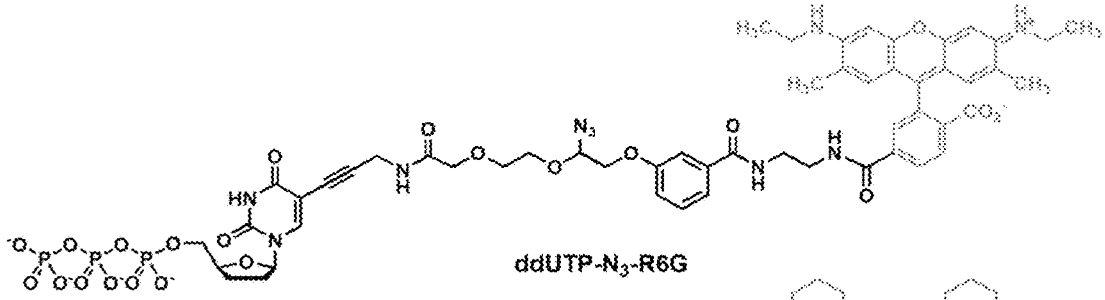
ddUTP-$N_3$-R6G
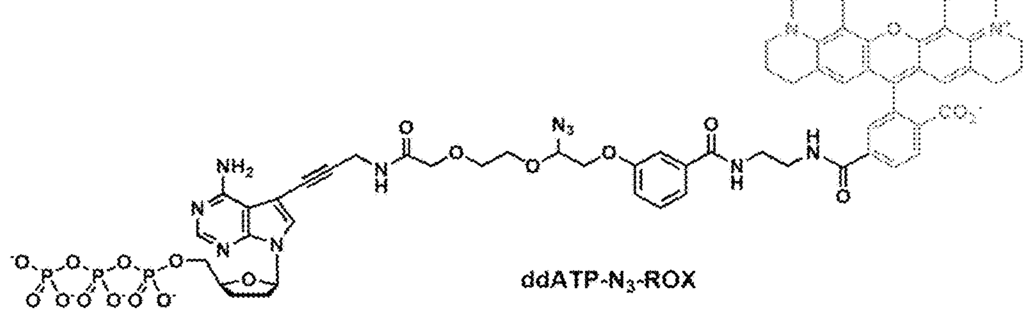
ddATP-$N_3$-ROX
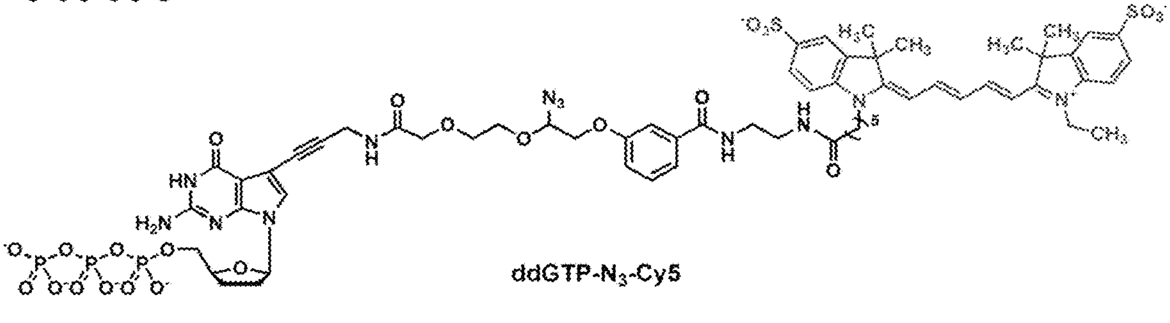
ddGTP-$N_3$-Cy5

The polymerase extension scheme (Left) and MALDI-TOF MS spectra of the four consecutive extension products and their cleavage products (Right) using four 3′-O-N3-dNTPs

Fig. 24
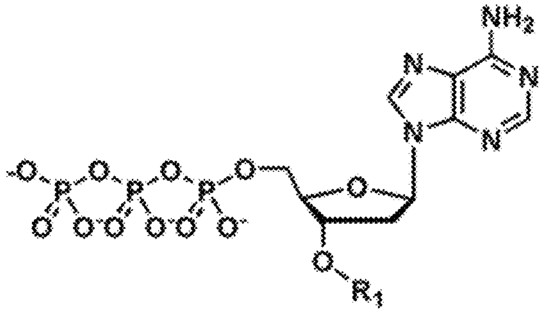
3'-*O*-$R_1$-dATP
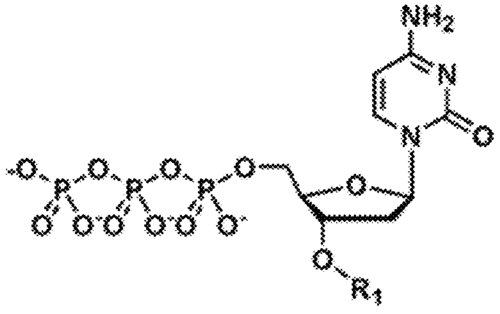
3'-*O*-$R_1$-dCTP
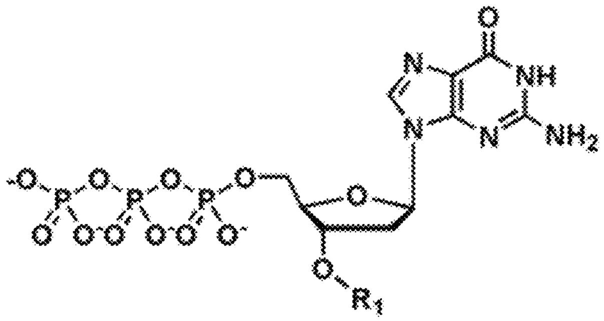
3'-*O*-$R_1$-dGTP
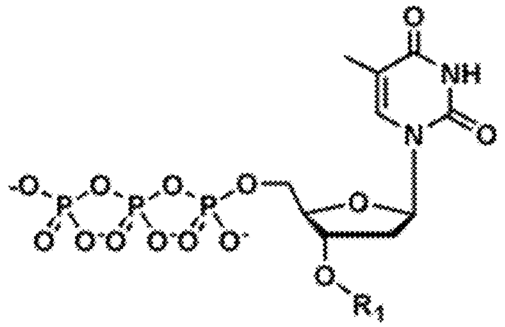
3'-*O*-$R_1$-dTTP Fig. 25
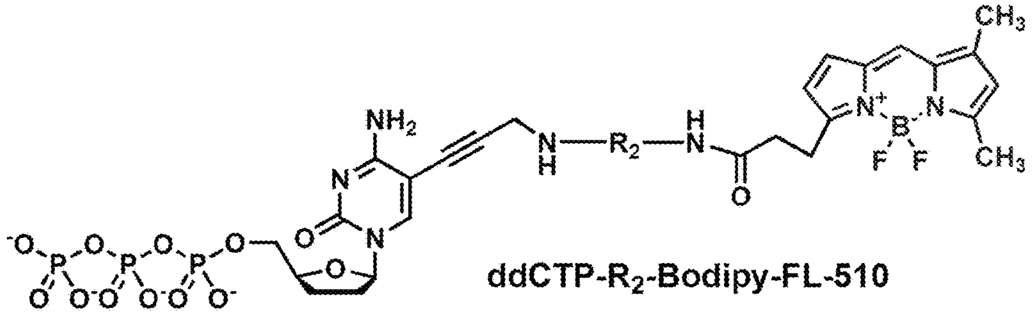
ddCTP-$R_2$-Bodipy-FL-510
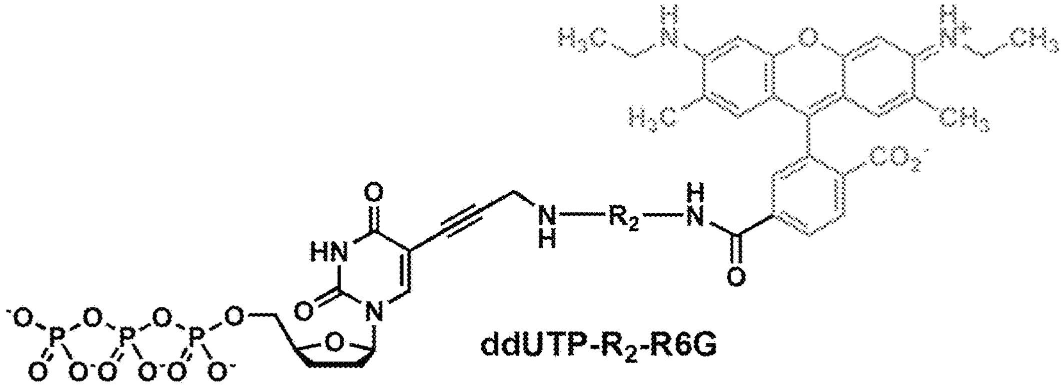
ddUTP-$R_2$-R6G
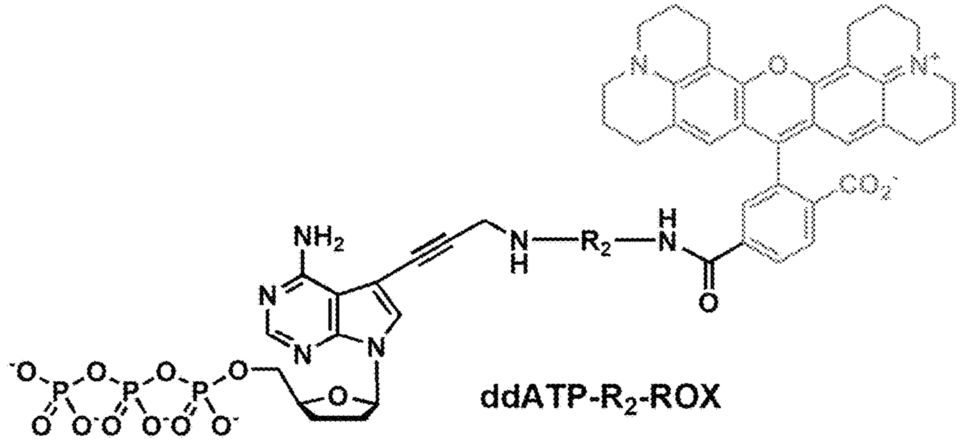
ddATP-$R_2$-ROX
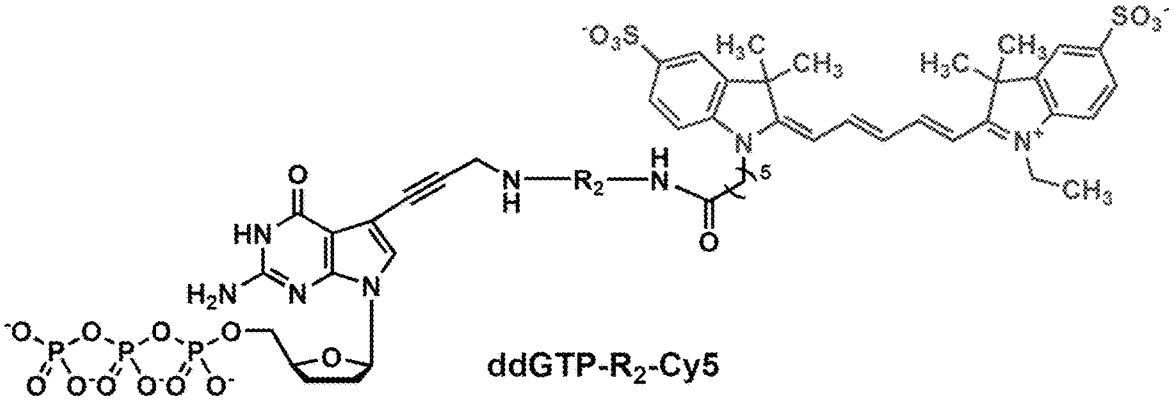
ddGTP-$R_2$-Cy5

Fig. 32
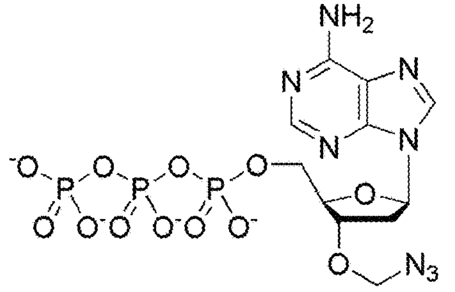
3'-*O*-$N_3$-dATP
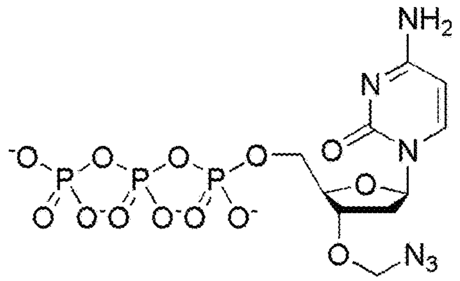
3'-*O*-$N_3$-dCTP
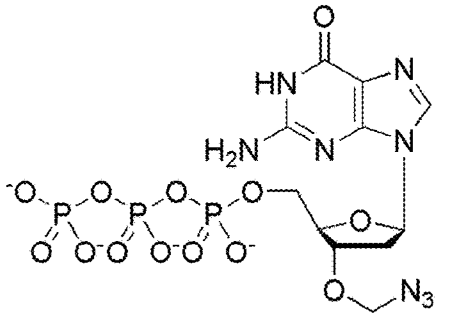
3'-*O*-$N_3$-dGTP
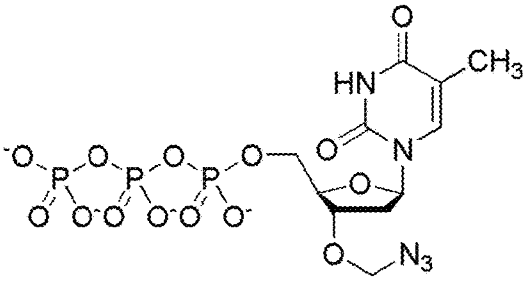
3'-*O*-$N_3$-dTTP Fig. 33
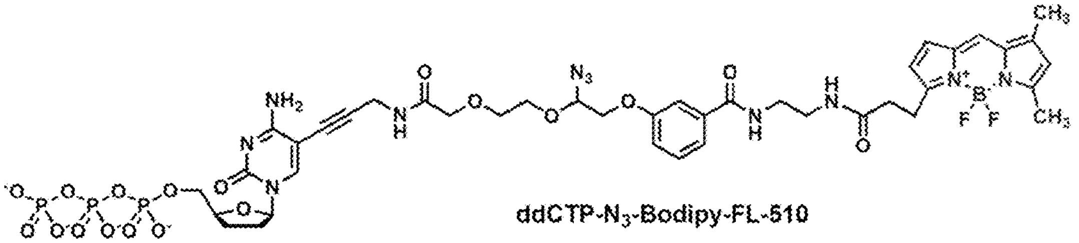
ddCTP-$N_3$-Bodipy-FL-510
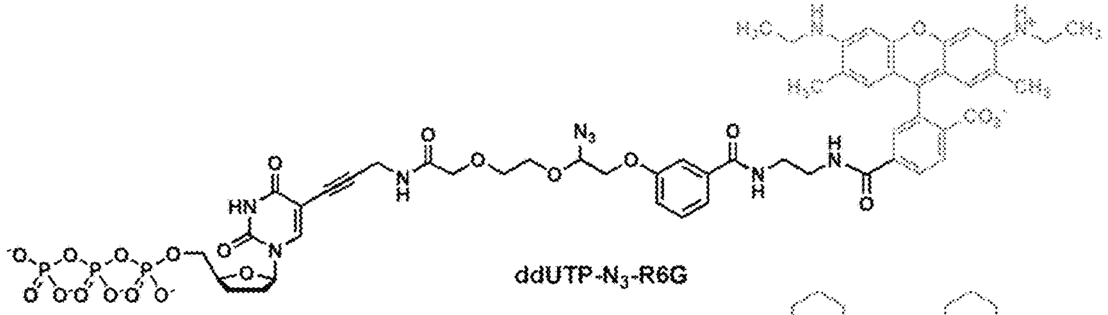
ddUTP-$N_3$-R6G
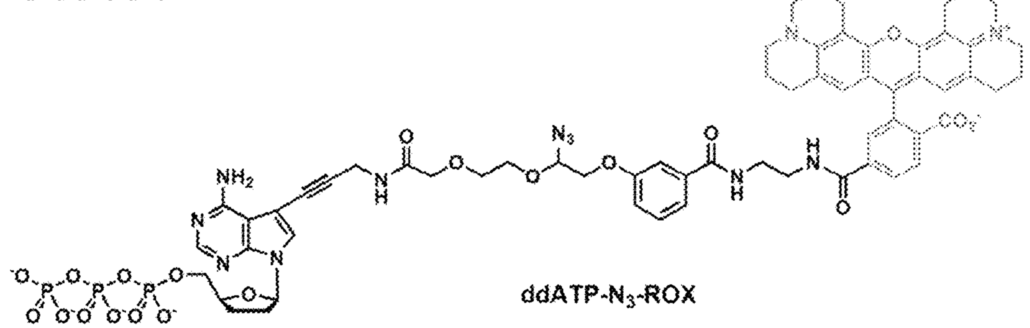
ddATP-$N_3$-ROX
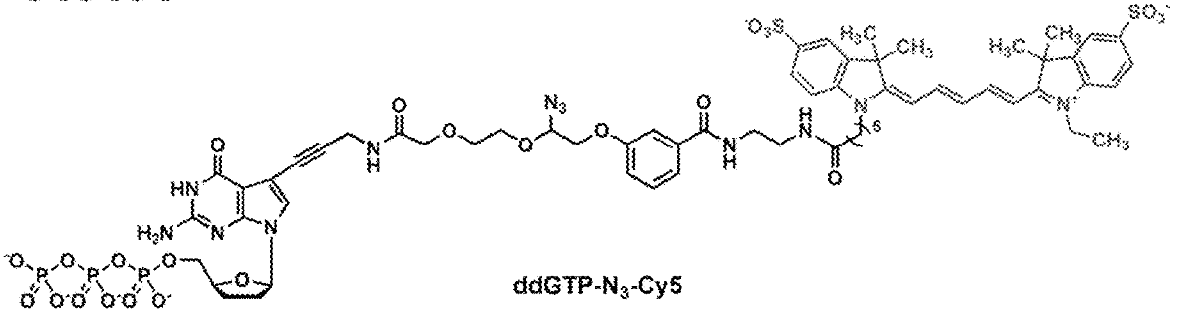
ddGTP-$N_3$-Cy5

A
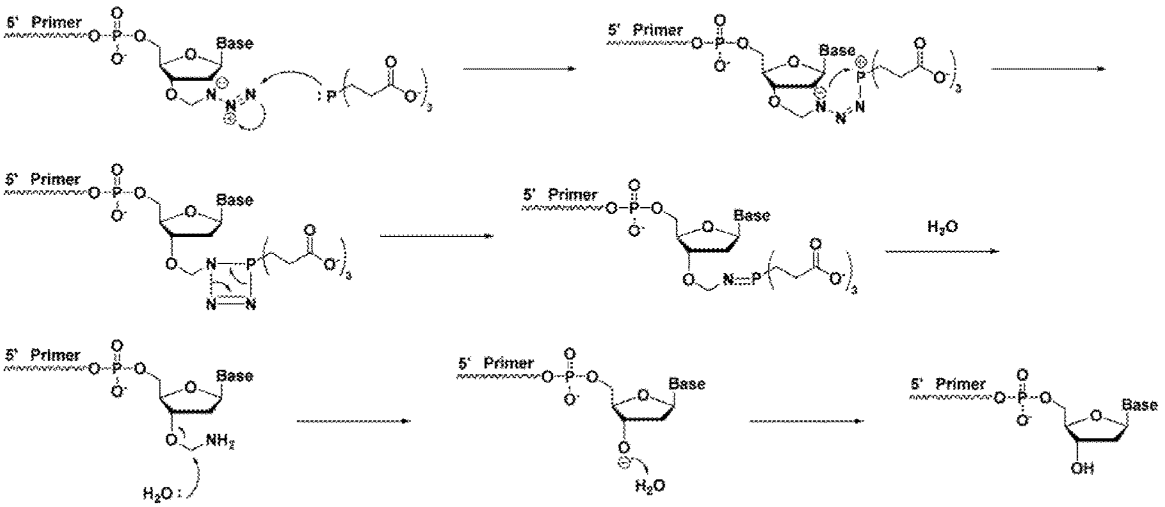
B
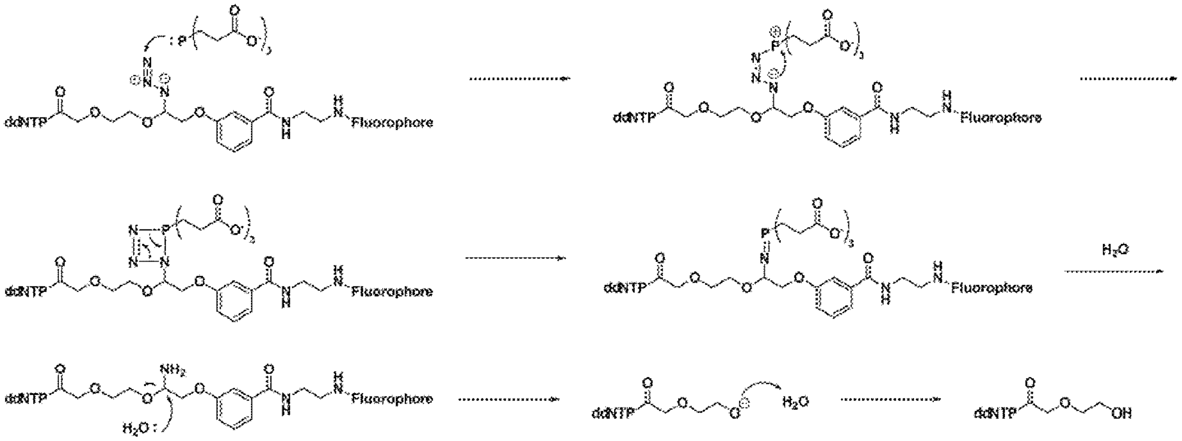
Figs. 34A-B

Fig. 38
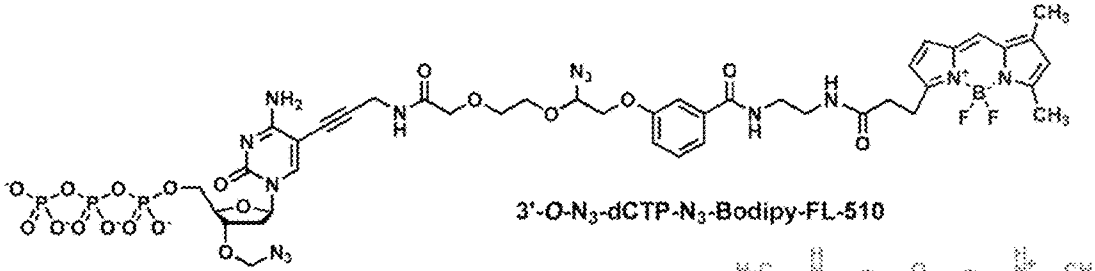
3'-*O*-$N_3$-dCTP-$N_3$-Bodipy-FL-510
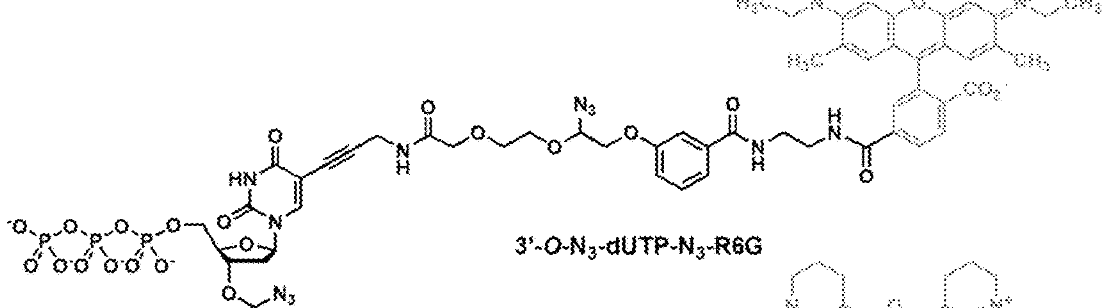
3'-*O*-$N_3$-dUTP-$N_3$-R6G
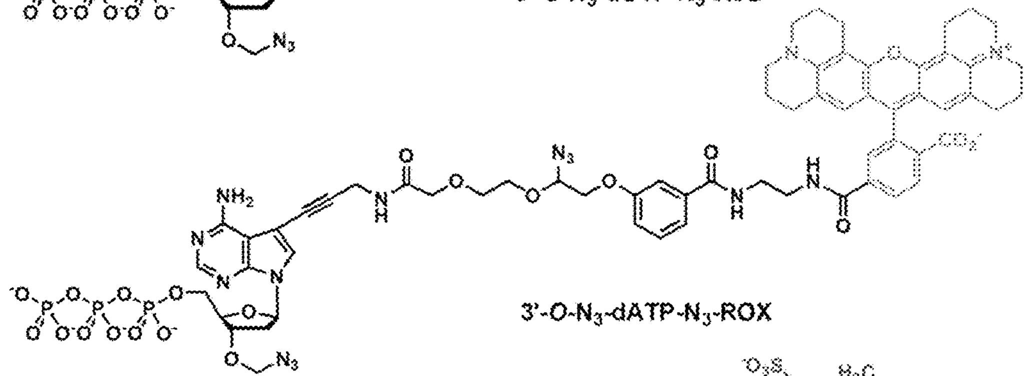
3'-*O*-$N_3$-dATP-$N_3$-ROX
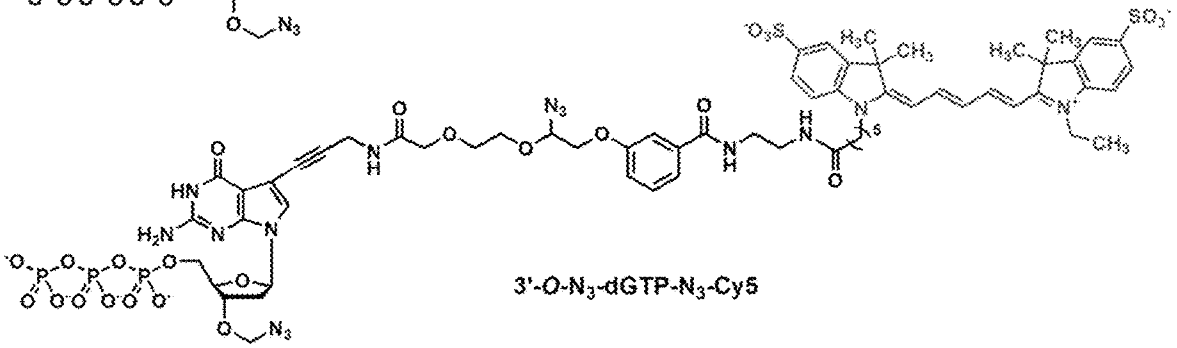
3'-*O*-$N_3$-dGTP-$N_3$-Cy5

Figs. 39A-C

SEQUENCE LISTING

```
Sequence total quantity: 17
SEQ ID NO: 1            moltype = DNA  length = 26
FEATURE                 Location/Qualifiers
misc_feature            1..26
                        note = self-priming DNA template for Polymerase extension
                         reaction
source                  1..26
                        mol_type = other DNA
                        organism = synthetic construct
SEQUENCE: 1
atcggcgccg cgccttggcg cggcgc                                       26

SEQ ID NO: 2            moltype = DNA  length = 26
FEATURE                 Location/Qualifiers
misc_feature            1..26
                        note = self-priming DNA template for polymerase extension
                         reaction
source                  1..26
                        mol_type = other DNA
                        organism = synthetic construct
SEQUENCE: 2
gactgcgccg cgccttggcg cggcgc                                       26

SEQ ID NO: 3            moltype = DNA  length = 26
FEATURE                 Location/Qualifiers
misc_feature            1..26
                        note = self-priming DNA template for polymerase extension
                         reaction
source                  1..26
                        mol_type = other DNA
                        organism = synthetic construct
SEQUENCE: 3
atcggcgccg cgccttggcg cggcgc                                       26

SEQ ID NO: 4            moltype = DNA  length = 26
FEATURE                 Location/Qualifiers
misc_feature            1..26
                        note = self-priming DNA template for polymerase extension
                         reaction for ddGTP-N3-Cy5
source                  1..26
                        mol_type = other DNA
                        organism = synthetic construct
SEQUENCE: 4
gatcgcgccg cgccttggcg cggcgc                                       26

SEQ ID NO: 5            moltype = DNA  length = 26
FEATURE                 Location/Qualifiers
misc_feature            1..26
                        note = self-priming DNA template for polymerase extension
                         reaction for ddNTP-N3-R6G
source                  1..26
                        mol_type = other DNA
                        organism = synthetic construct
SEQUENCE: 5
gtcagcgccg cgccttggcg cggcgc                                       26

SEQ ID NO: 6            moltype = DNA  length = 80
FEATURE                 Location/Qualifiers
misc_feature            1..80
                        note = 5' -amino-labeled self-priming DNA template for
                         polymerase extension reaction
source                  1..80
                        mol_type = other DNA
                        organism = synthetic construct
SEQUENCE: 6
cactcacata tgttttttag cttttttaat ttcttaatga tgttgttgca tgcgacttaa  60
ggcgcttgcg ccttaagtcg                                              80
```

```
SEQ ID NO: 7            moltype = DNA  length = 15
FEATURE                 Location/Qualifiers
misc_feature            1..15
                        note = 15 nucleotides of a 130 bp self-priming DNA template
                         for polymerase extension reaction
source                  1..15
                        mol_type = other DNA
                        organism = synthetic construct
SEQUENCE: 7
actgaacatc tgcat                                                   15

SEQ ID NO: 8            moltype = DNA  length = 21
FEATURE                 Location/Qualifiers
misc_feature            1..21
                        note = 21 nucleotides of a self-priming DNA template for
                         polymerase extension reaction
source                  1..21
                        mol_type = other DNA
                        organism = synthetic construct
SEQUENCE: 8
tgttaatcat gttgttgcat g                                            21

SEQ ID NO: 9            moltype = DNA  length = 14
FEATURE                 Location/Qualifiers
misc_feature            1..14
                        note = DNA template for template "walking"
source                  1..14
                        mol_type = other DNA
                        organism = synthetic construct
SEQUENCE: 9
aatcatctcg catg                                                    14

SEQ ID NO: 10           moltype = DNA  length = 10
FEATURE                 Location/Qualifiers
misc_feature            1..10
                        note = Polymerase extension reaction product of SEQ ID No: 9
modified_base           10
                        mod_base = OTHER
                        note =
                         9-[2-(Ethoxycarbonyl)phenyl]-N-ethyl-6-(ethylamino)-2,7-dim
                         ethyl-3H-xanthen-3-iminium chloride dye with R2 linker
                        note = uracil
source                  1..10
                        mol_type = other DNA
                        organism = synthetic construct
SEQUENCE: 10
catgcgagat                                                         10

SEQ ID NO: 11           moltype = DNA  length = 10
FEATURE                 Location/Qualifiers
misc_feature            1..10
                        note = Polymerase extension reaction product of SEQ ID No: 9
modified_base           10
                        mod_base = OTHER
                        note = Small 3' reversible moiety R1
source                  1..10
                        mol_type = other DNA
                        organism = synthetic construct
SEQUENCE: 11
catgcgagat                                                         10

SEQ ID NO: 12           moltype = DNA  length = 14
FEATURE                 Location/Qualifiers
misc_feature            1..14
                        note = DNA template for template "walking"
source                  1..14
                        mol_type = other DNA
                        organism = synthetic construct
SEQUENCE: 12
aatctactag catg                                                    14

SEQ ID NO: 13           moltype = DNA  length = 10
FEATURE                 Location/Qualifiers
misc_feature            1..10
                        note = Polymerase extension reaction product of SEQ ID No:
                         12
```

-continued

```
modified_base          10
                       mod_base = OTHER
                       note =
                        4-carboxy-3-(3-oxa-23-aza-9-azoniaheptacyclo[17.7.1.15,9.02
                        ,17.04,15.023,27.013,28]octacosa-1(27),2(17),4,9(28),13,15,
                        18-heptaen-16-yl)benzoate dye with linker R2
source                 1..10
                       mol_type = other DNA
                       organism = synthetic construct
SEQUENCE: 13
catgctagta                                                  10

SEQ ID NO: 14          moltype = DNA  length = 10
FEATURE                Location/Qualifiers
misc_feature           1..10
                       note = Polymerase extension reaction product of SEQ ID No:
                        12
modified_base          10
                       mod_base = OTHER
                       note = Small 3' reversible moiety R1
source                 1..10
                       mol_type = other DNA
                       organism = synthetic construct
SEQUENCE: 14
catgctagta                                                  10

SEQ ID NO: 15          moltype = DNA  length = 10
FEATURE                Location/Qualifiers
misc_feature           1..10
                       note = Polymerase extension reaction product of SEQ ID No: 9
modified_base          10
                       mod_base = OTHER
                       note =
                        9-[2-(Ethoxycarbonyl)phenyl]-N-ethyl-6-(ethylamino)-2,7-dim
                        ethyl-3H-xanthen-3-iminium fluorescence dye with R2 linker
                        and 3' small reversible moiety R1
                       note = uracil
source                 1..10
                       mol_type = other DNA
                       organism = synthetic construct
SEQUENCE: 15
catgcgagat                                                  10

SEQ ID NO: 16          moltype = DNA  length = 10
FEATURE                Location/Qualifiers
misc_feature           1..10
                       note = Polymerase extension reaction product of SEQ ID No:
                        12
modified_base          10
                       mod_base = OTHER
                       note =
                        4-carboxy-3-(3-oxa-23-aza-9-azoniaheptacyclo[17.7.1.15,9.02
                        ,17.04,15.023,27.013,28]octacosa-1(27),2(17),4,9(28),13,15,
                        18-heptaen-16-yl)benzoate fluorescence moiety with R2
                        linker and 3' small reversible moiety R1
source                 1..10
                       mol_type = other DNA
                       organism = synthetic construct
SEQUENCE: 16
catgctagta                                                  10

SEQ ID NO: 17          moltype = DNA  length = 10
FEATURE                Location/Qualifiers
misc_feature           1..10
                       note = Polymerase extension reaction product of SEQ ID No:
                        12
modified_base          10
                       mod_base = OTHER
                       note = 3' small reversible moiety R1
source                 1..10
                       mol_type = other DNA
                       organism = synthetic construct
modified_base          9
                       mod_base = OTHER
                       note = uracil
SEQUENCE: 17
catgctagta                                                  10
```

AND SYNTHESIS OF CLEAVABLE FLUORESCENT NUCLEOTIDES AS REVERSIBLE TERMINATORS FOR DNA SEQUENCING BY SYNTHESIS

This application is a continuation of U.S. application Ser. No. 19/001,296, filed Dec. 24, 2024, which is a continuation of U.S. application Ser. No. 17/560,928, filed Dec. 23, 2021, now U.S. Pat. No. 12,180,544, issued Dec. 31, 2024, which is a continuation of U.S. application Ser. No. 16/208,379, filed Dec. 3, 2018, now U.S. Pat. No. 11,208,691, issued Dec. 28, 2021, which is a continuation of U.S. application Ser. No. 15/596,379, filed May 16, 2017, now U.S. Pat. No. 10,144,961, issued Dec. 4, 2018, which is a continuation of U.S. application Ser. No. 14/859,853, filed Sep. 21, 2015, now U.S. Pat. No. 9,670,539, issued Jun. 6, 2017, which is a continuation of U.S. application Ser. No. 13/951,269, filed Jul. 25, 2013, now U.S. Pat. No. 9,175,342, issued Nov. 3, 2015, which is a continuation of U.S. application Ser. No. 12/734,227, filed Aug. 30, 2010, now abandoned, which is a section 371 national stage based on PCT International Application No. PCT/US2008/011891, filed Oct. 17, 2008, claiming the benefit of U.S. Provisional Application No. 60/999,576, filed Oct. 19, 2007, the contents of each of which are hereby incorporated by reference into the subject application.

This invention was made with government support under HG003582 awarded by the National Institute of Health. The government has certain rights in the invention.

REFERENCE TO SEQUENCE LISTING

This application incorporated-by-reference nucleotide and/or amino acid sequences which are present in the file "2508 12 78341-A7B-PCT-named US_SequenceListing_AD. xml", which is 28 kilobytes in size, and which was created on Aug. 12, 2025 in the IBM-PC machine format, having an operating system compatibility with MS-Windows, which is contained in the xml file filed Aug. 12, 2025 as part of this application.

Throughout this application, various publications are referenced in parentheses by number. Full citations for these references may be found at the end of the specification immediately preceding the claims. The disclosures of these publications in their entireties are hereby incorporated by reference into this application to more fully describe the state of the art to which this invention pertains.

BACKGROUND OF THE INVENTION

The completion of the Human Genome Project (HGP) in early 2000 (1) was a monumental achievement with incredible amount of combined efforts among genome centers and scientists worldwide. The engine behind this decade long project was the Sanger sequencing method, which still currently maintains as the staple of large-scale genome sequencing methodology in high-throughput genome sequencing centers. The main reason behind this prolonged success was in the basic and efficient, yet elegant method that is Sanger dideoxy chain terminating reaction (2). With incremental improvements in this DNA sequencing technology including the use of laser induced fluorescent excitation of energy transfer dyes (3), engineered DNA polymerases (4) and capillary electrophoresis (5) as well as in the areas of sample preparation, informatics, and sequence analysis software (6-9), the Sanger sequencing platform has been able to maintain its status as champion in the sequencing world. Current state-of-the-art Sanger based DNA sequencers can produce over 700 bases of clearly readable sequence in a single run from templates up to 30 kb in length (10-12). However, as is with most of technological inventions, the continual improvements in this sequencing platform has come to a stagnant plateau, with the current cost estimate for producing a high-quality microbial genome draft sequence at around $10,000 per megabase pair. Current DNA sequencers based on the Sanger method allow up to 384 samples to be analyzed in parallel.

While fluorescent-based SBS methods have almost unlimited ability for parallelization, restricted only by the resolution of the imaging system, to date they have been limited to read lengths of about 35 bases. The successful implementation of sequencing by synthesis (SBS) is effectively dependent on the read length of the target DNA template. One of the major factors that determines the read length when performing SBS is the number of available templates. Our laboratory has recently developed two powerful approaches for SBS: 1) Hybrid SBS with nucleotide reversible terminator (NRTs, 3'-O—$R_1$-dNTPs) in combination with fluorescently labeled dideoxynucleotide (ddNTPs-$R_2$-fluorophore), and 2) SBS with cleavable fluorescent nucleotide reversible terminator (C—F—NRTs, 3'-O—$R_1$-dNTPs-$R_2$-fluorophore). ("Four-color DNA Sequencing with 3'-O-modified Nucleotide Reversible Terminators and Chemically Cleavable Fluorescent Dideoxynucleotides". J. Guo, N. Xu, Z. Li, S. Zhang, J. Wu, D. Kim, M. S. Marma, Q. Meng, H. Cao, X. Li, S. Shi, L. Yu, S. Kalachikov, J. Russo, N. J. Turro, J. Ju. Proceedings of the National Academy of Sciences USA. 2008, 105, 9145-9150) ("Four-Color DNA Sequencing by Synthesis Using Cleavable Fluorescent Nucleotide Reversible Terminators". J. Ju, D. Kim, L. Bi, Q. Meng, X. Bai, Z. Li, X. Li, M. S. Marma, S. Shi, J. Wu, J. R. Edwards, A. Romu, N. J. Turro. Proceedings of the National Academy of Sciences USA. 2006, 103, 19635-19640). Since the incorporation of ddNTPs-$R_2$-fluorophore into a strand of DNA permanently terminates further extensions of that template in the first approach and the incorporation and cleavage of C—F—NRTs leaves a tail of the modified nucleotide that causes possible steric hindrance to lower the incorporation efficiency of the subsequent base in the second approach, the total number of sequenceable templates decreases after each cycle of SBS reaction. Various means can be employed to minimize this rate of template reduction. Among those, a powerful method termed template "walking" can potentially diminish the negative effect of template termination or reduction and extend the read length of SBS at least two to three-fold.

SUMMARY OF THE INVENTION

A composition is provided having a first, second and third portion wherein the second portion has the following structure:

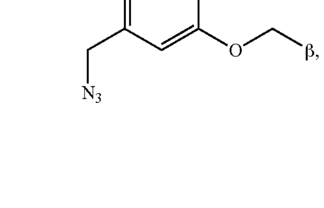

wherein α represents a point of attachment to the first portion and β represents a point of attachment to the third portion.

A method is provided for determining the identity of each of a series of consecutive nucleotide residues in a nucleic acid comprising:

a) contacting the nucleic acid with (i) at least four different deoxynucleotide triphosphate (dNTP) analogues, each having the structure:

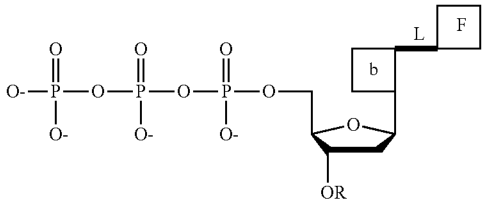

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

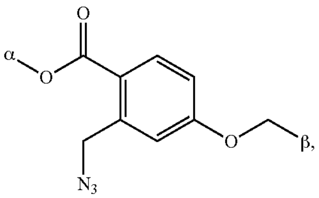

wherein α represents a point of attachment to the base and β represents a point of attachment to the fluorophore, and wherein R is a cleavable chemical group, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method is provided for determining the identity of each of a series of consecutive nucleotide residues in a self-priming nucleic acid comprising:

a) contacting the self-priming nucleic acid with (i) at least four different deoxynucleotide triphosphate (dNTP) analogues, each having the structure:

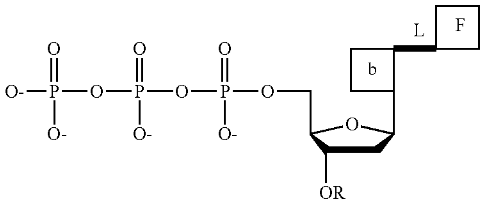

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

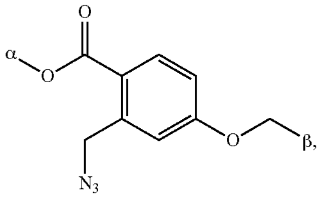

wherein β represents a point of attachment to the base and β represents a point of attachment to the fluorophore, and wherein R is a cleavable chemical group, and (ii) a nucleic acid polymerase, under conditions permitting (a) the self-priming nucleic acid to prime itself and (b) one of the four dNTP analogues that is complementary to the consecutive nucleotide residue to be identified to form a phosphodiester bond with the 3' end of the self-priming nucleic acid primer and thereby extend the self-priming nucleic acid;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the self-priming nucleic acid.

A kit is provided for use in sequencing a nucleic acid comprising:
a) a plurality of four nucleotide analogues having the structure:
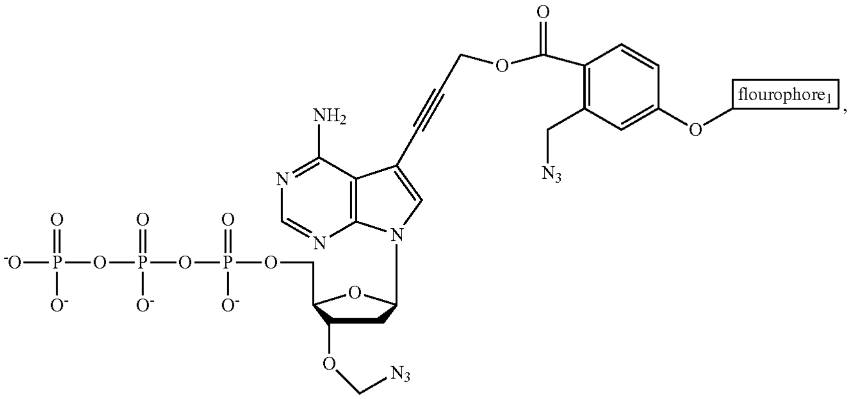
,
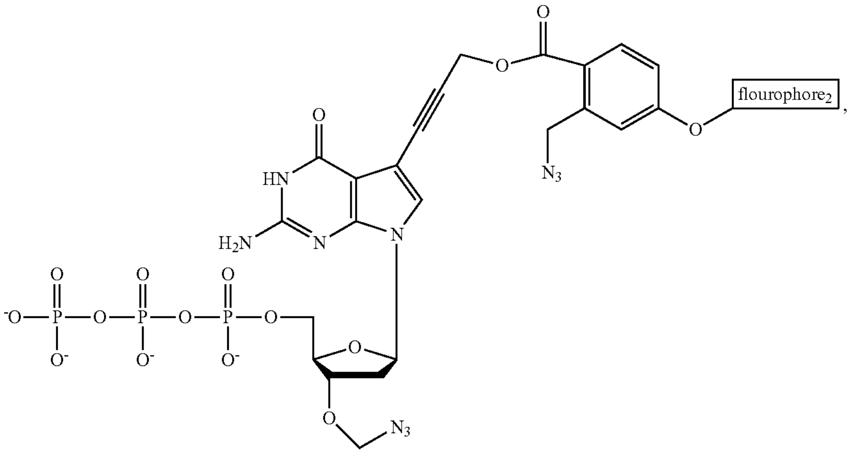
,
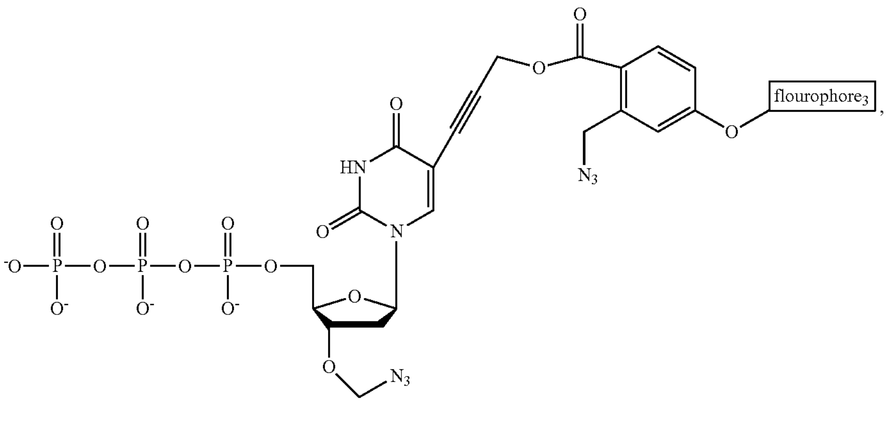
, and -continued

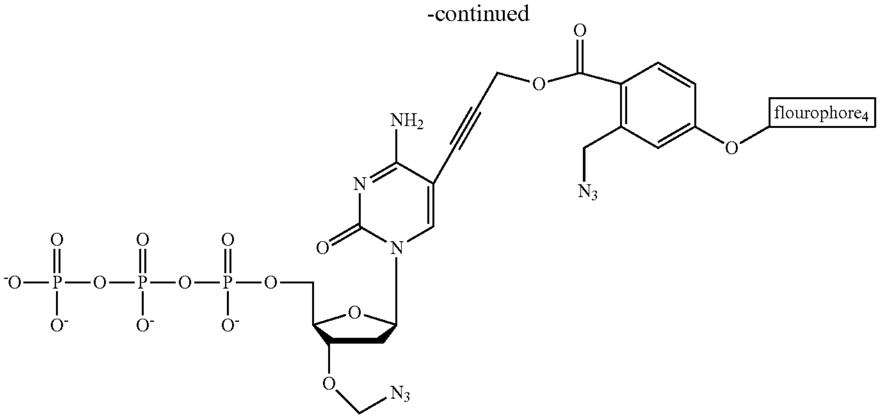

and b) instructions for use.

An array is provided comprising a nucleic acid attached to a solid surface, wherein the nucleic acid comprises an azidomethyl group attached to a 3' O atom thereof and a molecule having the structure:

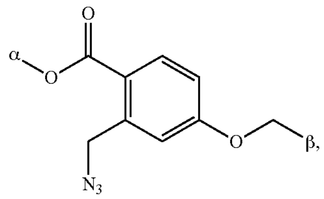

wherein α represents a point of attachment to a 3' base of the nucleic acid and β represents a point of attachment to a detectable marker.

An array is provided comprising a self-priming nucleic acid attached to a solid surface, wherein the nucleic acid comprises an azidomethyl group attached to a 3' O atom thereof and a molecule having the structure:

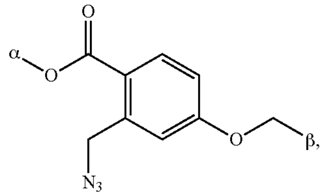

wherein α represents a point of attachment to a 3' base of the nucleic acid and β represents a point of attachment to a detectable marker.

A method is provided for increasing a read length of DNA sequencing by synthesis comprising (a) providing deoxynucleotide triphosphate analogues wherein the deoxynucleotide triphosphate analogues differ from deoxynucleotide triphosphates by having a methylazido group attached to a 3' O atom thereof and by having a detectable marker attached to a 1 nitrogen or a 9 nitrogen of a base thereof through a linker comprising the structure

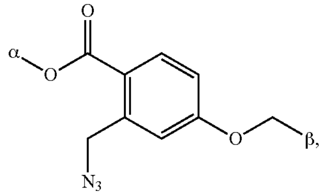

wherein α represents a point of attachment to a the base and β represents a point of attachment to the detectable marker, (b) incorporating a plurality of the deoxynucleotide triphosphate analogues into a nucleic acid being synthesized in the DNA sequencing by synthesis, and (c) cleaving the methylazido and detectable marker from each incorporated dNTP analogue, so as to thereby increase the readlength of the DNA sequence by synthesis.

A method for determining the identity of each of a series of consecutive nucleotide residues in a nucleic acid comprising:

a) contacting the nucleic acid with (i) at least four different deoxynucleotide triphosphate (dNTP) analogues, each having the structure:

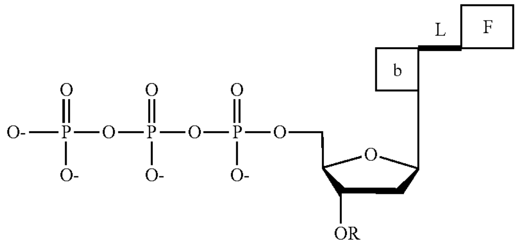

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

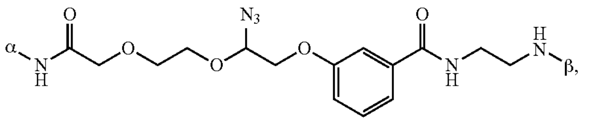

wherein α represents a point of attachment to the base and β represents a point of attachment to the fluorophore, and wherein R is a cleavable chemical group, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method for determining the identity of each of a series of consecutive nucleotide residues in a self-priming nucleic acid comprising:

a) contacting the self-priming nucleic acid with (i) at least four different deoxynucleotide triphosphate (dNTP) analogues, each having the structure:

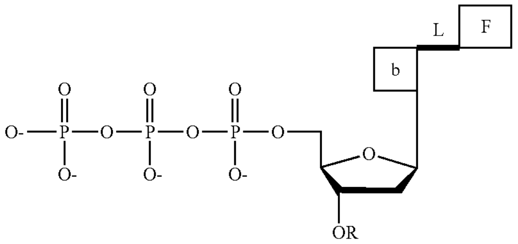

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

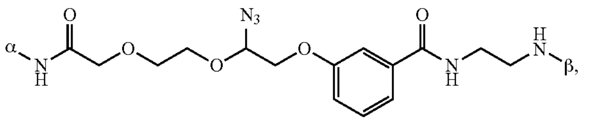

wherein α represents a point of attachment to the base and β represents a point of attachment to the fluorophore, and wherein R is a cleavable chemical group, and (ii) a nucleic acid polymerase, under conditions permitting (a) the self-priming nucleic acid to prime itself and (b) one of the four dNTP analogues that is complementary to the consecutive nucleotide residue to be identified to form a phosphodiester bond with the 3' end of the self-priming nucleic acid primer and thereby extend the self-priming nucleic acid;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the self-priming nucleic acid.

A method for determining the identity of each of a series of consecutive nucleotide residues in a plurality of nucleic acids comprising, the same series of consecutive nucleotides comprising:

a) contacting the nucleic acids with (i) at least four different dideoxynucleotide triphosphate (ddNTP) analogues, each having the structure:

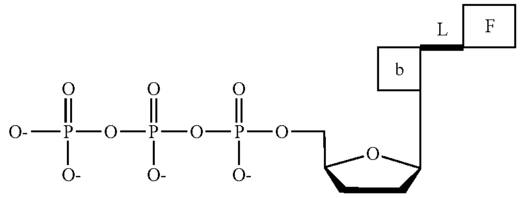

wherein F is a fluorophore, L is a cleavable linker molecule and b is a base which is adenine, guanine, cytosine, uracil or thymine, wherein the fluorophore attached through a linker to each type of base differs in its emission or excitation spectra from a fluorophore attached through a linker to each of the remaining types of bases, and each of the four ddNTP analogues differs from the remaining three ddNTP analogues by having a different base, and wherein L comprises the structure:

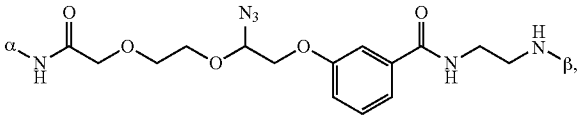

wherein α represents a point of attachment to the base of the dideoxynucleotide and β represents a point of attachment to the fluorophore, and (ii) at least four different deoxynucleotide triphosphate (dNTP) analogue, each having the structure:

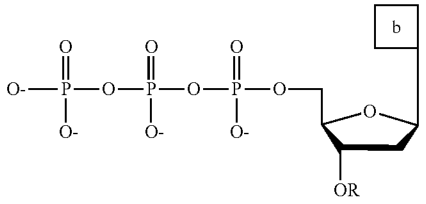

wherein b is a base which is adenine, guanine, cytosine, uracil or thymine, and each of the four dNTP analogues differs from the remaining three dNTP analogues by having a different base, and wherein R is a cleavable chemical group, (iii) a nucleic acid polymerase and (iv) at least two primers each of which hybridizes with a separate nucleic acid of the plurality of nucleic acids, under conditions permitting a ddNTP analogue that is complementary to the consecutive nucleotide residue in the nucleic acid to be identified to form a phosphodiester bond with the 3' end of one of the primers and a dNTP analogue that is complementary to the consecutive nucleotide residue to be identified to form a phosphodiester bond with the 3' end of another of the primers;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method for determining the identity of consecutive nucleotide residues in a self-priming nucleic acid comprising:

a) contacting the nucleic acids with (i) at least four different dideoxynucleotide triphosphate (ddNTP) analogues, each having the structure:

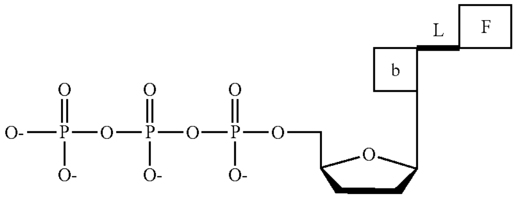

wherein F is a fluorophore, L is a cleavable linker molecule and b is a base which is adenine, guanine, cytosine, uracil or thymine, wherein the fluorophore attached through a linker to each type of base differs in its emission or excitation spectra from a fluorophore attached through a linker to each of the remaining types of bases, and each of the four ddNTP analogues differs from the remaining three ddNTP analogues by having a different base, and wherein L comprises the structure:

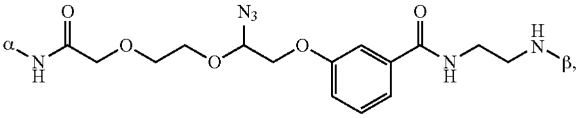

wherein α represents a point of attachment to the base of the dideoxynucleotide and β represents a point of attachment to the fluorophore, and (ii) at least four different deoxynucleotide triphosphate (dNTP) analogue, each having the structure:

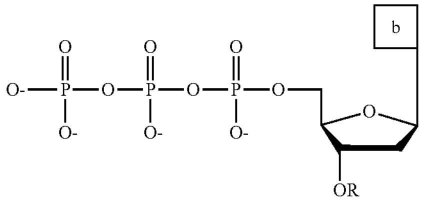

wherein b is a base which is adenine, guanine, cytosine, uracil or thymine, and each of the four dNTP analogues differs from the remaining three dNTP analogues by having a different base, and wherein R is a cleavable chemical group, (iii) a nucleic acid polymerase and (iv) at least two primers each of which hybridizes with a separate nucleic acid of the plurality of nucleic acids, under conditions permitting a ddNTP analogue that is complementary to the consecutive nucleotide residue to be identified to form a phosphodiester bond with the 3' end of one of the self-priming nucleic acids and a dNTP analogue that is complementary to the consecutive nucleotide residue to be identified to form a phosphodiester bond with the 3' end of another of the self-priming nucleic acids;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A kit for use in sequencing a nucleic acid comprising:
a) a plurality of four dideoxynucleotide analogues having the structure:
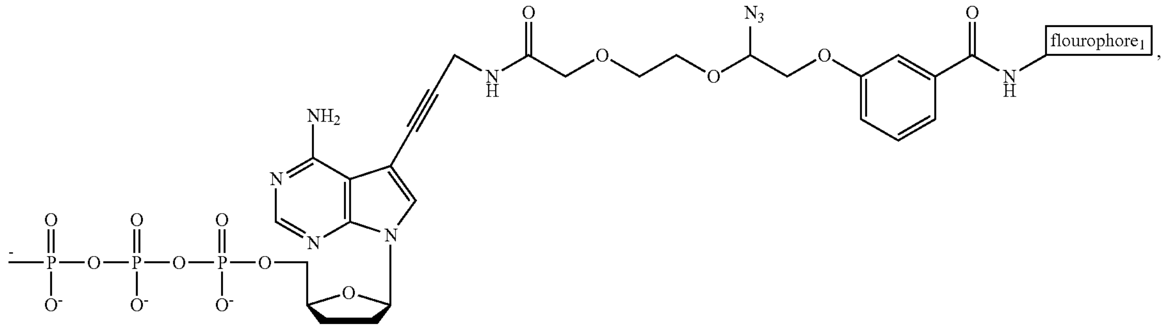
,
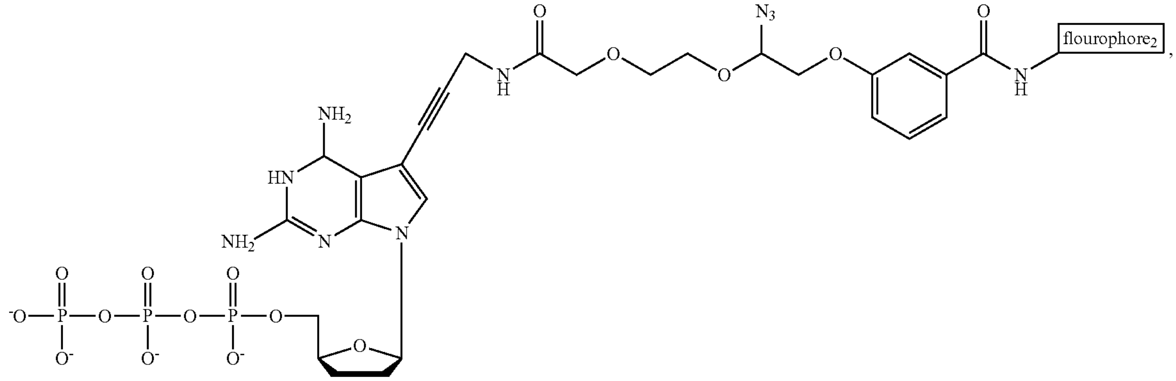
,
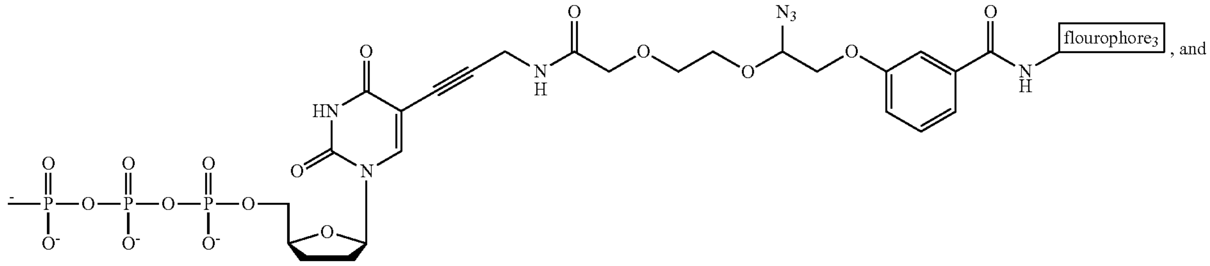
, and
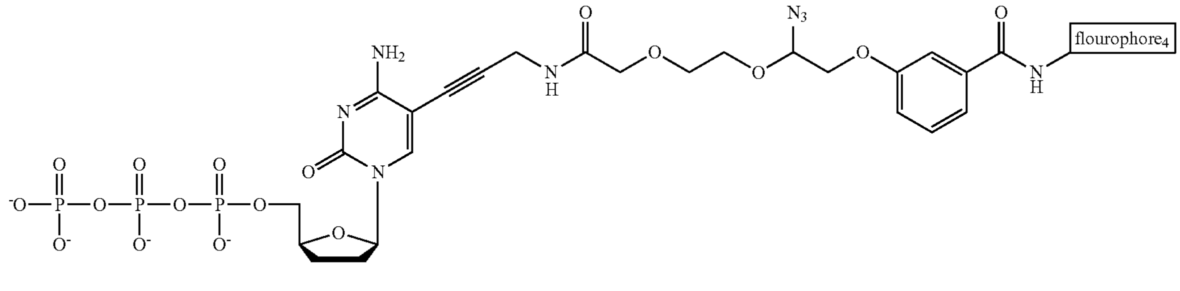

with (b) a plurality of deoxynucleotide analogues having the structure:

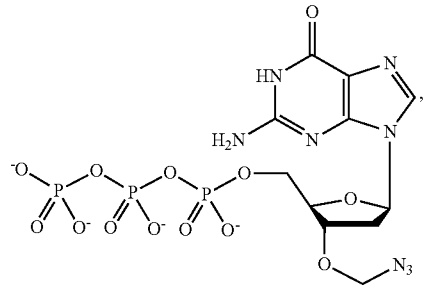

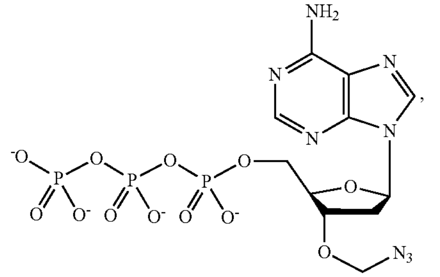

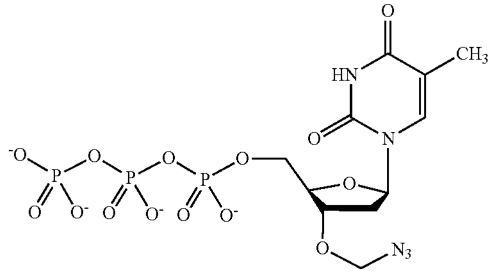

and

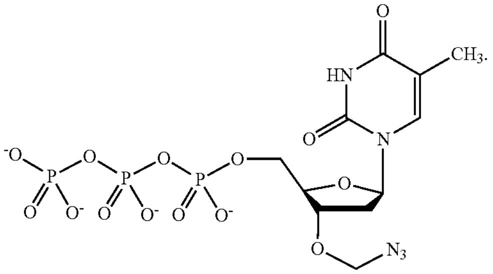

and (c) instructions for use.

An array comprising a nucleic acid attached to a solid surface, wherein the nucleic acid comprises an azidomethyl group attached to a 3' O atom thereof and a molecule having the structure:

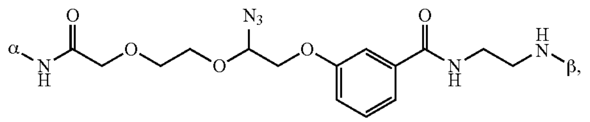

wherein α represents a point of attachment to a 3' base of the nucleic acid and β represents a point of attachment to a detectable marker.

An array comprising a self-priming nucleic acid attached to a solid surface, wherein the nucleic acid comprises an azidomethyl group attached to a 3' O atom thereof and a molecule having the structure:

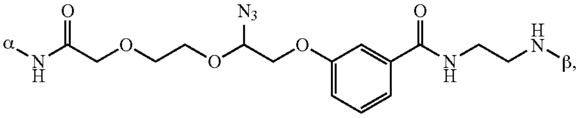

wherein α represents a point of attachment to a 3' base of the nucleic acid and β represents a point of attachment to a detectable marker.

A method is provided for increasing a read length of DNA sequencing by synthesis coupled with Sanger dideoxynucleotide terminating reaction (a) providing deoxynucleotide triphosphate analogues wherein the deoxynucleotide triphosphate analogues differ from deoxynucleotide triphosphates by having a methylazido group attached to a 3' O atom thereof and providing dideoxynucleotide triphosphate analogues wherein the dideoxynucleotide triphosphate analogues differ from dideoxynucleotide triphosphates by having a detectable marker attached to a 1 nitrogen or a 9 nitrogen of a base thereof through a linker comprising the structure

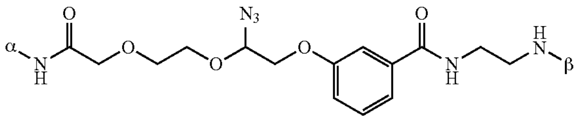

wherein α represents a point of attachment to a the base and β represents a point of attachment to the detectable marker, (b) incorporating a plurality ratio of dideoxynucleotide triphosphate to deoxynucleotide triphosphate analogues into a nucleic acid being synthesized in the DNA sequencing by synthesis and (c) cleaving the methylazido and detectable marker from each incorporated dNTP analogue, so as to thereby increase the readlength of the DNA sequence by synthesis.

BRIEF DESCRIPTION OF THE FIGURES

FIG. 2. 3'-O-Azido-dNTPs-Azido-Dye.

FIG. 4. 3'-O-Azido-dNTP—PC-Dye.

FIG. 6. 3'-O-Azido-dNTPs.

FIGS. 13A-B. Mechanisms to cleave the 3'-O-azidomethyl group and the azidolinker-fluorophore from the DNA extension products. (FIG. 13A) Staudinger reaction with TCEP to regenerate the 3'-OH group of the DNA extension product. (FIG. 13B) Staudinger reaction with TCEP to cleave the fluorophore from the dideoxynucleotide.

FIG. 14. Structures of cleavable fluorescent dideoxynucleotide terminators ddNTP-$N_3$-fluorophores, with the 4 fluorophores having distinct fluorescent emissions: ddCTP-$N_3$-Bodipy-FL-510 ($\lambda_{abs\ (max)}$=502 nm; $\lambda_{em\ (max)}$=510 nm), ddUTP-$N_3$—R6G ($\lambda_{abs\ (max)}$=525 nm; $\lambda_{em\ (max)}$=550 nm), ddATP-$N_3$—ROX ($\lambda_{abs\ (max)}$=585 nm; $\lambda_{em\ (max)}$=602 nm), and ddGTP-$N_3$-Cy5 ($\lambda_{abs\ (max)}$=649 nm; $\lambda_{em\ (max)}$=670 nm).

FIGS. 19A-H. A detailed scheme (left half of fig.) of polymerase reaction using all four 3'-O—$N_3$-dNTPs to extend with an "3'-O—$N_3$-dATP", "3'-O—$N_3$-dCTP", "3'-O—$N_3$-dGTP" and "3'-O—$N_3$-dTTP" and the subsequent cleavage reaction to cleave off the azidomethyl moiety capping the 3'-OH of the DNA extension product. MALDI-TOF MS spectra (right half of fig.) verifying base specific incorporation of: (FIG. 19A) 3'-O—$N_3$-dCTP (peak at 8,310 m/z), (FIG. 19B) the corresponding cleavage product (8,255 m/z); (FIG. 19C) 3'-O—$N_3$-dGTP (peak at 8,639 m/z), (FIG. 19D) the corresponding cleavage product (8,584 m/z); (FIG. 19E) 3'-O—$N_3$-dATP (peak at 8,952 m/z), (FIG. 19F) the corresponding cleavage product (8,897 m/z); (FIG. 19G) 3'-O—$N_3$-dTTP (peak at 9,256 m/z) and (FIG. 19H) the corresponding cleavage product (9,201 m/z). The azidomethyl moiety capping the 3'-OH group of the DNA extension products is completely removed by TCEP aqueous solution to continue the polymerase reaction.

FIGS. 20A-20H. A detailed scheme (top half of fig.) of polymerase reaction using all four ddATP-$N_3$-fluorophores to extend with an "ddA", "ddC", "ddG" and "ddU" and the subsequent cleavage reaction to cleave off the fluorophore from the DNA extension product. MALDI-TOF MS spectra (bottom half of fig.) verifying base specific incorporation of: (FIG. 20A) ddATP-$N_3$—ROX (peak at 9,180 m/z) among pool of all four cleavable fluorescent dideoxynucleotides, (FIG. 20B) the corresponding cleavage product (8,417 m/z); (FIG. 20C) ddCTP-$N_3$-Bodipy-FL-510 (peak at 8,915 m/z), (FIG. 20D) the corresponding cleavage product (8,394 m/z); (FIG. 20E) ddGTP-$N_3$-Cy5 (peak at 9,317 m/z), (FIG. 20F) the corresponding cleavage product (8,433 m/z); (FIG. 20G) ddUTP-$N_3$-R6G (peak at 9,082 m/z) and (FIG. 20H) the corresponding cleavage product (8,395 m/z).

(FIG. 21A) Reaction scheme of Sanger/sequencing by synthesis hybrid sequencing on a chip using combination of cleavable fluorescent dideoxynucleotides and 3'-O—$N_3$-modified nucleotides. (FIG. 21B) The scanned 4-color fluorescence images (shown here in grayscale) for each step of Sanger/SBS hybrid sequencing on a chip: (1) incorporation of 3'-O—$N_3$-dCTP and ddATP-$N_3$-Bodipy-FL-510; (2) cleavage of $N_3$-Bodipy-FL-510 and 3'-$CH_2N_3$ group; (3) incorporation of 3'-O—$N_3$-dATP and ddATP-$N_3$—ROX; (4) cleavage of $N_3$—ROX and 3'-$CH_2N_3$ group; (5) incorporation of 3'-O—$N_3$-dTTP and ddUTP-$N_3$-R6G; (6) cleavage of $N_3$-R6G and 3'-$CH_2N_3$ group; (7) incorporation of 3'-O—$N_3$-dGTP and ddGTP-$N_3$-Cy5 and; (8) cleavage of $N_3$-dGTP and 3'-$CH_2N_3$ group; images (9) to (63) are similarly produced. (FIG. 21C) A plot (4-color sequencing data) of raw fluorescence emission intensity obtained by using 3'-O—$N_3$-dNTPs and $N_3$-fluorophores. The small groups of peaks between the identified bases are fluorescent background from the DNA chip.

FIG. 24. Structures of the nucleotide reversible terminators

FIG. 25. Structures of cleavable fluorescent dideoxynucleotide terminators

FIG. 32. Structures of the nucleotide reversible terminators, 3'-O—$N_3$-dATP, 3'-O—$N_3$-dCTP, 3'-O—$N_3$-dGTP, 3'-O—$N_3$-dTTP FIG. 33. Structures of cleavable fluorescent dideoxynucleotide terminators ddNTP-$N_3$-fluorophores, with the 4 fluorophores having distinct fluorescent emissions: ddCTP-$N_3$-Bodipy-FL-510 ($\lambda_{abs\ (max)}$=502 nm; $\lambda_{em\ (max)}$=510 nm), ddUTP-$N_3$-R6G ($\lambda_{abs\ (max)}$=525 nm; $\lambda_{em\ (max)}$=550 nm), ddATP-$N_3$—ROX ($\lambda_{abs\ (max)}$=585 nm; $\lambda_{em\ (max)}$=602 nm), and ddGTP-$N_3$-Cy5 ($\lambda_{abs\ (max)}$=649 nm; $\lambda_{em\ (max)}$=670 nm).

FIGS. 34A-B. (FIG. 34A) Staudinger reaction with TCEP to regenerate the 3'-OH group of the DNA extension product. (FIG. 34B) Staudinger reaction with TCEP to cleave the $N_3$-fluorophore from the dideoxynucleotide.

FIG. 38. Structure of 3'-O—$N_3$-dNTPs-$N_3$-fluorophore

(FIG. 39A) A SBS with C—F—NRTs scheme for four-color sequencing on a chip by using four 3'-O—$N_3$-dNTPs-$N_3$-fluorophore and 3'-O—$N_3$-dNTPs with ddNTPs capping. (FIG. 39B) Four-color fluorescence images for each step of the SBS: (1) incorporation of 3'-O—$N_3$-dCTP-$N_3$-Bodipy-Fl-510 and 3'-O—$N_3$-dCTP; (2) cleavage of $N_3$-Bodipy-Fl-510 and 3'-$CH_2N_3$ group; (3) incorporation of 3'-O—$N_3$-dATP-$N_3$-Rox and 3'-O—$N_3$-dATP; (4) cleavage of $N_3$-Rox and 3'-$CH_2N_3$ group; images 5-47 were produced similarly. (FIG. 39C) A plot (four-color sequencing data) of raw fluorescence emission intensity obtained by using 3'-O—$N_3$-dNTPs-$N_3$-fluorophore and 3'-O—$N_3$-dNTPs. The small groups of peaks between the identified bases are fluorescent background from the DNA chip.

DETAILED DESCRIPTION OF THE INVENTION

Terms

Figure 1:
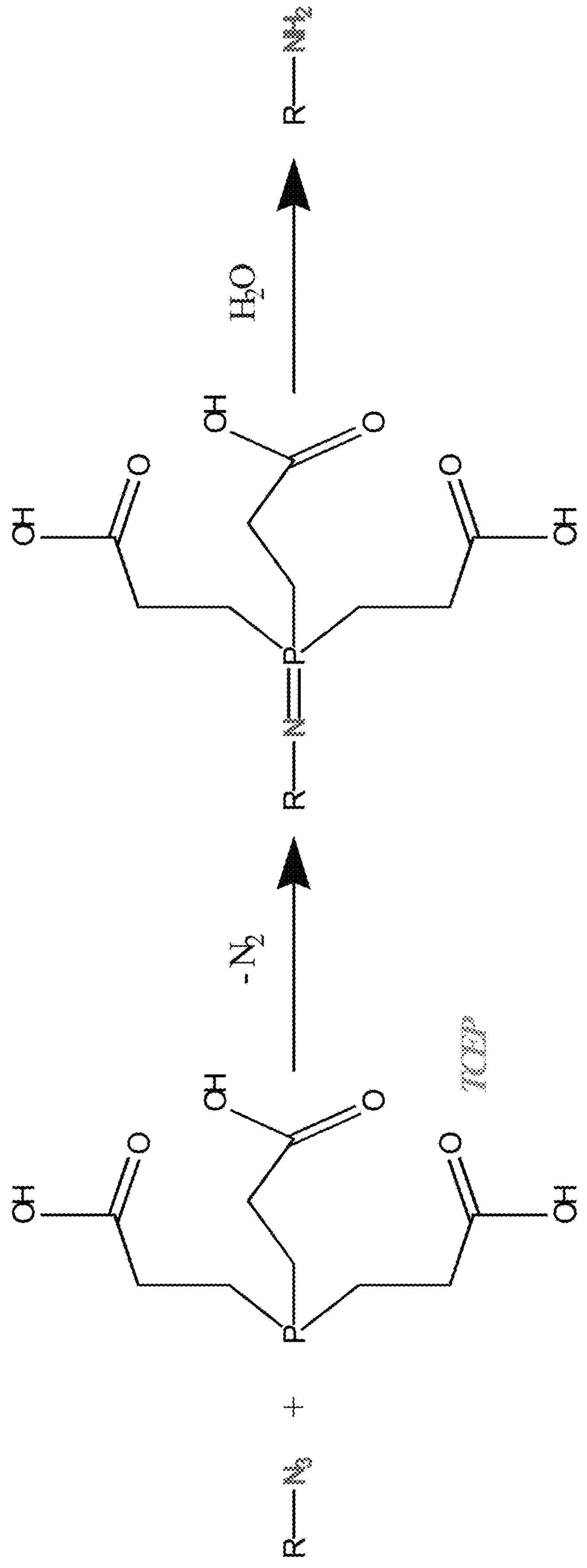
FIG. 1. Staudinger reduction with TCEP.

As used herein, and unless stated otherwise, each of the following terms shall have the definition set forth below.

A—Adenine;
C—Cytosine;
DNA—Deoxyribonucleic acid;
G—Guanine;
RNA—Ribonucleic acid;
T—Thymine; and
U—Uracil.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, New Jersey, USA).

"Type" of nucleotide refers to A, G, C, T or U. "Type" of base refers to adenine, guanine, cytosine, uracil or thymine.

"Mass tag" shall mean a molecular entity of a predetermined size which is capable of being attached by a cleavable bond to another entity.

"Solid substrate" shall mean any suitable medium present in the solid phase to which a nucleic acid or an agent may be affixed. Non-limiting examples include chips, beads and columns.

"Hybridize" shall mean the annealing of one single-stranded nucleic acid to another nucleic acid based on sequence complementarity. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.)

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Embodiments of the Invention

A composition is provided having a first, second and third portion wherein the second portion has the following structure:

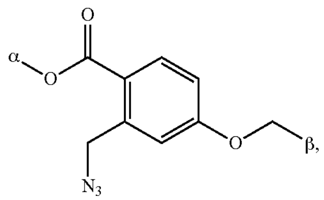

wherein α represents a point of attachment to the first portion and β represents a point of attachment to the third portion.

α may be directly linked to the first portion, e.g. comprising a base, or bonded to the, for example base via, e.g. an alkynylene. β may be directly linked to the third portion, e.g. a detectable marker, or bonded to the third portion, for example via another group.

In an embodiment the first portion is a deoxynucleotide or a dideoxynucleotide and the third portion is a detectable marker. In an embodiment the detectable marker is a fluorescent dye. In an embodiment the deoxynucleotide or dideoxynucleotide comprises a methylazido group attached to a 3' O atom thereof.

In an embodiment the composition has the structure:

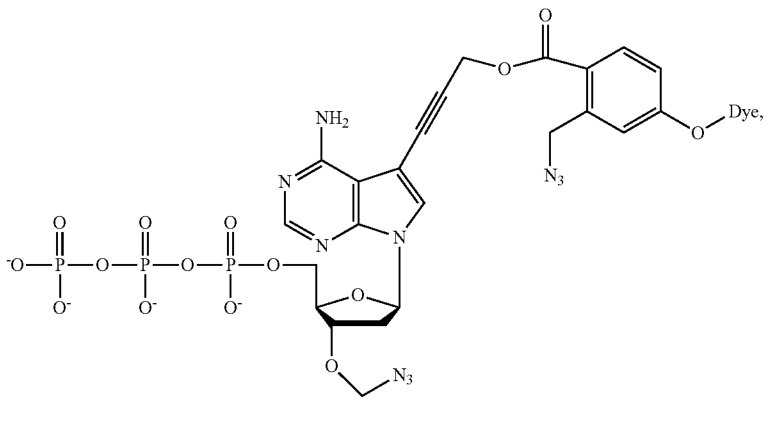

-continued
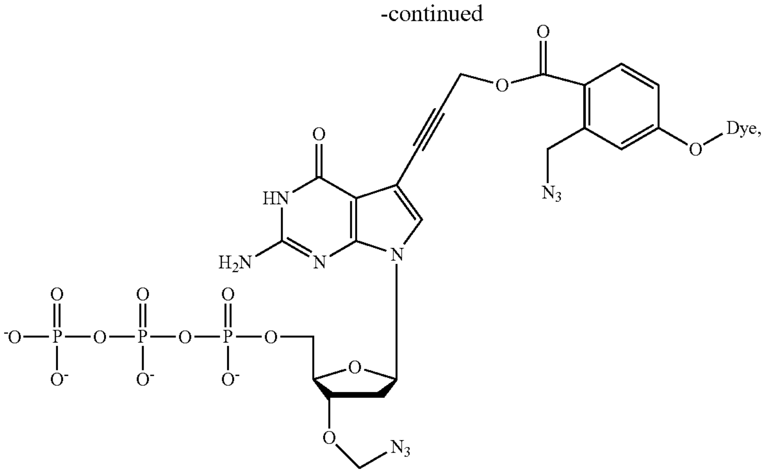
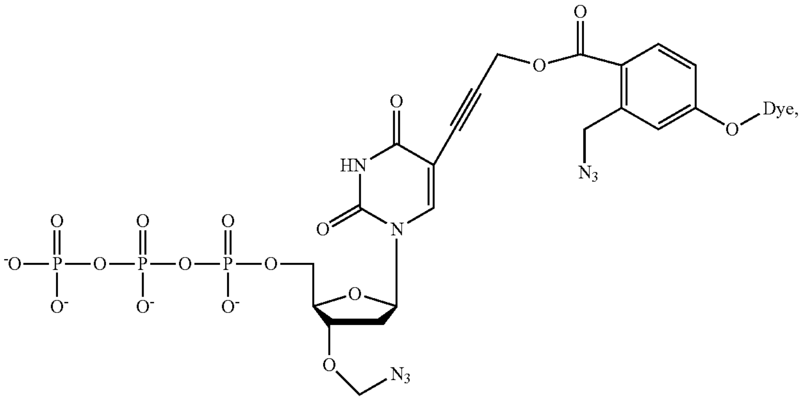
or
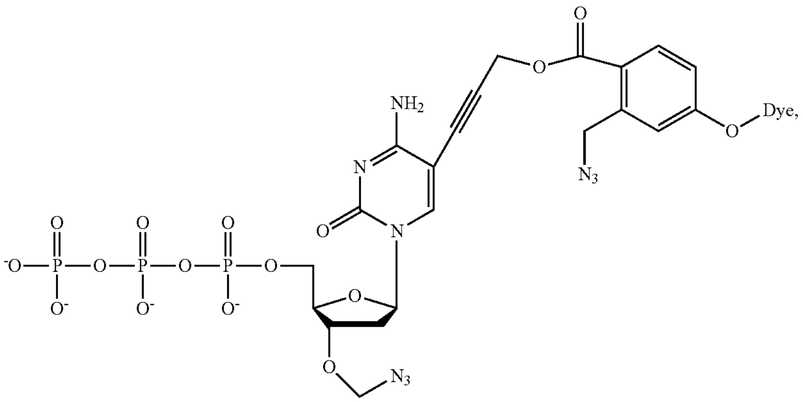
wherein the dye in each structure is a fluorescent dye In an embodiment the composition has the structure:
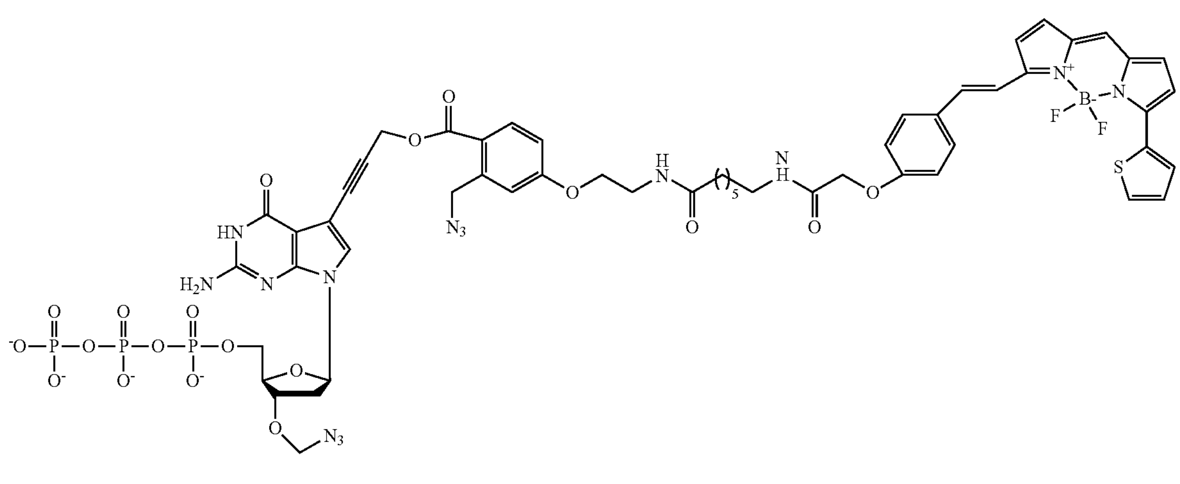
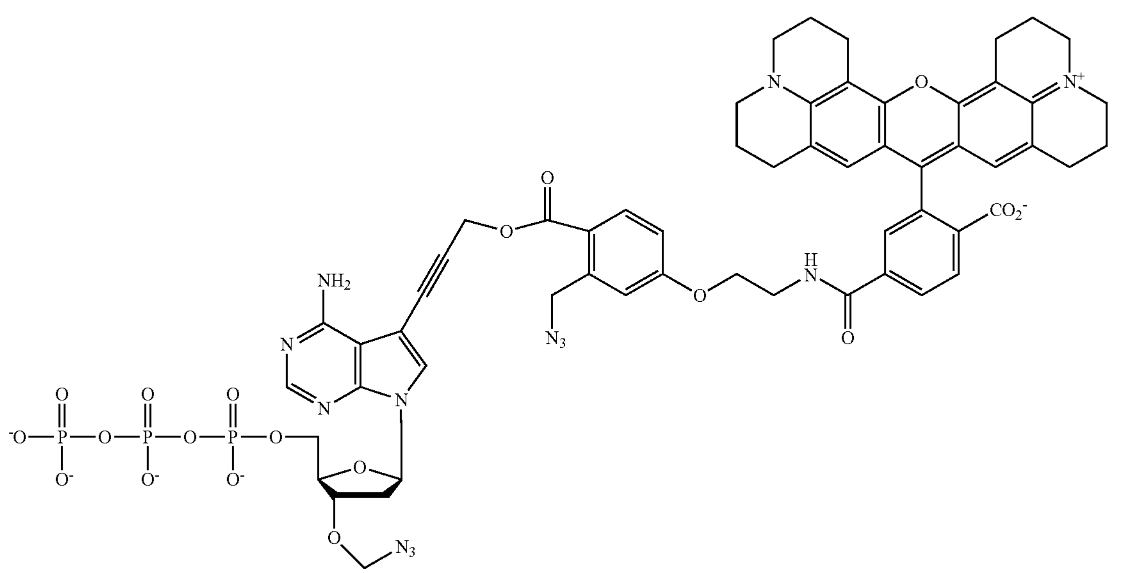
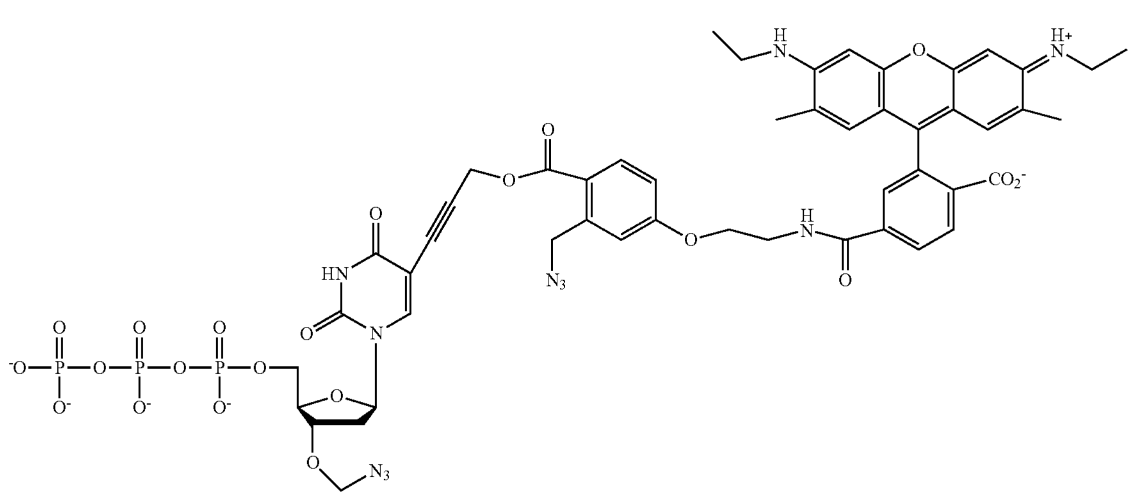
or -continued

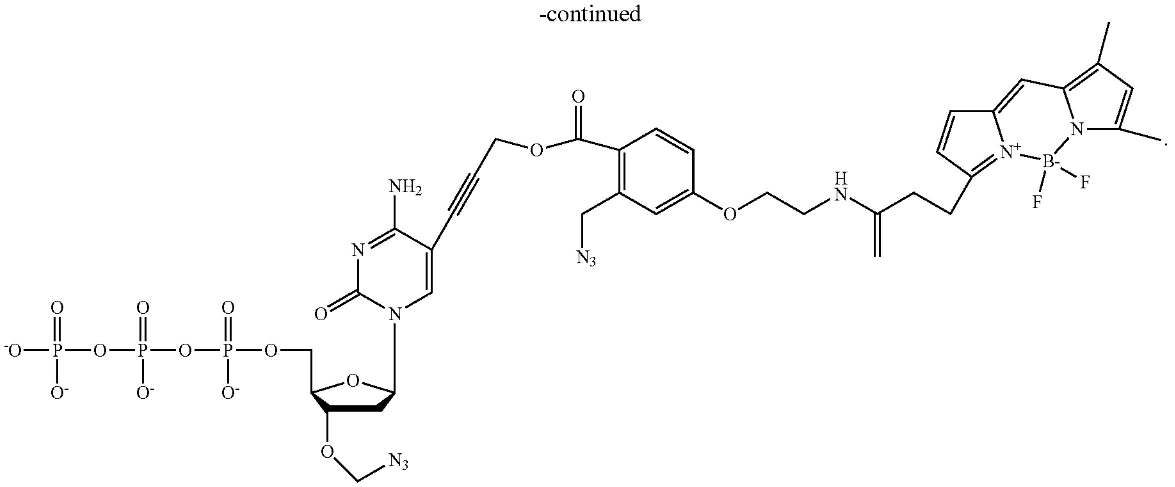

A method is provided for determining the identity of each of a series of consecutive nucleotide residues in a nucleic acid comprising:

a) contacting the nucleic acid with (i) at least four different deoxynucleotide triphosphate (dNTP) analogues, each having the structure:

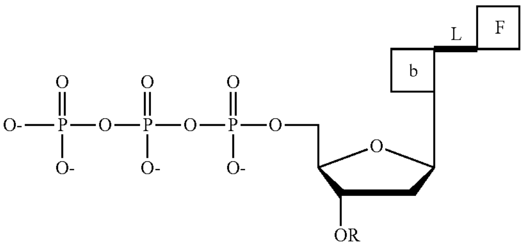

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

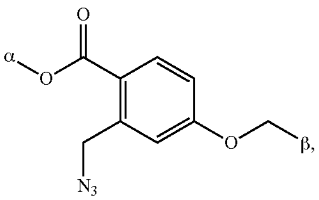

wherein α represents a point of attachment to the base and β represents a point of attachment to the fluorophore, and wherein R is a cleavable chemical group, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method is provided for determining the identity of each of a series of consecutive nucleotide residues in a self-priming nucleic acid comprising:

a) contacting the self-priming nucleic acid with (i) at least four different deoxynucleotide triphosphate (dNTP) analogues, each having the structure:

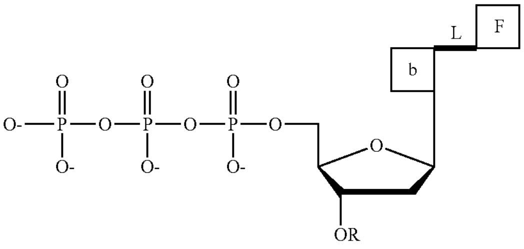

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

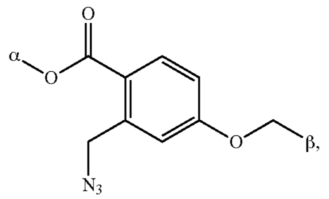

wherein α represents a point of attachment to the base and β represents a point of attachment to the fluorophore, and wherein R is a cleavable chemical group, and (ii) a nucleic acid polymerase, under conditions permitting (a) the self-priming nucleic acid to prime itself and (b) one of the four dNTP analogues that is complementary to the consecutive nucleotide residue to be identified to form a phosphodiester bond with the 3' end of the self-priming nucleic acid primer and thereby extend the self-priming nucleic acid;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the self-priming nucleic acid.

In an embodiment of the instant methods, steps b) and c) can be performed simultaneously, or in the order step b) then step c) or in the order step c) then step b). In an embodiment of the instant methods, the nucleic acid is DNA and the nucleic acid polymerase is a 9°N thermopolymerase. In an embodiment of the instant methods, the cleavable chemical group is a methylazido group. In an embodiment of the instant methods, the four dNTP analogues have the following structures:

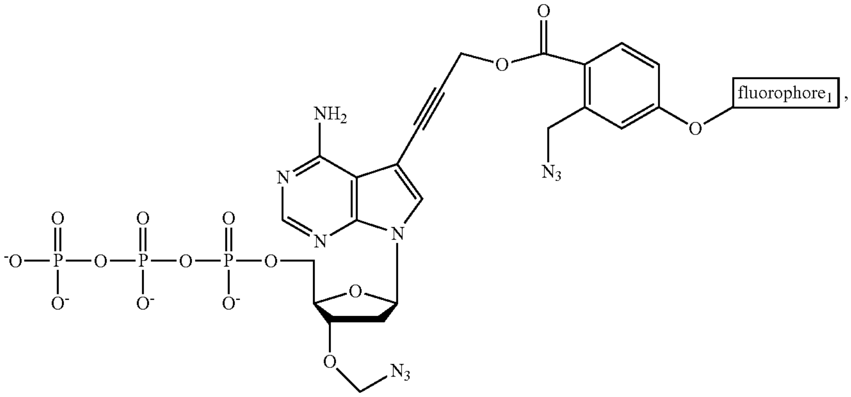

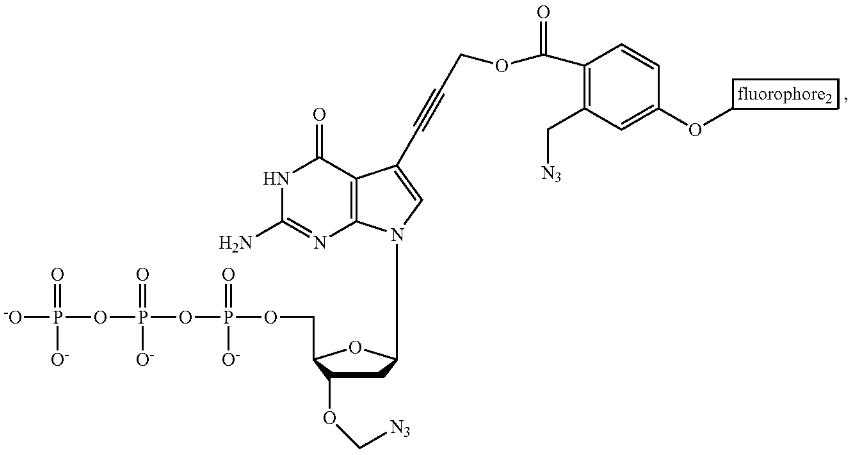

-continued
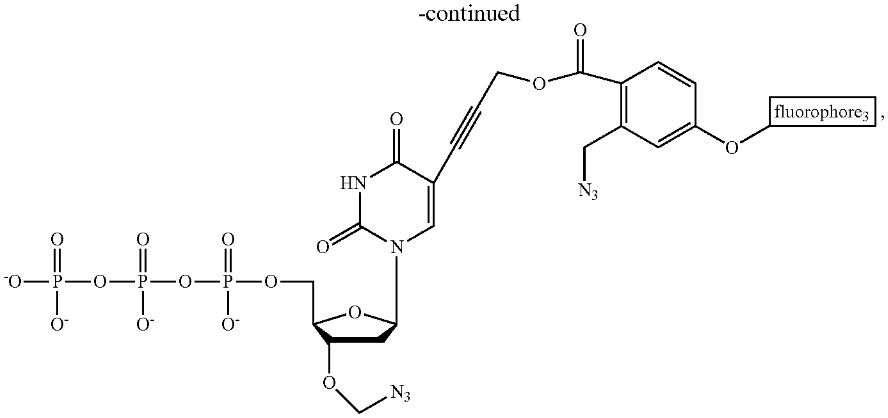
, and
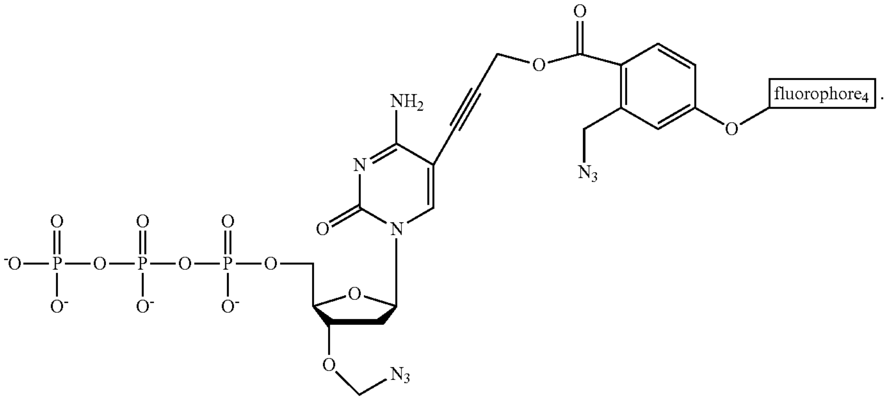
.
In an embodiment the four dNTP analogues have the following structures:
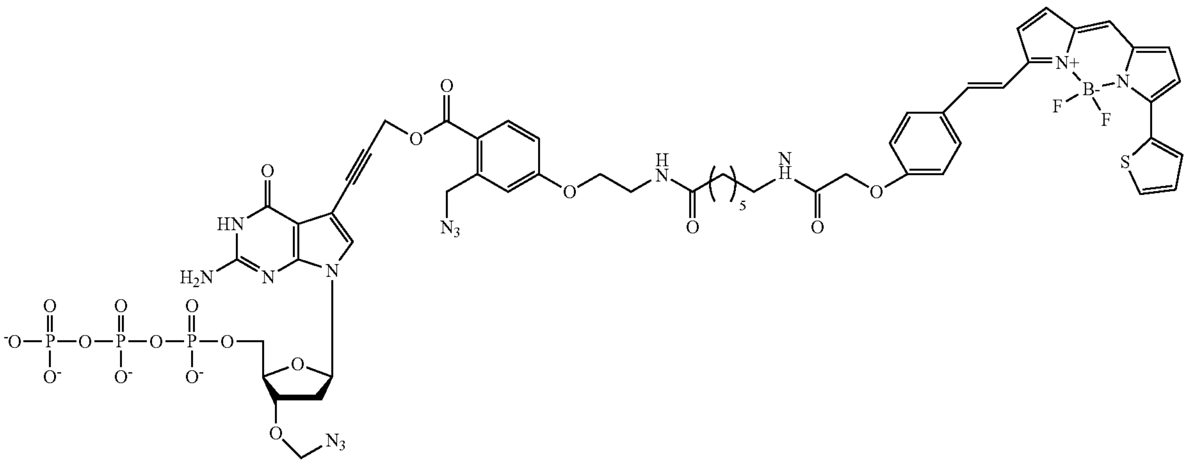

-continued
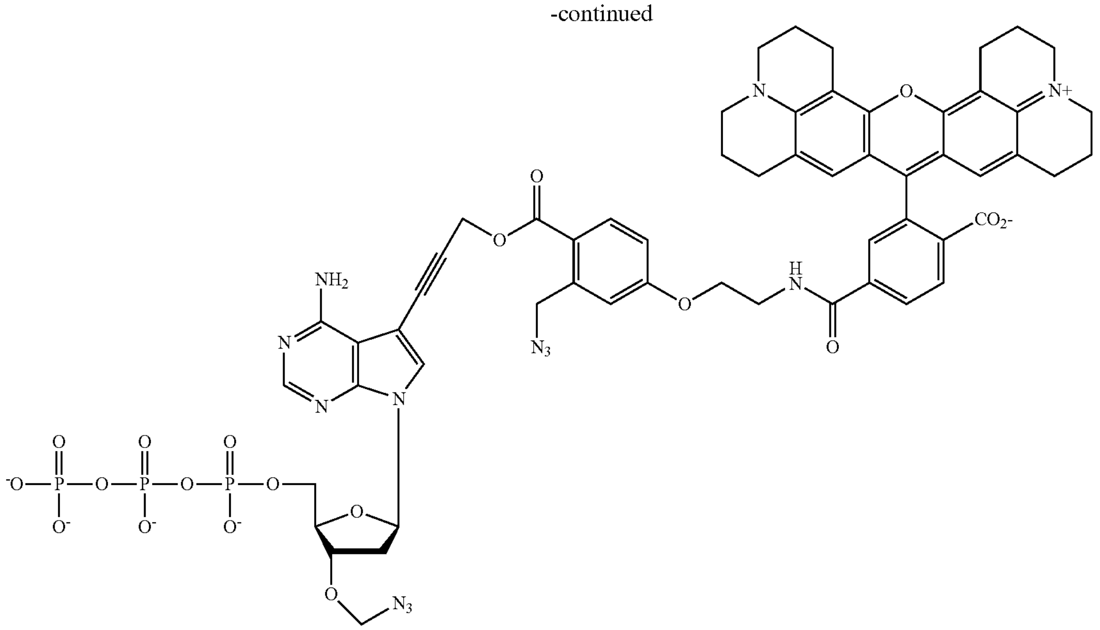
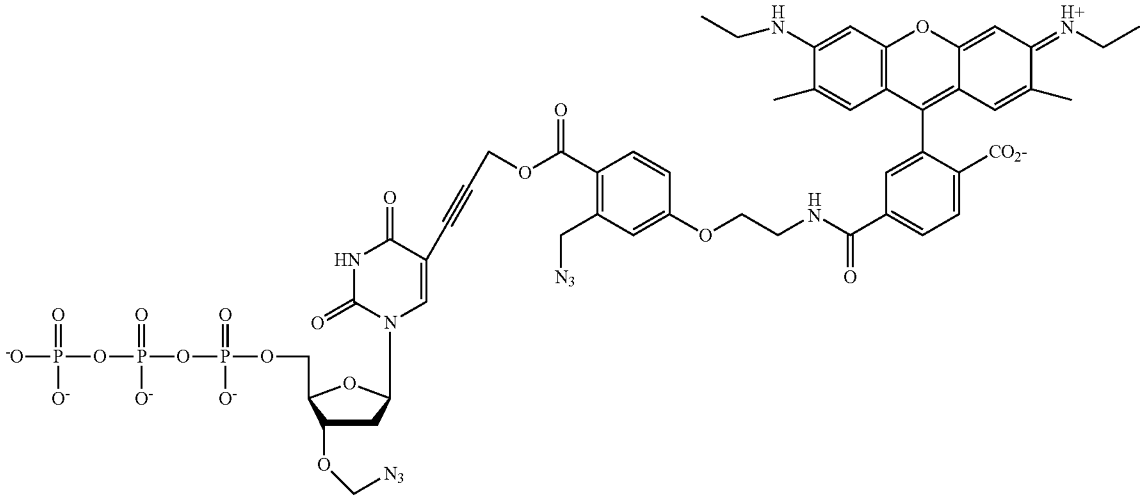
and
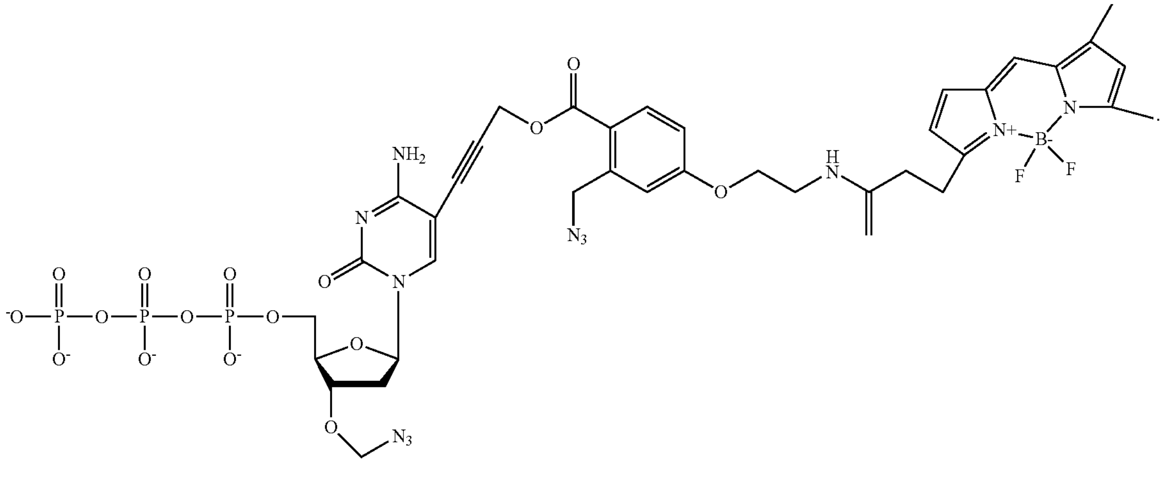
In an embodiment up to 1000 consecutive nucleotides are identified. In an embodiment up to $1\times10^4$ consecutive nucleotides are identified. In an embodiment up to $1\times10^6$ consecutive nucleotides are identified. In an embodiment the nucleic acid is immobilized on a solid surface. In an embodiment the solid surface is a chip or a bead.

A kit is provided for use in sequencing a nucleic acid comprising:
a) a plurality of four nucleotide analogues having the structure:
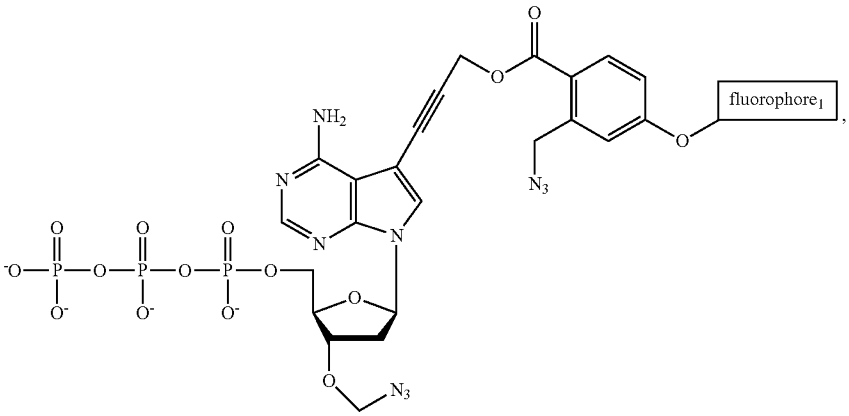
,
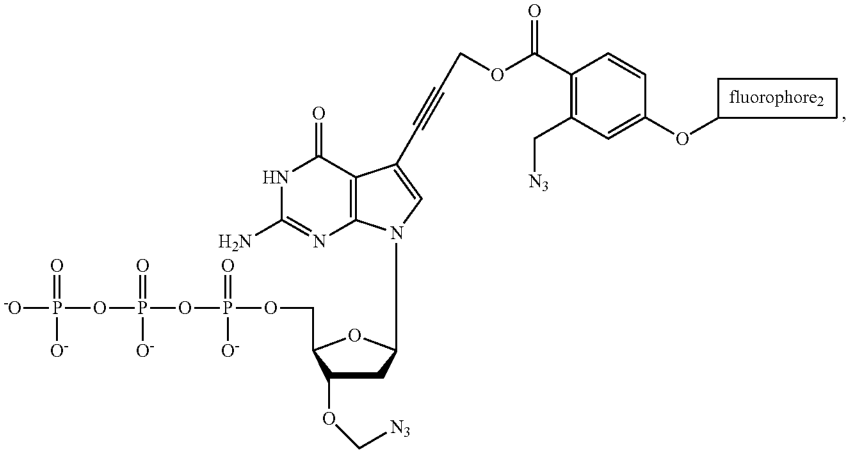
,
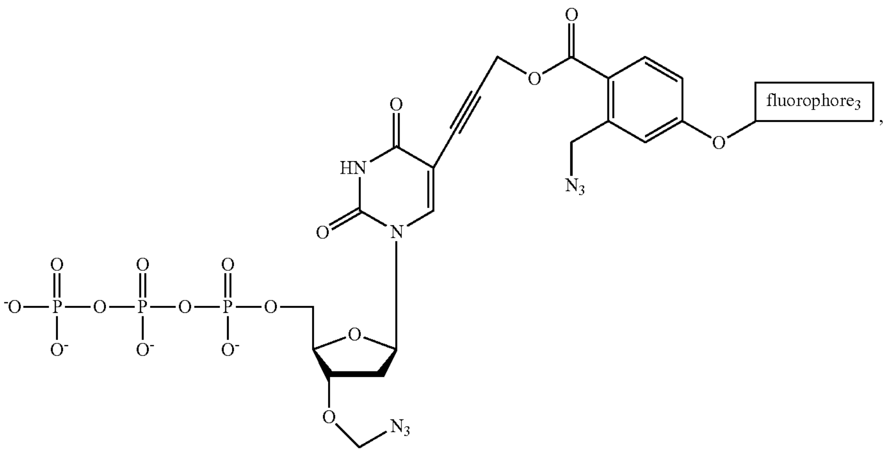
, and -continued
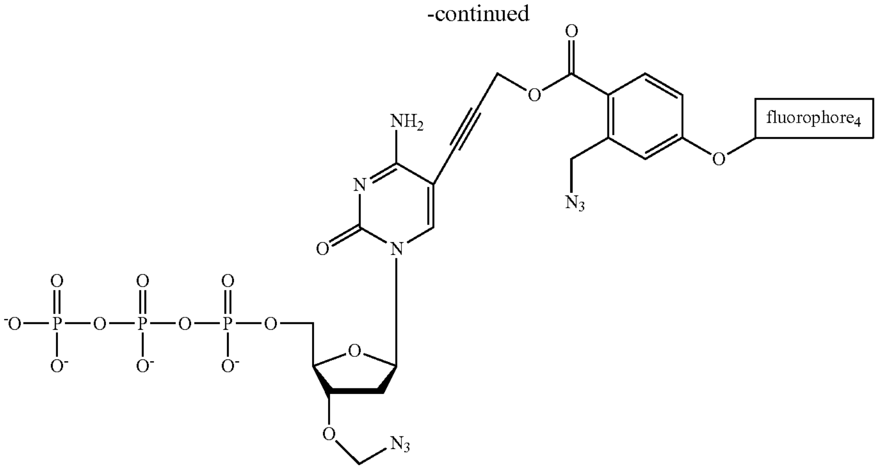
and
(b) instructions for use.
In an embodiment four nucleotide analogues having the following structures:
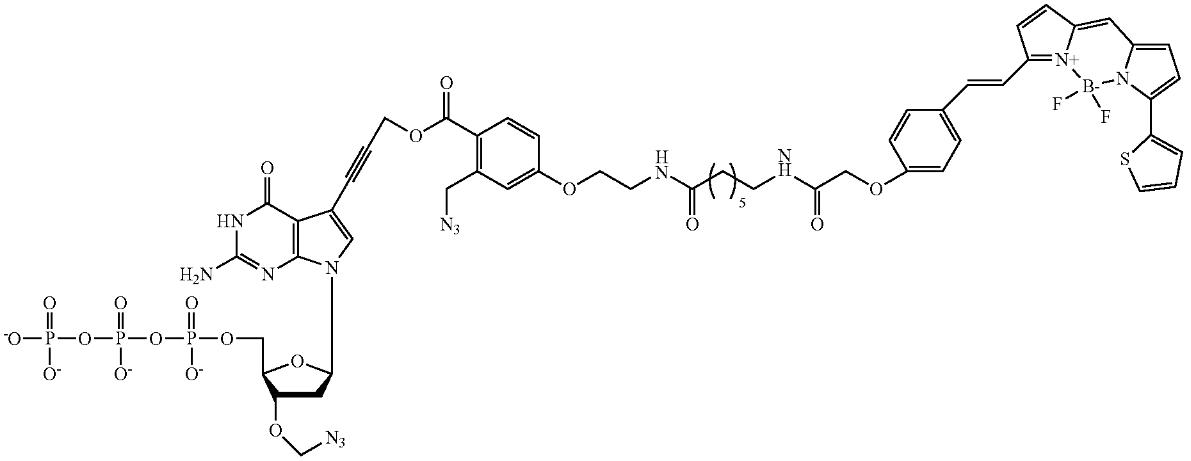
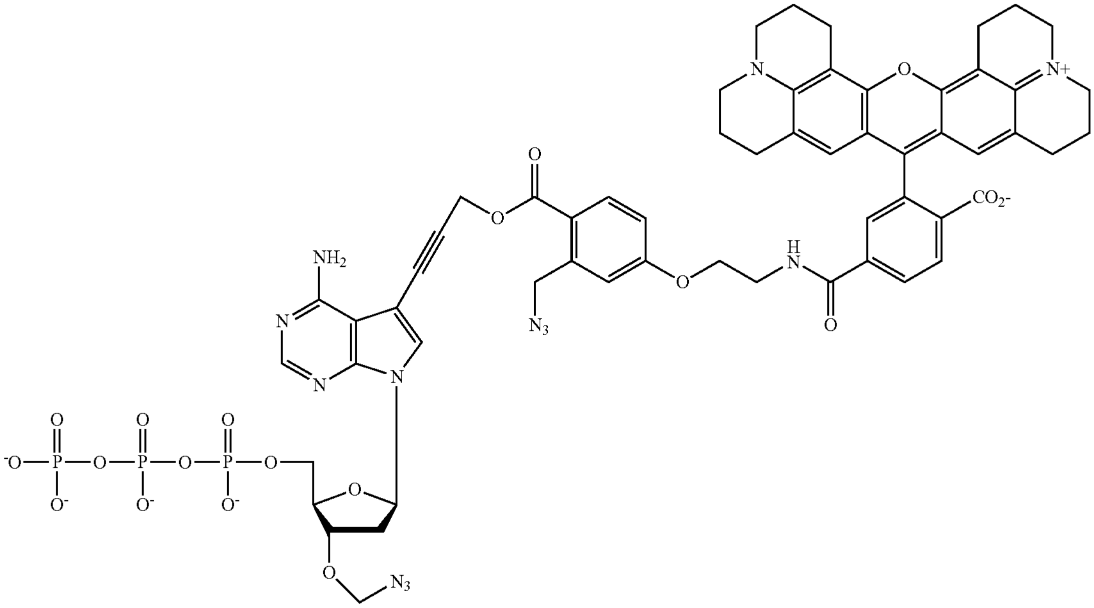

-continued

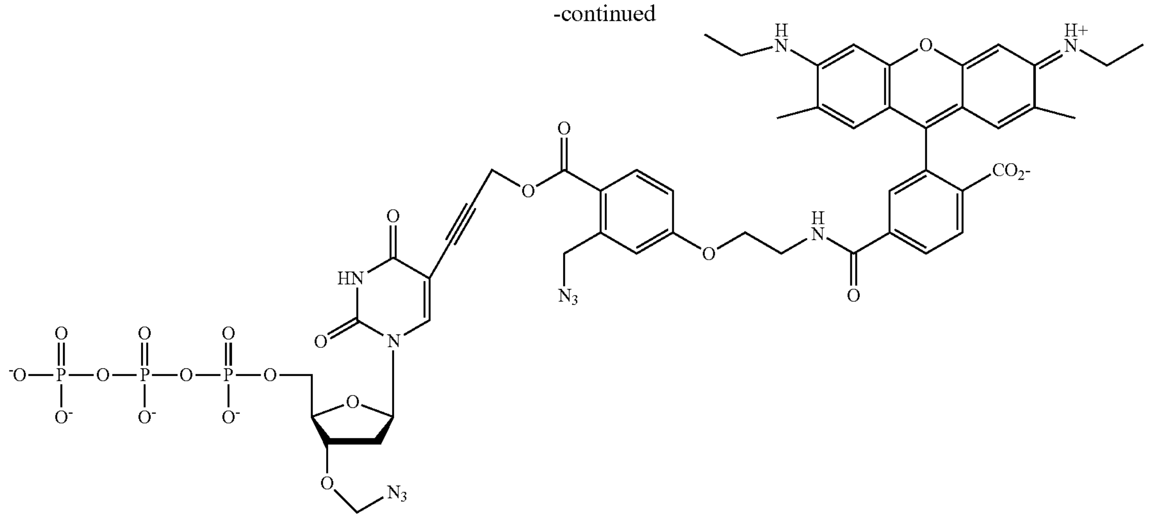

and

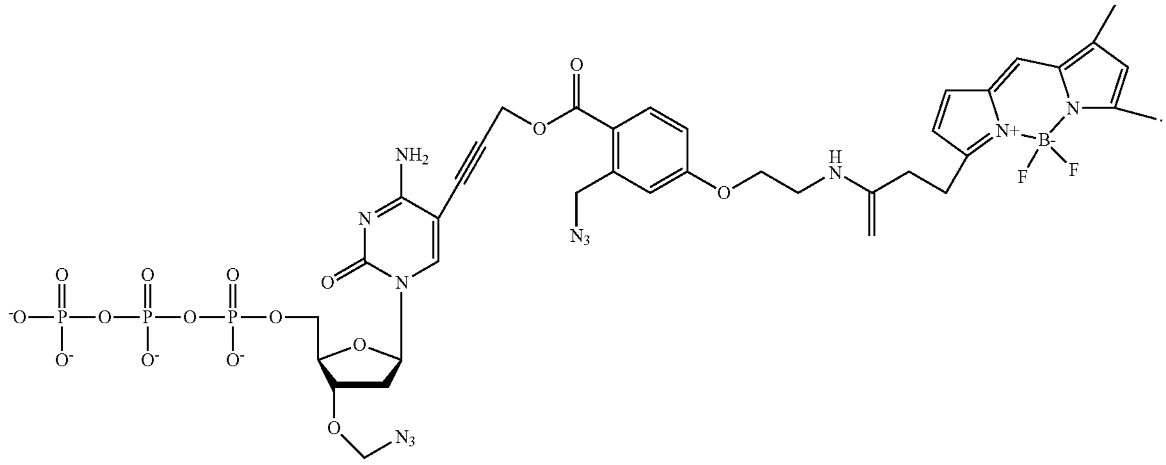

An array is provided comprising a nucleic acid attached to a solid surface, wherein the nucleic acid comprises an azidomethyl group attached to a 3' O atom thereof and a molecule having the structure:

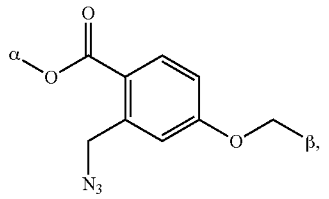

wherein α represents a point of attachment to a 3' base of the nucleic acid and β represents a point of attachment to a detectable marker.

An array is provided comprising a self-priming nucleic acid attached to a solid surface, wherein the nucleic acid comprises an azidomethyl group attached to a 3' O atom thereof and a molecule having the structure:

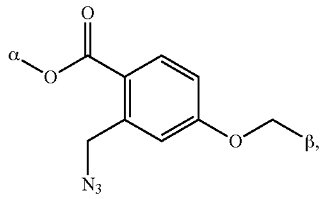

wherein α represents a point of attachment to a 3' base of the nucleic acid and β represents a point of attachment to a detectable marker.

In embodiment the detectable marker is a fluorophore.

A method is provided for increasing a read length of DNA sequencing by synthesis comprising (a) providing deoxynucleotide triphosphate analogues wherein the deoxynucleotide triphosphate analogues differ from deoxynucleotide triphosphates by having a methylazido group attached to a 3' O atom thereof and by having a detectable marker attached to a 1 nitrogen or a 9 nitrogen of a base thereof through a linker comprising the structure

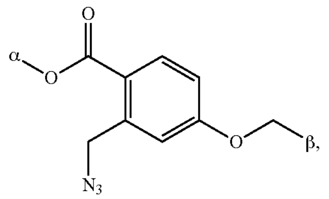

wherein α represents a point of attachment to a the base and β represents a point of attachment to the detectable marker, (b) incorporating a plurality of the deoxynucleotide triphosphate analogues into a nucleic acid being synthesized in the DNA sequencing by synthesis, and (c) cleaving the methylazido and detectable marker from each dNTP analogue, so as to thereby increase the read length of the DNA sequence by synthesis.

A method for determining the identity of each of a series of consecutive nucleotide residues in a nucleic acid comprising:

a) contacting the nucleic acid with (i) at least four different deoxynucleotide triphosphate (dNTP) analogues, each having the structure:

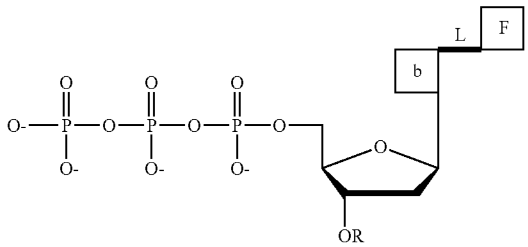

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

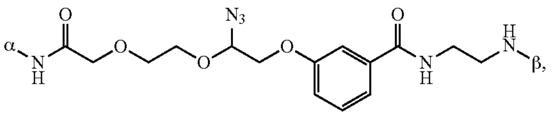

wherein α represents a point of attachment to the base and β represents a point of attachment to the fluorophore, and wherein R is a cleavable chemical group, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method for determining the identity of each of a series of consecutive nucleotide residues in a self-priming nucleic acid comprising:

a) contacting the self-priming nucleic acid with (i) at least four different deoxynucleotide triphosphate (dNTP) analogues, each having the structure:

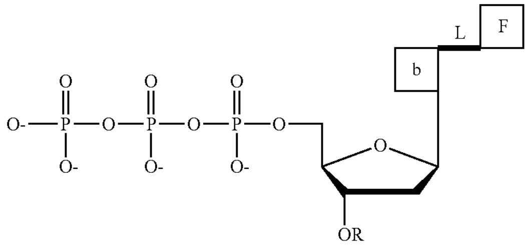

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

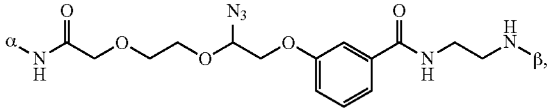

wherein α represents a point of attachment to the base and β represents a point of attachment to the fluorophore, and wherein R is a cleavable chemical group, and (ii) a nucleic acid polymerase, under conditions permitting (a) the self-priming nucleic acid to prime itself and (b) one of the four dNTP analogues that is complementary to the consecutive nucleotide residue to be identified to form a phosphodiester bond with the 3' end of the self-priming nucleic acid primer and thereby extend the self-priming nucleic acid;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the self-priming nucleic acid.

In an embodiment of the instant methods, steps b) and c) can be performed simultaneously, or in the order step b) then step c) or in the order step c) then step b). In an embodiment of the instant methods, the nucleic acid is DNA and the nucleic acid polymerase is a 9°N thermopolymerase. In an embodiment of the instant methods, the cleavable chemical group is a methylazido group. In an embodiment of the instant methods, the four dNTP analogues have the following structures:

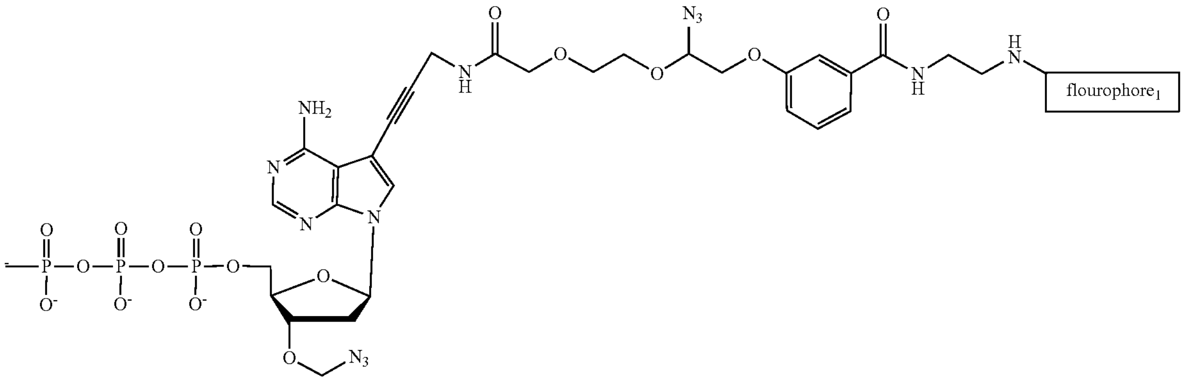

,

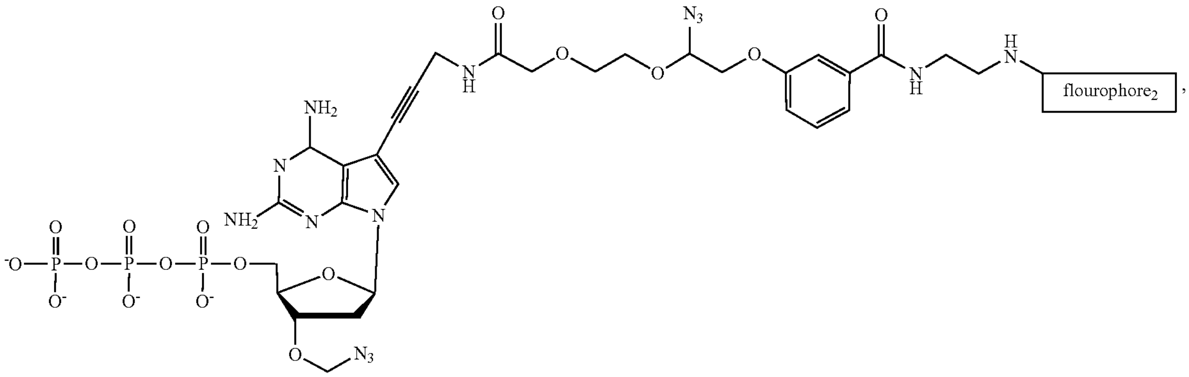

,

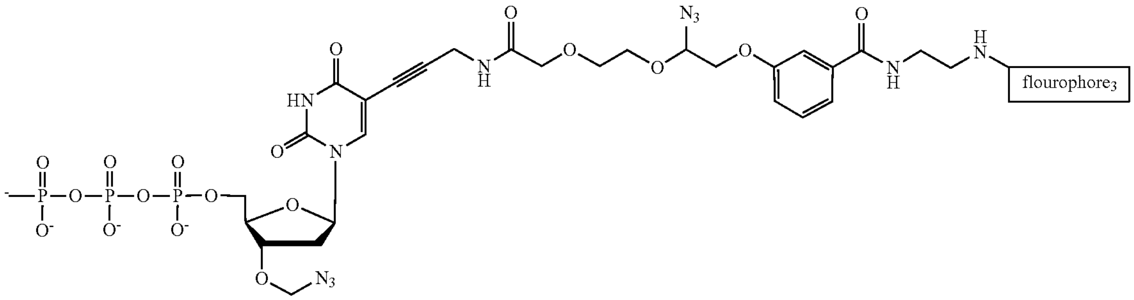

, and

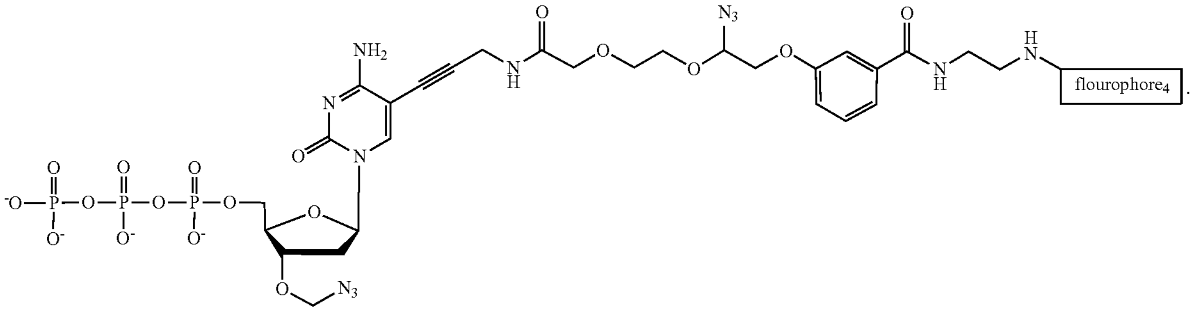

.

In an embodiment the four dNTP analogues have the following structures:
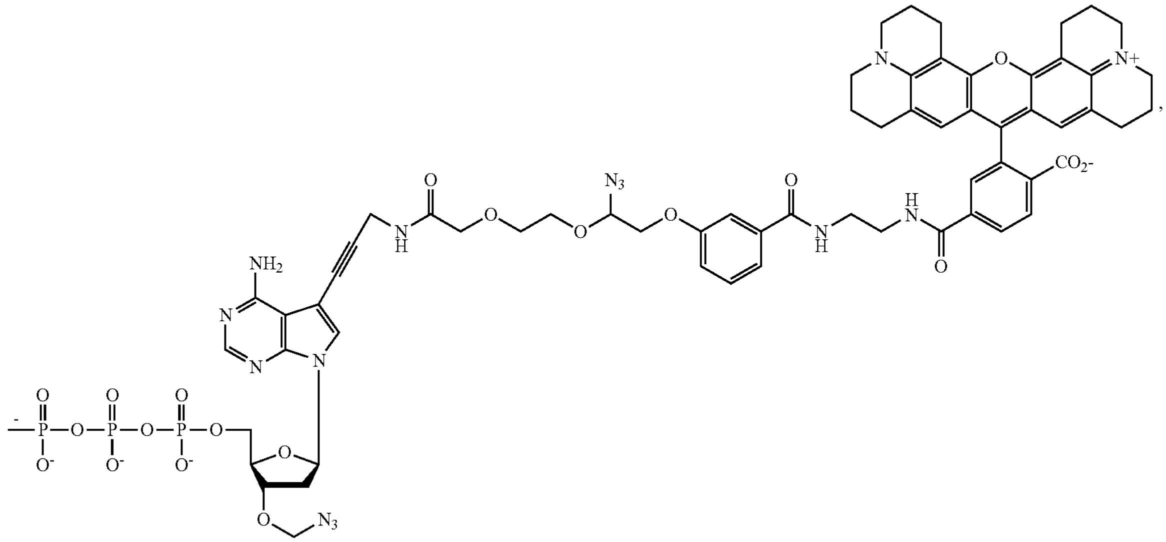
,
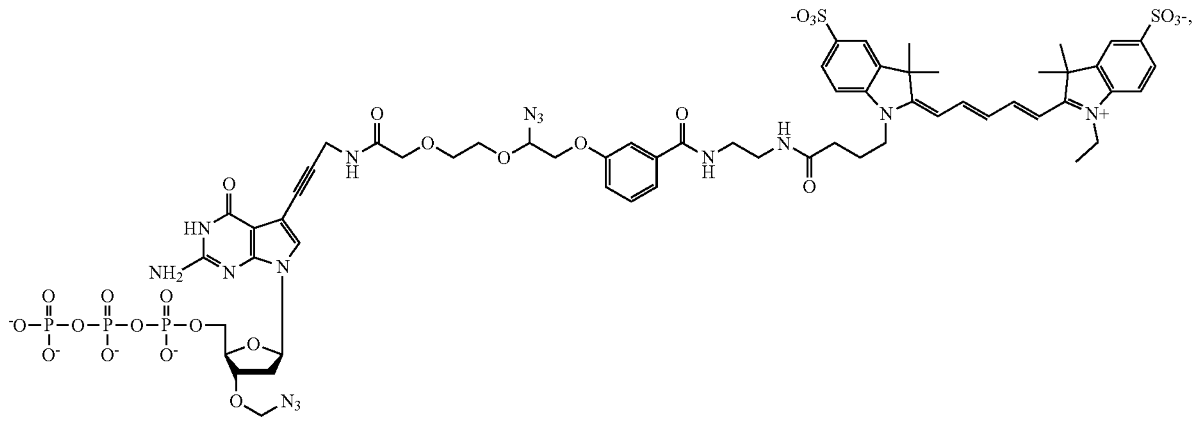
,
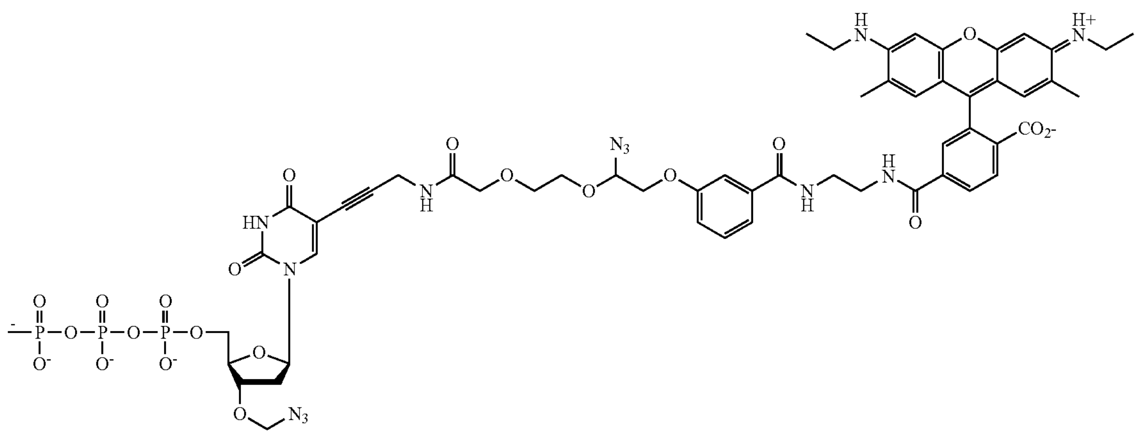
and -continued

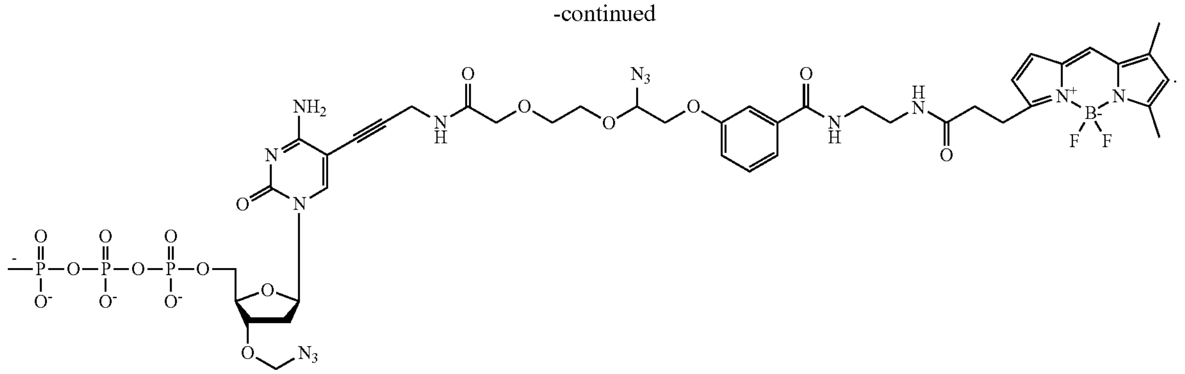

In an embodiment up to 1000 consecutive nucleotides are identified. In an embodiment up to $1\times10^4$ consecutive nucleotides are identified. In an embodiment up to $1\times10^6$ consecutive nucleotides are identified. In an embodiment the nucleic acid is immobilized on a solid surface. In an embodiment the solid surface is a chip or a bead.

A method for determining the identity of each of a series of consecutive nucleotide residues in a plurality of nucleic acids comprising, the same series of consecutive nucleotides comprising:

a) contacting the nucleic acids with (i) at least four different dideoxynucleotide triphosphate (ddNTP) analogues, each having the structure:

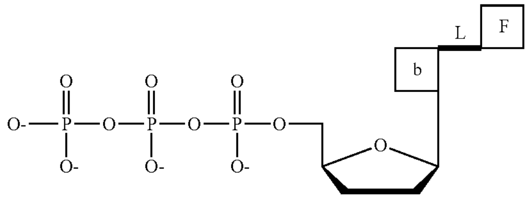

wherein F is a fluorophore, L is a cleavable linker molecule and b is a base which is adenine, guanine, cytosine, uracil or thymine, wherein the fluorophore attached through a linker to each type of base differs in its emission or excitation spectra from a fluorophore attached through a linker to each of the remaining types of bases, and each of the four ddNTP analogues differs from the remaining three ddNTP analogues by having a different base, and wherein L comprises the structure:

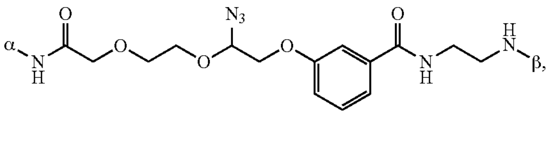

wherein α represents a point of attachment to the base of the dideoxynucleotide and β represents a point of attachment to the fluorophore, and (ii) at least four different deoxynucleotide triphosphate (dNTP) analogue, each having the structure:

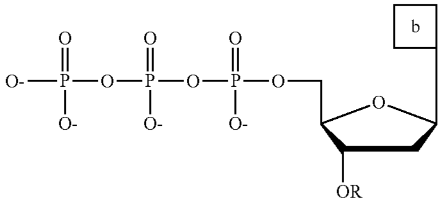

wherein b is a base which is adenine, guanine, cytosine, uracil or thymine, and each of the four dNTP analogues differs from the remaining three dNTP analogues by having a different base, and wherein R is a cleavable chemical group, (iii) a nucleic acid polymerase and (iv) at least two primers each of which hybridizes with a separate nucleic acid of the plurality of nucleic acids, under conditions permitting a ddNTP analogue that is complementary to the consecutive nucleotide residue in the nucleic acid to be identified to form a phosphodiester bond with the 3' end of one of the primers and a dNTP analogue that is complementary to the consecutive nucleotide residue to be identified to form a phosphodiester bond with the 3' end of another of the primers;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method for determining the identity of consecutive nucleotide residues in a self-priming nucleic acid comprising:

a) contacting the nucleic acids with (i) at least four different dideoxynucleotide triphosphate (ddNTP) analogues, each having the structure:

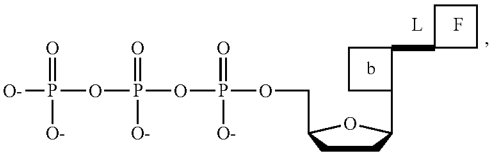

wherein F is a fluorophore, L is a cleavable linker molecule and b is a base which is adenine, guanine, cytosine, uracil or thymine, wherein the fluorophore attached through a linker to each type of base differs in its emission or excitation spectra from a fluorophore attached through a linker to each of the remaining types of bases, and each of the four ddNTP analogues differs from the remaining three ddNTP analogues by having a different base, wherein L comprises the structure:

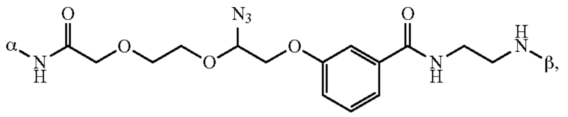

wherein α represents a point of attachment to the base of the dideoxynucleotide and β represents a point of attachment to the fluorophore, and (ii) at least four different deoxynucleotide triphosphate (dNTP) analogue, each having the structure:

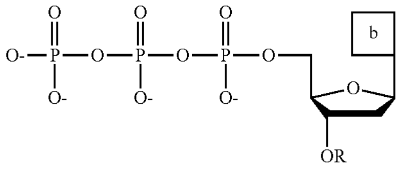

wherein b is a base which is adenine, guanine, cytosine, uracil or thymine, and each of the four dNTP analogues differs from the remaining three dNTP analogues by having a different base, and wherein R is a cleavable chemical group, (iii) a nucleic acid polymerase and (iv) at least two primers each of which hybridizes with a separate nucleic acid of the plurality of nucleic acids, under conditions permitting a ddNTP analogue that is complementary to the consecutive nucleotide residue to be identified to form a phosphodiester bond with the 3' end of one of the self-priming nucleic acids and a dNTP analogue that is complementary to the consecutive nucleotide residue to be identified to form a phosphodiester bond with the 3' end of another of the self-priming nucleic acids;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

In an embodiment of the instant methods, steps b) and c) can be performed simultaneously, or in the order step b) then step c) or in the order step c) then step b). In an embodiment of the instant methods, the nucleic acid is DNA and the nucleic acid polymerase is a 9°N thermopolymerase. In an embodiment of the instant methods, the cleavable chemical group is a methylazido group.

In an embodiment of the instant methods, the four ddNTP analogues have the following structures:

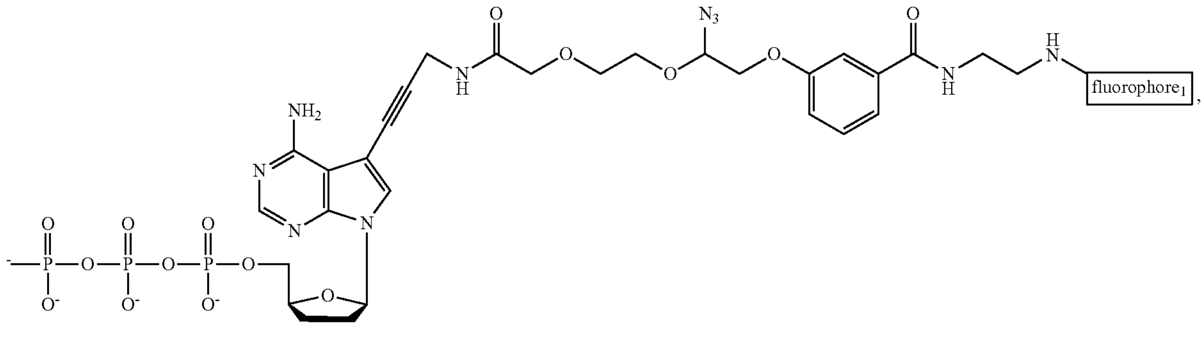

-continued
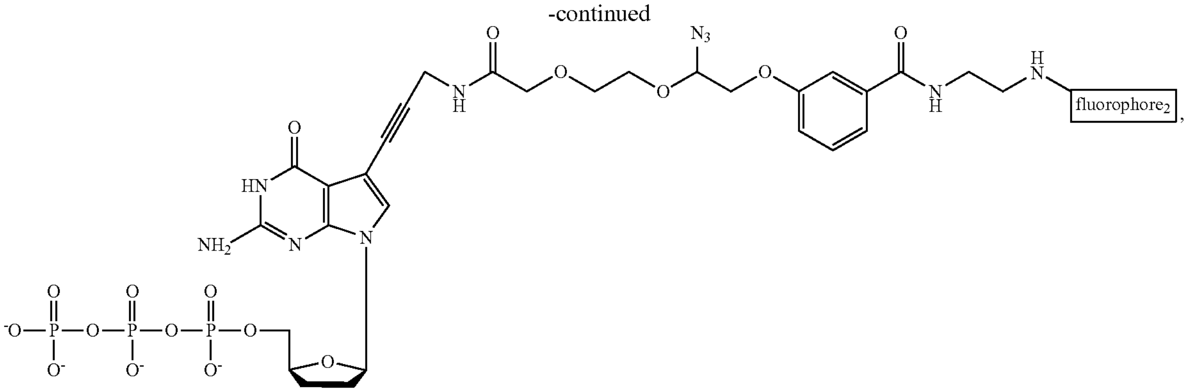
,
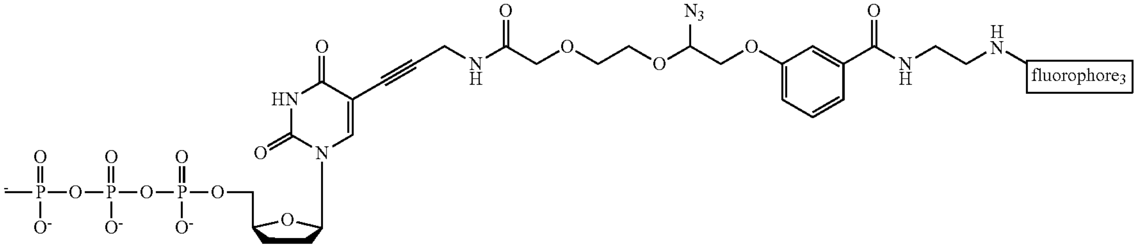
, and
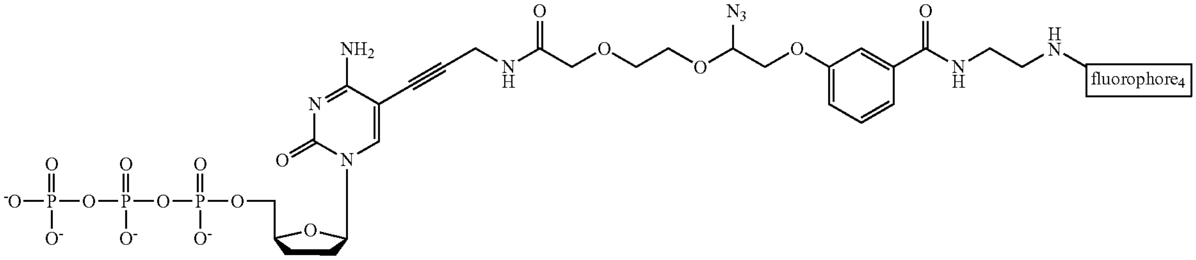
In an embodiment, the four dNTPs have the following structures:
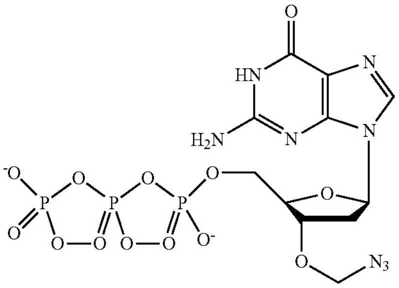
,
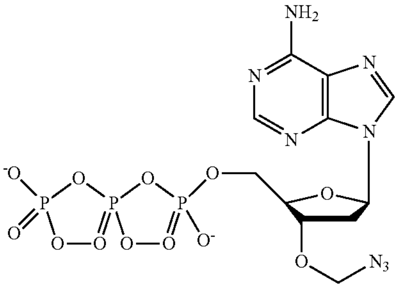
,
-continued
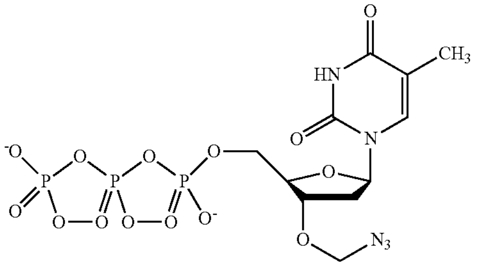
and
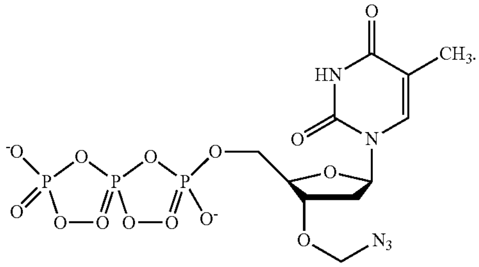
.

In an embodiment the four ddNTP analogues have the following structures:

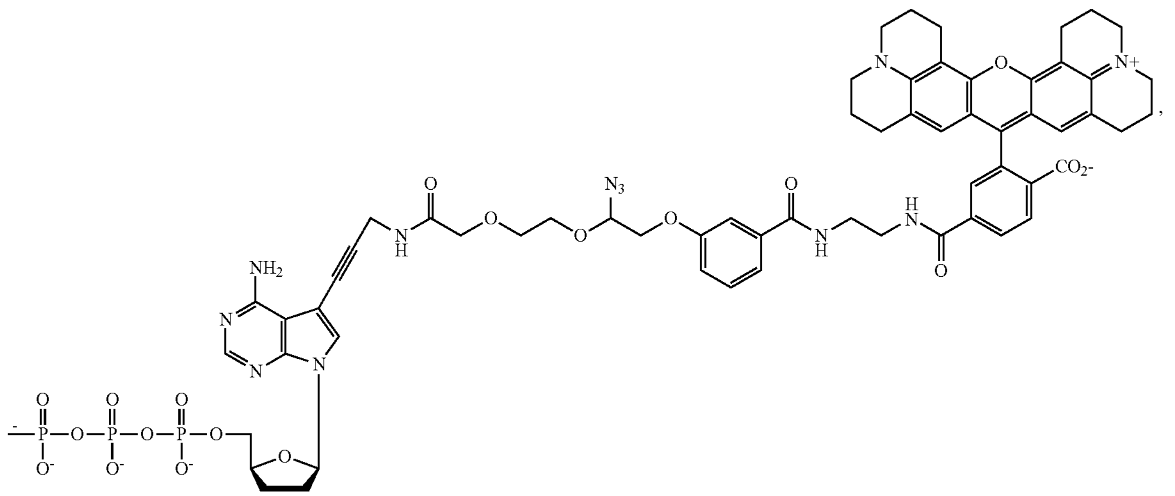

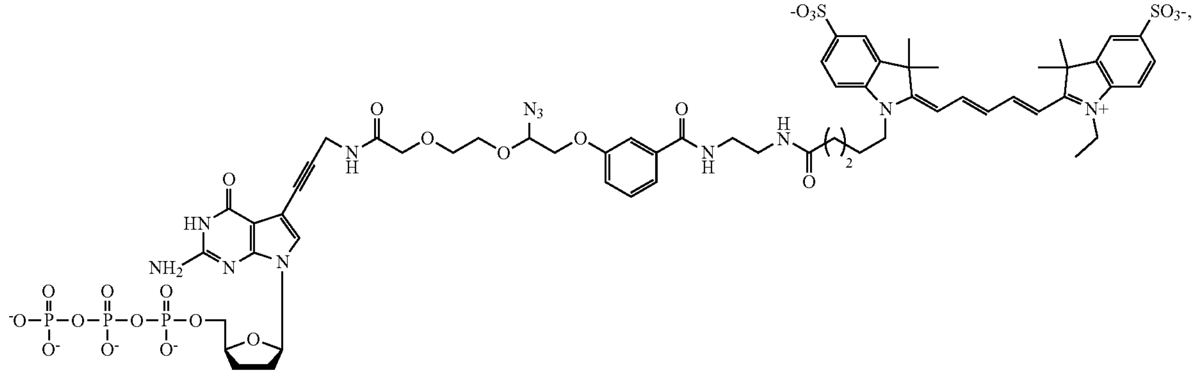

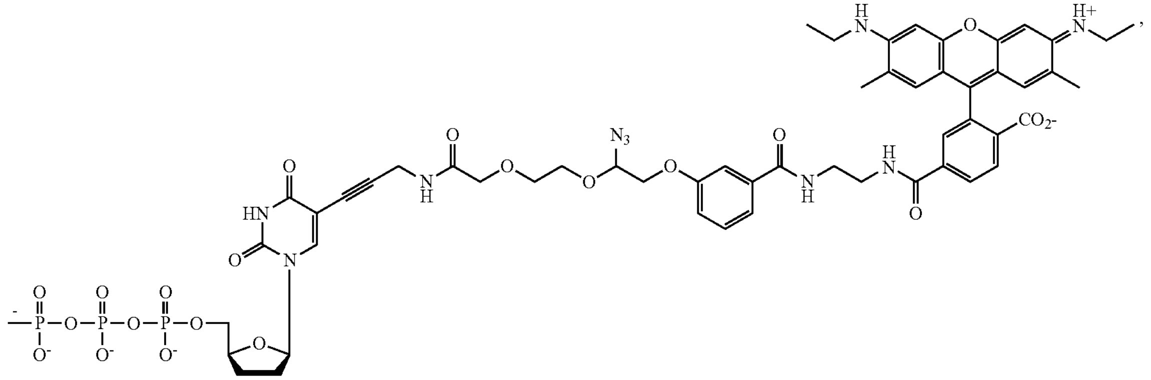

and

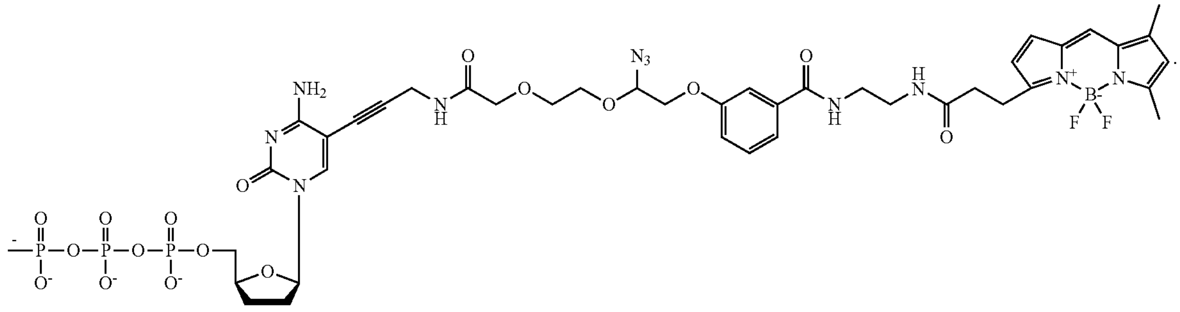

In an embodiment up to 1000 consecutive nucleotides are identified. In an embodiment up to $1\times10^4$ consecutive nucleotides are identified. In an embodiment up to $1\times10^6$ consecutive nucleotides are identified. In an embodiment the nucleic acid is immobilized on a solid surface. In an embodiment the solid surface is a chip or a bead.

A kit is provided for use in sequencing a nucleic acid comprising:
b) a plurality of four nucleotide analogues having the structure:
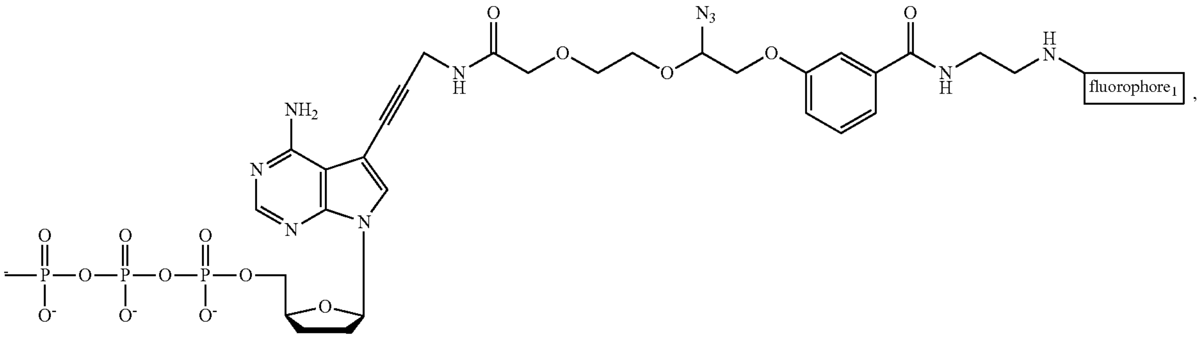
,
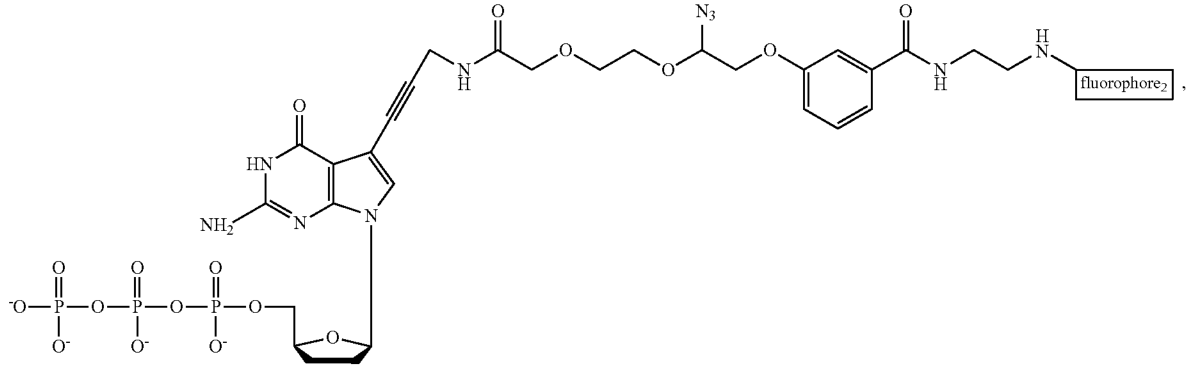
,
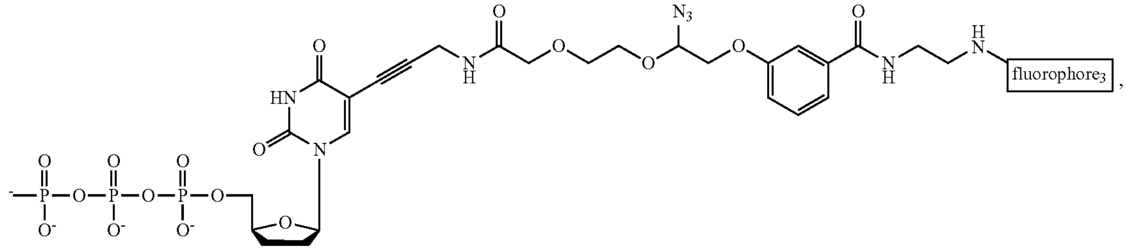
, and
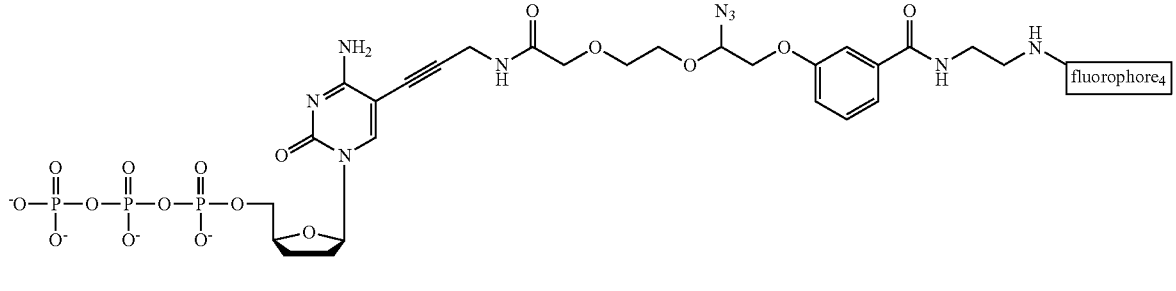

with
(b) a plurality of deoxynucleotide analogues having the structure:
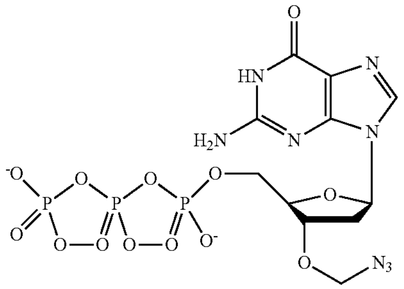
,
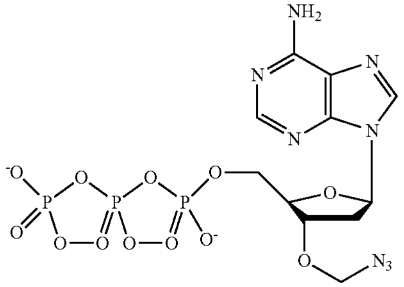
,
-continued
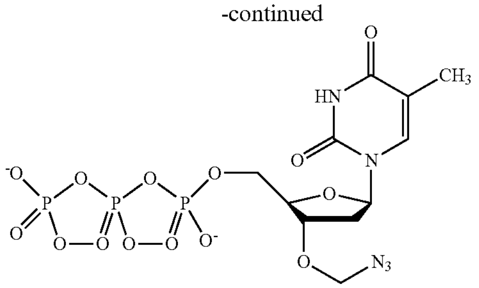
and
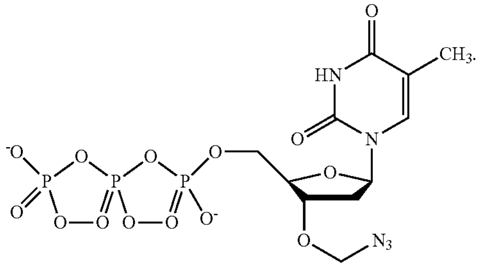
.
and
(c) instructions for use.
In an embodiment, four dideoxynucleotide analogues having the following structures:
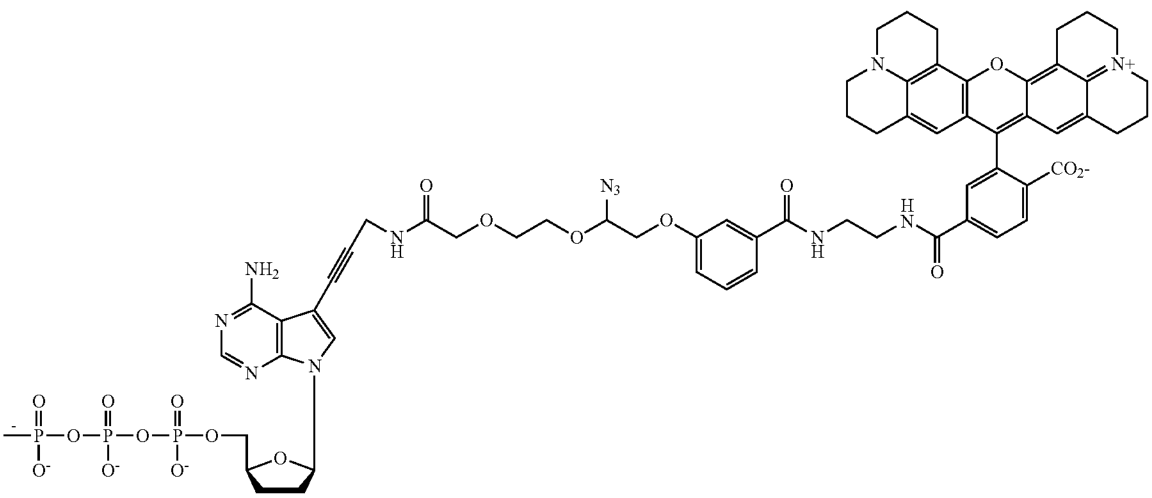
,
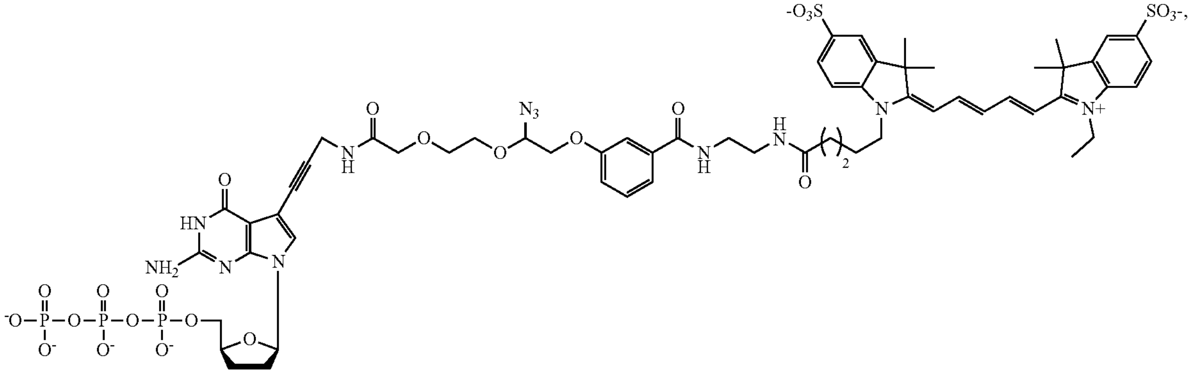
, -continued

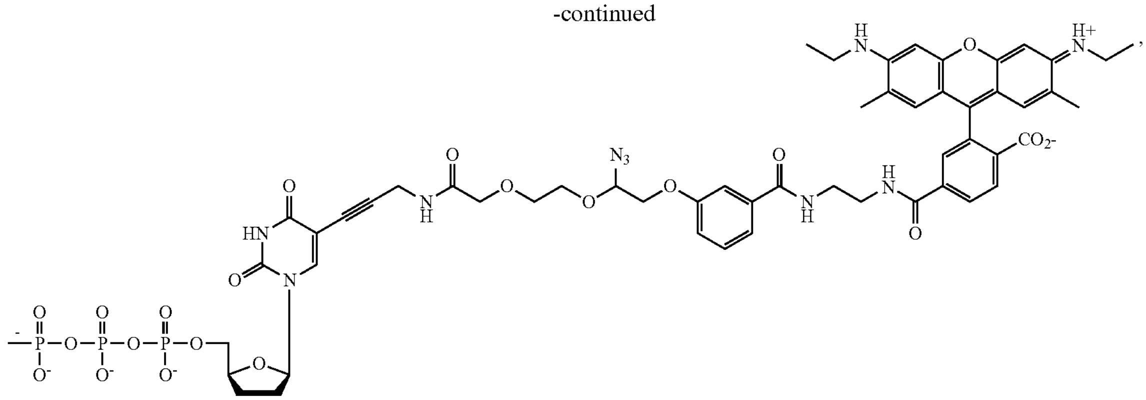

, and

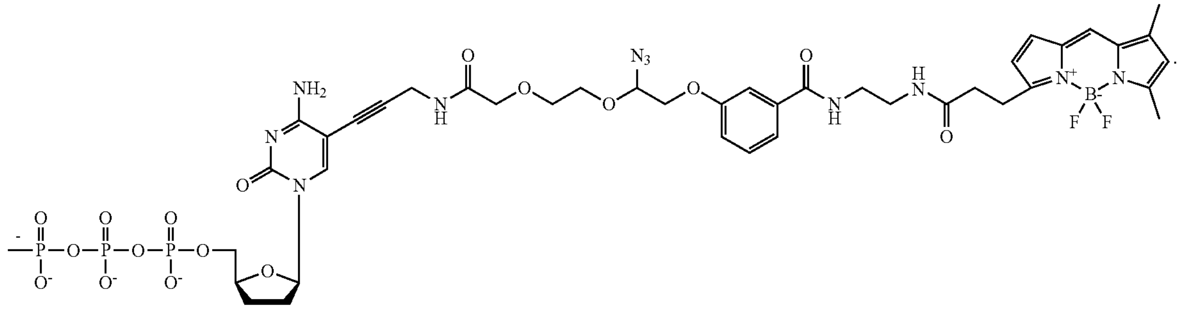

.

An array is provided comprising a nucleic acid attached to a solid surface, wherein the nucleic acid comprises an azidomethyl group attached to a 3' O atom thereof and a molecule having the structure:

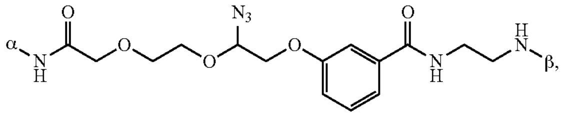

, wherein α represents a point of attachment to a 3' base of the nucleic acid and β represents a point of attachment to a detectable marker.

An array is provided comprising a self-priming nucleic acid attached to a solid surface, wherein the nucleic acid comprises an azidomethyl group attached to a 3' O atom thereof and a molecule having the structure:

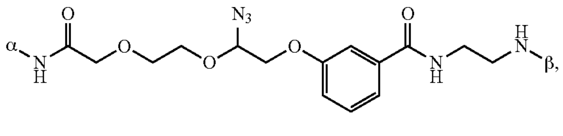

, wherein α represents a point of attachment to a 3' base of the nucleic acid and β represents a point of attachment to a detectable marker.

In embodiment the detectable marker is a fluorophore.

A method is provided for increasing a read length of DNA sequencing by synthesis coupled with Sanger dideoxynucleotide terminating reaction (a) providing deoxynucleotide triphosphate analogues wherein the deoxynucleotide triphosphate analogues differ from deoxynucleotide triphosphates by having a methylazido group attached to a 3' O atom thereof and providing dideoxynucleotide triphosphate analogues wherein the dideoxynucleotide triphosphate analogues differ from dideoxynucleotide triphosphates by having a detectable marker attached to a 1 nitrogen or a 9 nitrogen of a base thereof through a linker comprising the structure

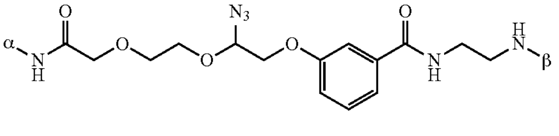

wherein α represents a point of attachment to a the base and β represents a point of attachment to the detectable marker and (b) incorporating a plurality ratio of dideoxynucleotide triphosphate to deoxynucleotide triphosphate analogues into a nucleic acid being synthesized in the DNA sequencing by synthesis.

This invention provides the instant method, wherein the detectable bound to the base via a cleavable linker is a dye, a fluorophore, a chromophore, a combinatorial fluorescence energy transfer tag, a mass tag, or an electrophore. Combinatorial fluorescence energy tags and methods for production thereof are disclosed in U.S. Pat. No. 6,627,748, which is hereby incorporated by reference.

Detectable tags and methods of affixing nucleic acids to surfaces which can be used in embodiments of the methods described herein are disclosed in U.S. Pat. Nos. 6,664,079 and 7,074,597 which are hereby incorporated by reference.

This invention also provides the instant method, wherein the primer is a self-priming moiety.

This invention also provides the instant method, wherein the DNA is bound to a solid substrate. This invention also provides the instant method, wherein the DNA is bound to the solid substrate via 1,3-dipolar azide-alkyne cycloaddition chemistry. This invention also provides the instant method, wherein the DNA is bound to the solid substrate via a polyethylene glycol molecule. This invention also provides the instant method, wherein the DNA is alkyne-labeled. This invention also provides the instant method, wherein the DNA is bound to the solid substrate via a polyethylene glycol molecule and the solid substrate is azide-functionalized. This invention also provides the instant method, wherein the DNA is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. This invention also provides the instant methods, wherein the DNA is bound to the solid substrate via a polyethylene glycol molecule and the solid substrate is azide-functionalized or the DNA is immobilized on the solid substrate via an azido linkage, an alkynyl linkage, or biotin-streptavidin interaction. In an embodiment, the DNA or nucleic acid is attached/bound to the solid surface by covalent site-specific coupling chemistry compatible with DNA.

This invention also provides the instant method, wherein the solid substrate is in the form of a chip, a bead, a well, a capillary tube, a slide, a wafer, a filter, a fiber, a porous media, or a column. This invention also provides the instant method, wherein the solid substrate is gold, quartz, silica, plastic, glass, nylon, diamond, silver, metal, or polypropylene. This invention also provides the instant method, wherein the solid substrate is porous. Chips or beads may be made from materials common for DNA microarrays, for example glass or nylon. Beads/micro-beads may be in turn immobilized to chips.

This invention also provides the instant method, wherein about 1000 or fewer copies of the DNA are bound to the solid substrate. This invention also provides the instant invention wherein $2\times10^7$, $1\times10^7$, $1\times10^6$ or $1\times10^4$ or fewer copies of the DNA are bound to the solid substrate.

This invention also provides the instant method, wherein the nucleotide analogues comprise one of the fluorophores Cy5, Bodipy-FL-510, ROX and R6G.

This invention also provides the instant method, wherein the DNA polymerase is a 9°N polymerase or a variant thereof. DNA polymerases which can be used in the instant invention include, for example *E. coli* DNA polymerase I, Bacteriophage T4 DNA polymerase, Sequenase™, Taq DNA polymerase and 9° N polymerase (exo-) A485L/Y409V. RNA polymerases which can be used in the instant invention include, for example, Bacteriophage SP6, T7 and T3 RNA polymerases.

Methods for production of cleavably capped and/or cleavably linked nucleotide analogues are disclosed in U.S. Pat. No. 6,664,079, which is hereby incorporated by reference.

A method for determining the identity of each of a series of consecutive nucleotide residues in a nucleic acid comprising:

a) contacting the nucleic acid with (i) at least four different deoxynucleotide triphosphate (dNTP) analogues, each having the structure:

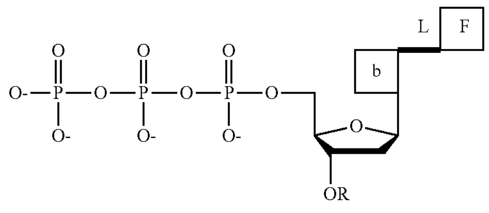

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) cleaving the linker attaching the fluorophore of the dNTP analogue which has formed the phosphodiester bond and cleaving the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, f) denaturing the extended primer so as to dehybridize it from the nucleic acid;

g) contacting the nucleic acid with (i) at least four different deoxynucleotide triphosphate (dNTP) analogues, each comprising an adenine, guanine, cytosine, uracil, inosine or 5-nitorindole base and each differing from a deoxynucleotide triphosphate by having a cleavable chemical group attached to the 3' O-atom of the dNTP, (ii) a nucleic acid polymerase and (iii) a second nucleic acid primer which hybridizes with the nucleic acid, under conditions permitting one of the four dNTP analogues that is complementary to the consecutive nucleotide residue to be identified to form a phosphodiester bond with the 3' end of the second nucleic acid primer and thereby extend the second primer;

h) cleaving the chemical group from the 3' O-atom of the dNTP analogue which has formed the phosphodiester bond so as to thereby permit incorporation of a further dNTP analogue into the extended second nucleic acid primer;

i) iteratively repeating steps g) and h) until the second primer is extended up to and including a residue corresponding to the final consecutive nucleotide residue identified in step e);

j) contacting the extended second primer with (i) at least four different deoxynucleotide triphosphate (dNTP) analogues, each having the structure:

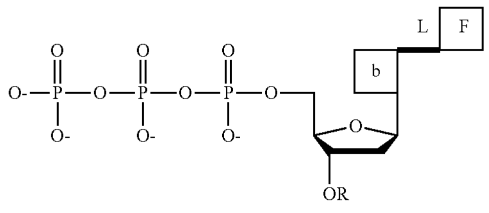

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, under conditions permitting one of the four dNTP analogues that is complementary to the next consecutive nucleotide residue to be identified to form a phosphodiester bond with the 3' end of the extended second nucleic acid primer and thereby further extend the second primer;

k) identifying the fluorophore of the dNTP analogue which has formed the phosphodiester bond, thereby identifying the consecutive nucleotide;

l) cleaving the fluorophore and the cleavable chemical group from the dNTP analogue which formed the phosphodiester bond so as to thereby permit incorporation of a further dNTP analogue into the extended second nucleic acid primer;

m) iteratively repeating steps j) through l) for each of the consecutive nucleotide residues to be identified until the final consecutive nucleotide residue is to be identified;

n) repeating steps j) and k) to identify the final consecutive nucleotide residue, so as to thereby determine the identity of each of the series of consecutive nucleotide residues in the nucleic acid.

In an embodiment the linker in each of step a) and j) independently each comprise the structure:

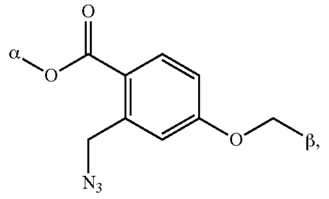

or the structure:

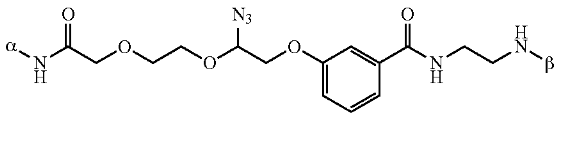

wherein α represents a point of attachment to the base and β represents a point of attachment to the fluorophore, and wherein R is a cleavable chemical group.

In an embodiment a linker is cleaved by contacting the linker with tris(2-carboxyethyl)phosphine.

In an embodiment one or more linkers are photocleavable or chemically cleavable.

In an embodiment one or more chemical groups are photocleavable or chemically cleavable.

In an embodiment R in the structures set forth in steps a) and or j) is independently chosen from a —$N_3$ group or an allyl group.

In an embodiment the cleavable chemical group in step g) is independently chosen from a —$N_3$ group or an allyl group.

A method for determining the identity of each of a series of consecutive nucleotide residues in a nucleic acid comprising:

a) contacting the nucleic acid with (i) at least four different deoxynucleotide triphosphate (dNTP) analogues, each having the structure:

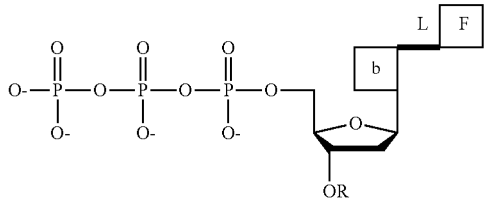

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) cleaving the linker attaching the fluorophore of the dNTP analogue which has formed the phosphodiester bond and cleaving the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, f) denaturing the extended primer so as to dehybridize it from the nucleic acid;

g) contacting the nucleic acid with (i) three different types of deoxynucleotide triphosphate, (ii) a nucleic acid polymerase and (iii) a second nucleic acid primer which hybridizes with the nucleic acid, under conditions permitting one of the three dNTP analogues that is complementary to the consecutive nucleotide residue to be identified to form a phosphodiester bond with the 3' end of the second nucleic acid primer and thereby extend the second nucleic acid primer;

h) contacting the nucleic acid with (i) three different types of deoxynucleotide triphosphate, wherein at least one of the types of deoxynucleotide triphosphate is not used in step g), under conditions permitting one of the three dNTP analogues that is complementary to the consecutive nucleotide residue to be identified to form a phosphodiester bond with the 3' end of the extended second nucleic acid primer and thereby further extend the second nucleic acid primer;

i) repeating steps g) and h) until the second nucleic acid primer is extended up to and including a residue corresponding to the final consecutive nucleotide residue identified in step e)

j) contacting the extended second nucleic acid primer with (i) at least four different deoxynucleotide triphosphate (dNTP) analogues, each having the structure:

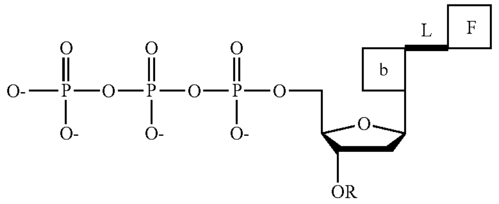

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, under conditions permitting one of the four dNTP analogues that is complementary to the next consecutive nucleotide residue to be identified to form a phosphodiester bond with the 3' end of the extended second nucleic acid primer and thereby further extend the second primer;

k) identifying the fluorophore of the dNTP analogue which has formed the phosphodiester bond, thereby identifying the consecutive nucleotide;

l) cleaving the fluorophore and the cleavable chemical group from the dNTP analogue which formed the phosphodiester bond so as to thereby permit incorporation of a further dNTP analogue into the extended second nucleic acid primer;

m) iteratively repeating steps j) through l) for each of the consecutive nucleotide residues to be identified until the final consecutive nucleotide residue is to be identified;

n) repeating steps j) and k) to identify the final consecutive nucleotide residue, so as to thereby determining the identity of each of the series of consecutive nucleotide residues in the nucleic acid.

In an embodiment in steps g) and h) the three types of dNTPs are chosen from the group dATP, dCTP, dGTP, dTTP or dITP.

In an embodiment the linker in each of step a) and j) independently each comprise the structure:

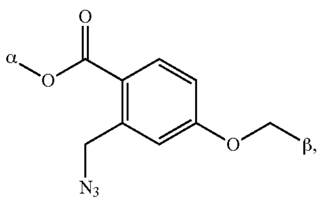

or the structure:

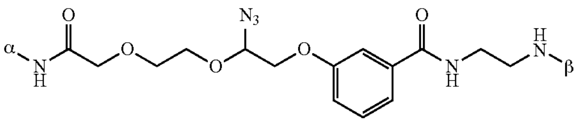

wherein α represents a point of attachment to the base and β represents a point of attachment to the fluorophore, and wherein R is a cleavable chemical group.

In an embodiment a linker is cleaved by contacting the linker with tris(2-carboxyethyl)phosphine.

In an embodiment one or more linkers are photocleavable or chemically cleavable.

In an embodiment one or more chemical groups are photocleavable or chemically cleavable.

In an embodiment R in the structures set forth in steps a) and or j) is independently chosen from a —$N_3$ group or an allyl group.

In an embodiment the cleavable chemical group in step g) is independently chosen from a —$N_3$ group or an allyl group.

A method for determining the identity of each of a series of consecutive nucleotide residues in a nucleic acid comprising:

a) contacting the nucleic acid with (i) at least four different deoxynucleotide triphosphate (dNTP) analogues, each having the structure:

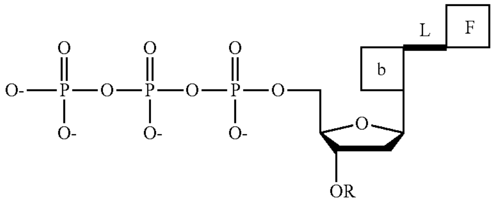

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) cleaving the linker attaching the fluorophore of the dNTP analogue which has formed the phosphodiester bond and cleaving the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, f) denaturing the extended primer so as to dehybridize it from the nucleic acid;

g) contacting the nucleic acid with (i) three different types of deoxynucleotide triphosphates, (ii) a deoxynucleotide triphosphate analogue, differing from a deoxynucleotide triphosphate by having a cleavable chemical group attached to the 3' O-atom of the dNTP analogue and differing from the three different types of deoxynucleotide triphosphates by having a different base therefrom, (iii) a nucleic acid polymerase and (iv) a second nucleic acid primer which hybridizes with the nucleic acid, under conditions permitting one of the three dNTPs or the dNTP analogue that is complementary to the consecutive nucleotide residue to be identified to form a phosphodiester bond with the 3' end of the second nucleic acid primer and thereby extend the second nucleic acid primer;

h) cleaving the cleavable chemical group from the 3'-O—R group;

repeating steps g) and h) until the second nucleic acid primer is extended up to and including a residue corresponding to the final consecutive nucleotide residue identified in step e)

i) contacting the extended second nucleic acid primer with (i) at least four different deoxynucleotide triphosphate (dNTP) analogues, each having the structure:

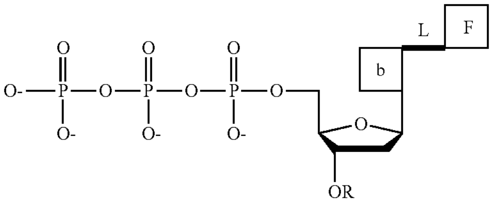

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, under conditions permitting one of the four dNTP analogues that is complementary to the next consecutive nucleotide residue to be identified to form a phosphodiester bond with the 3' end of the extended second nucleic acid primer and thereby further extend the second primer;

j) identifying the fluorophore of the dNTP analogue which has formed the phosphodiester bond, thereby identifying the consecutive nucleotide;

k) cleaving the fluorophore and the cleavable chemical group from the dNTP analogue which formed the phosphodiester bond so as to thereby permit incorporation of a further dNTP analogue into the extended second nucleic acid primer;

l) iteratively repeating steps j) through l) for each of the consecutive nucleotide residues to be identified until the final consecutive nucleotide residue is to be identified;

m) repeating steps j) and k) to identify the final consecutive nucleotide residue, so as to thereby determine the identity of each of the series of consecutive nucleotide residues in the nucleic acid.

In an embodiment in step g) the three types of dNTPs are chosen from the group dATP, dCTP, dGTP and dTTP.

In an embodiment the linker in each of step a) and j) independently each comprise the structure:

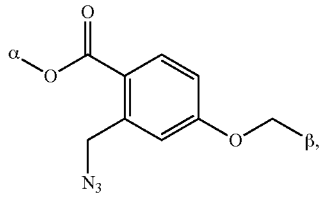

or the structure:

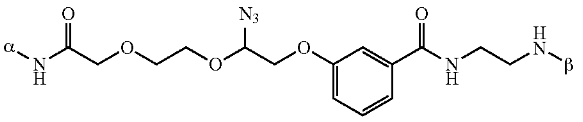

wherein α represents a point of attachment to the base and β represents a point of attachment to the fluorophore, and wherein R is a cleavable chemical group.

In an embodiment a linker is cleaved by contacting the linker with tris(2-carboxyethyl)phosphine.

In an embodiment one or more linkers are photocleavable or chemically cleavable.

In an embodiment one or more chemical groups are photocleavable or chemically cleavable.

In an embodiment R in the structures set forth in steps a) and or j) is independently chosen from a —$N_3$ group or an allyl group.

In an embodiment the cleavable chemical group in step g) is independently chosen from the a —$N_3$ group or an allyl group.

The methods described herein can be applied mutatis mutandis to sequencing RNA using the appropriate ddNTPS or analogues thereof and dNTPS and analogues thereof.

In the methods, base-pairing complementarity allows the sequence of the extended primer or of the target nucleic to be readily determined.

Dehybridize is understood by those skilled in the art to mean to disassociate the hybridized primer (or extended strand thereof) from the target nucleic acid without destroying the target nucleic acid and thus permitting further hybridization of a second primer to the target nucleic acid. Hybridization as used herein in one embodiment means stringent hybridization, for examples as described in Sambrook, J., Russell, D. W., (2000) Molecular Cloning: A Laboratory Manual: Third Edition. Cold Spring Harbor Laboratory Press "Type" of dNTP or ddNTP is used to distinguish dNTP or ddNTPs comprising different bases.

All combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Azido Modified Nucleotide Analogs

While both 3'-O-Allyl-dNTPs and 3'-O-photocleavable linker (PC)-dNTPs have offered concrete evidence for their implementation in sequencing by synthesis (SBS), a new set of nucleotide analogs, modified with the small azido group ($N_3$), is investigated to seek potential improvement over the current system. There are several advantages for using azido moiety as 3' capping group and also as a dye linker (3'-O-Azido-dNTPs-Azido-Dye), first and foremost being the application of extremely mild cleavage conditions. As disclosed herein, an example of the Staudinger reaction, an azido group can be effectively converted into an amine with phosphine in DNA-friendly aqueous solution (35). This efficient reduction is further enhanced through the utilization of Tris(2-Carboxyethyl) phosphine (TCEP), an odorless and stable agent often used to digest peptide disulfide bonds (FIG. 1).

Similar to allyl and nitrobenzyl alterations previously reported, two positions of the nucleotide need to be modified with the azido moiety to afford a set of 3'-O-Azido-dNTPs-Azido-Dye. The small azido methyl group ($—CH_2—N_3$) is used to cap the 3' position of the sugar base while a novel azido linker connects unique fluorophores to the 5' position of C/U and the 7' position of A/G (see novel structures in FIG. 2).

Figure 3:
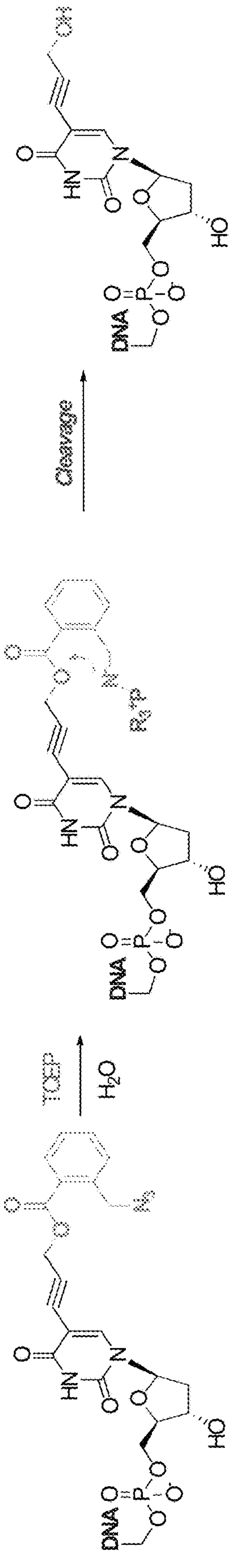
FIG. 3. Staudinger Reduction of the Azido Linker.

With such a formulation the same reagent (TCEP) can be used to cleave the azido groups at both positions simultaneous, although the mechanisms of cleavage differ slightly. According to Staudinger, TCEP reduces the azido-methyl capping group to methylamine at the 3' sugar base. Since the carbon of the methylamine is highly unstable due to its position between two electron-withdrawing elements (oxygen and nitrogen), the methylamine is hydrolyzed in the presence of water that recovers the hydroxyl group at the 3' position. For the azido linker, the same Straudinger reduction takes place. However immediately after the attachment of TCEP to azido, the intermediate attacks the ester bond to afford total cleavage of the fluorophore (FIG. 3).

In addition to the dual azido/azido modification, an alternative approach is to attach the fluorophore via a PC (nitrobenzyl) linker while conserving the 3' capping with the azido methyl group (3'-O-Azido-dNTPs-PC-Dye, FIG. 4) and cleaving the azido again using TCEP.

The extension and detection steps for this set of nucleotides are analogous to those for 3'-O-Azido-dNTPs-Azido-Dye. An additional photolysis procedure is involved during the deprotection step. This dual cleavage process might offer different advantages for removing the fluorophore than the Staudinger reduction.

An Alternative Sequencing Method that is a Hybrid Between the Sanger Dideoxy Chain Terminating Reaction, and SBS.

Figure 5:
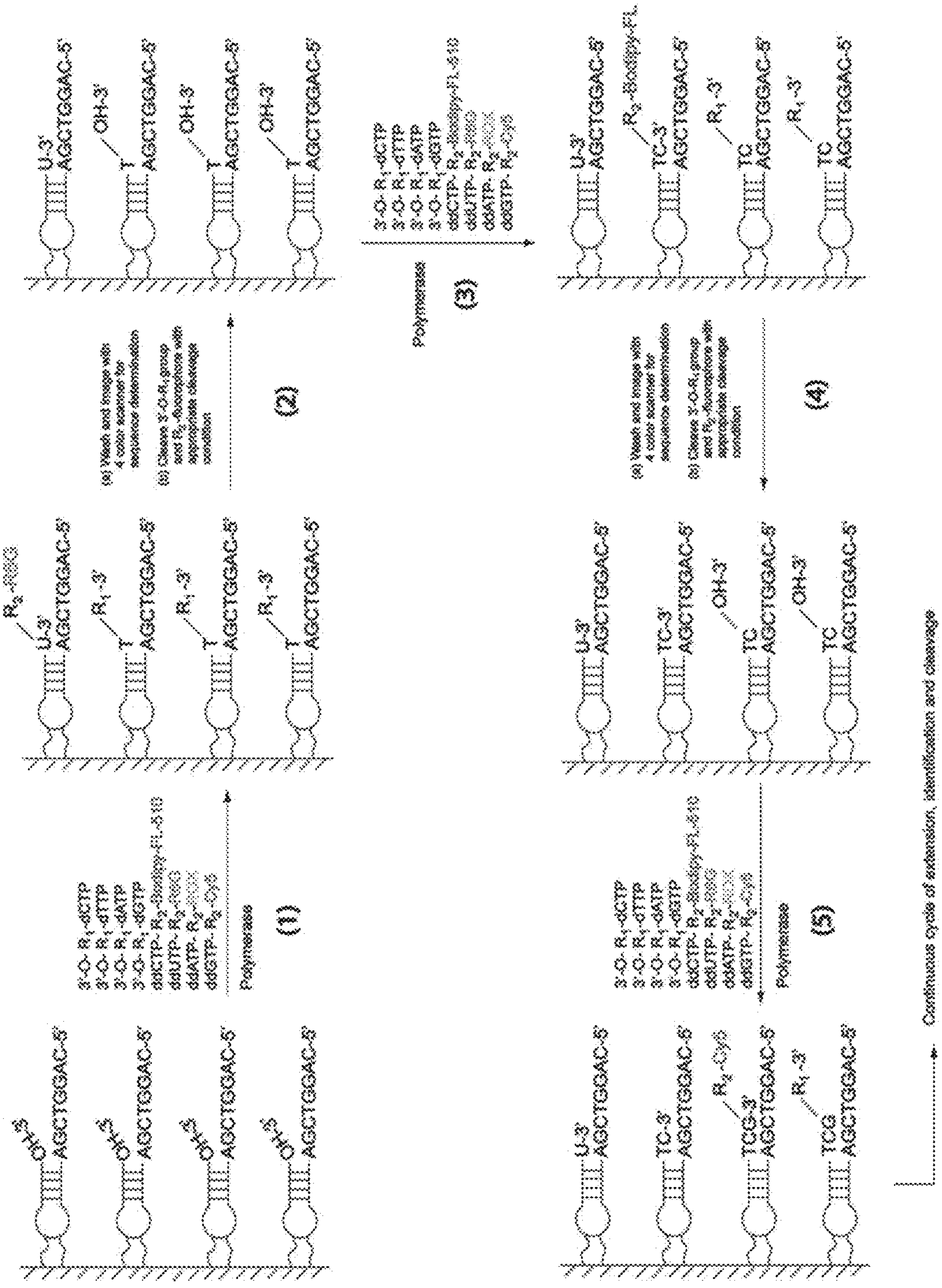
FIG. 5. The hybrid DNA sequencing approach between the Sanger dideoxy chain-terminating reaction and sequencing by synthesis. In this approach, four nucleotides (3'-O—$R_1$-dNTPs) modified as reversible terminators by capping the 3'-OH with a small reversible moiety $R_1$ so that they are still recognized by DNA polymerase as substrates, are used in combination with a small percentage of four cleavable fluorescent dideoxynucleotides (ddNTP-$R_2$-fluorophores) to perform SBS. DNA sequences are determined by the unique fluorescence emission of each fluorophore on the DNA products terminated by ddNTPs. On removing the 3'-OH capping group $R_1$ from the DNA products generated by incorporating the 3'-O—$R_1$-dNTPs, and the cleavage of the $R_2$ linker to remove the fluorophore from the DNA products terminated with the ddNTPs, the polymerase reaction reinitiates to continue the sequence determination.

In this approach, four nucleotides, modified as reversible terminators by capping the 3'-OH with a small reversible moiety so that they are still recognized as substrates by DNA polymerase, are used in combination with a small percentage of four cleavable fluorescent dideoxynucleotides to perform SBS. DNA sequences are determined by the unique fluorescence emission of each fluorophore on the DNA products terminated by ddNTPs. Upon removing the 3'-OH capping group from the DNA products generated by incorporating the 3'-O-modified dNTPs and the fluorophore from the DNA products terminated with the ddNTPs, the polymerase reaction reinitiates to continue the sequence determination (FIG. 5).

Using an azidomethyl group as a chemically reversible capping moiety in the 3'-O-modified dNTPs, and an azido-based cleavable linker to attach the fluorophores to ddNTPs, four 3'-O—$N_3$-dNTPs and four ddNTP-$N_3$-fluorophores were synthesized for the hybrid SBS. The azidomethyl capping moiety on the 3'-OH group and the cleavable fluorophore on the DNA extension products are efficiently removed after fluorescence detection for sequence determination using a chemical method that is compatible to DNA. Various DNA templates, including those with homopolymer regions, were accurately sequenced with read length of over 30 bases using this hybrid SBS method.

Sequence by Synthesis with Template "Walking"

The fundamental rationale behind primer resetting is to regenerate the original primer site or to insert two or more primer sites of known sequences into the target DNA so SBS can be carried out at each site sequentially. In general, three steps are involved with this approach: 1) annealing of the first primer, 2) performing SBS, 3) denaturing the sequenced section of the template to recover a single-stranded DNA for the second primer annealing. These steps are carried out repeatedly until the target DNA is sequenced in its entirety. The advantage of primer resetting lies in its ability to restore all the templates after the denaturation step, including those that are terminated with ddNTPs, so the next cycle of SBS can restart with potentially the same amount of sequenceable DNA as the previous round.

Three approaches for achieving longer read lengths that rely on this template "walking" concept are described. In the first strategy, the DNA sequence is reset by reattaching the original primer, extending the chain with natural or minimally modified nucleotides to the end of the first round sequence, and then sequencing from that point. The second strategy relies on annealing of a second round primer that is longer than the first, containing at its 5' end the same sequence as the original primer, followed by a run of 20 universal nucleotides such as inosine, from which the second round of sequencing can be primed. If the duplex stability of this highly degenerate primer with DNA templates is found to be low, a number of locked nucleotides can be added at either end of the primer to increase the stability of the primer-template complex. In the third strategy, extra priming sites are inserted within a template strand via Type IIS or Type III restriction-recircularization. Each of these approaches has distinct advantages and some difficulties that need to be overcome. None of the three aforementioned strategies are sensitive to the type of library (genomic, cDNA or other), to the method of amplification prior to sequencing (spotting of clones, ePCR, polony PCR), or the mode of sequencing (Hybrid SBS and SBS with C—F—NRTs). Hence they are all sequence unbiased, thus greatly increasing their range of applications in sequencing technologies.

Results

Solution Extension with 3'-O-Azido-dNTPs

To verify the feasibility of using azido-modified nucleotides in SBS, a set of 3'-O-Azido-dNTPs (FIG. 6) were first designed and synthesized.

Figure 7:
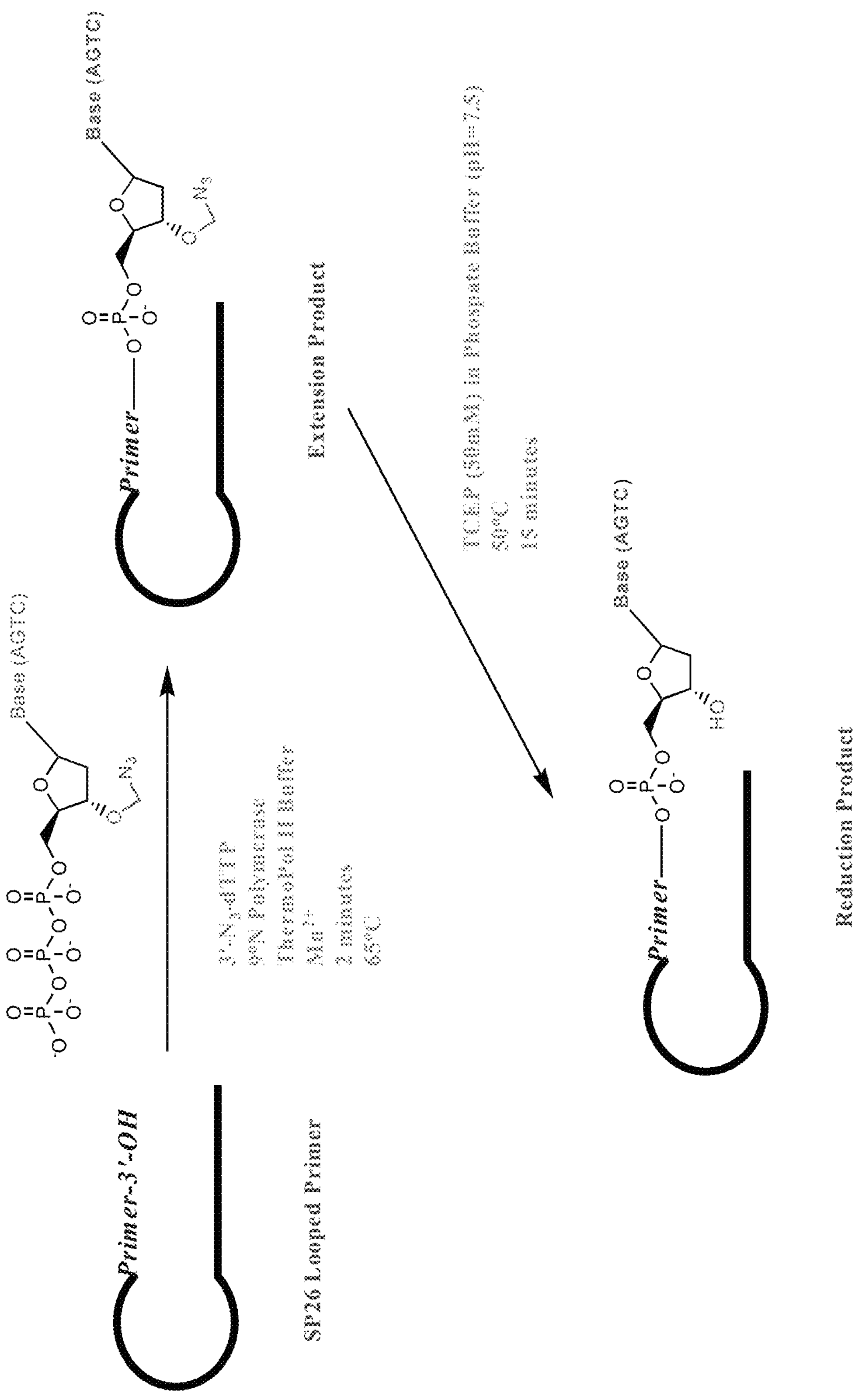
FIG. 7. Solution Incorporation and reduction of 3'-O-Azido-dNTPs: polymerase extension and TCEP reduction scheme.
Figure 8:
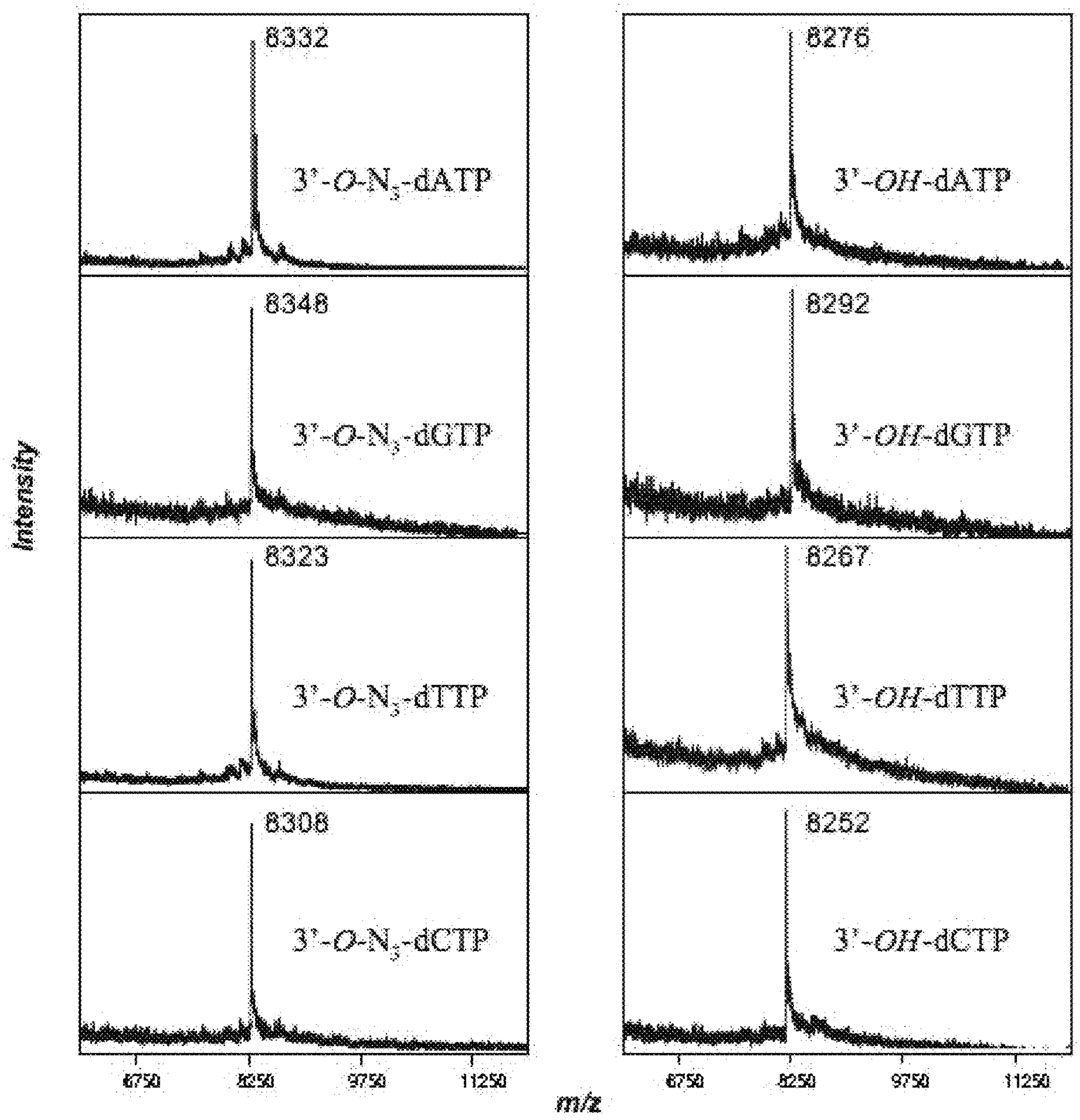
FIG. 8. MALDI-TOF MS spectra of incorporation products (left column), and MALDI-TOF MS spectra of reduction products (right column).

Each nucleotide analog (3'-O-Azido-dATP, mw=541; 3'-O-Azido-dGTP, mw=558; 3'—O-Azido-dCTP, mw=518; 3'—O-Azido-dTTP, mw=533) was incorporated into its corresponding looped primer in solution with manganese (Mn2+, 20 mM) and the mutant 9°N Thermopolymerase. The extensions were carried out at 65° C. for various time spans ranging from 20 minutes to 5 minutes. Even with the shortest reaction time of 5 minutes, 100% incorporation was confirmed with MALDI-TOF mass spectroscopy (MS) by observing the total disappearance of primer peak (m/z=7966) and the emergence of extended product peak (~m/z=8320, FIG. 7). After obtaining the extended product for each nucleotide, deprotection was carried out with varying conditions such as time (1~20 minutes), temperature (20~60° C.), and concentration of TCEP (1~50 mM). It was determined that at 50° C. with 5 mM of TCEP, the 3' azido methyl capping group could be removed completely under 5 minutes. MALDI-TOF mass spectroscopy was again used to ascertain the results (FIG. 8).

3'-O-Azido-dNTPs-Azido Linker-Dye

Figure 9:
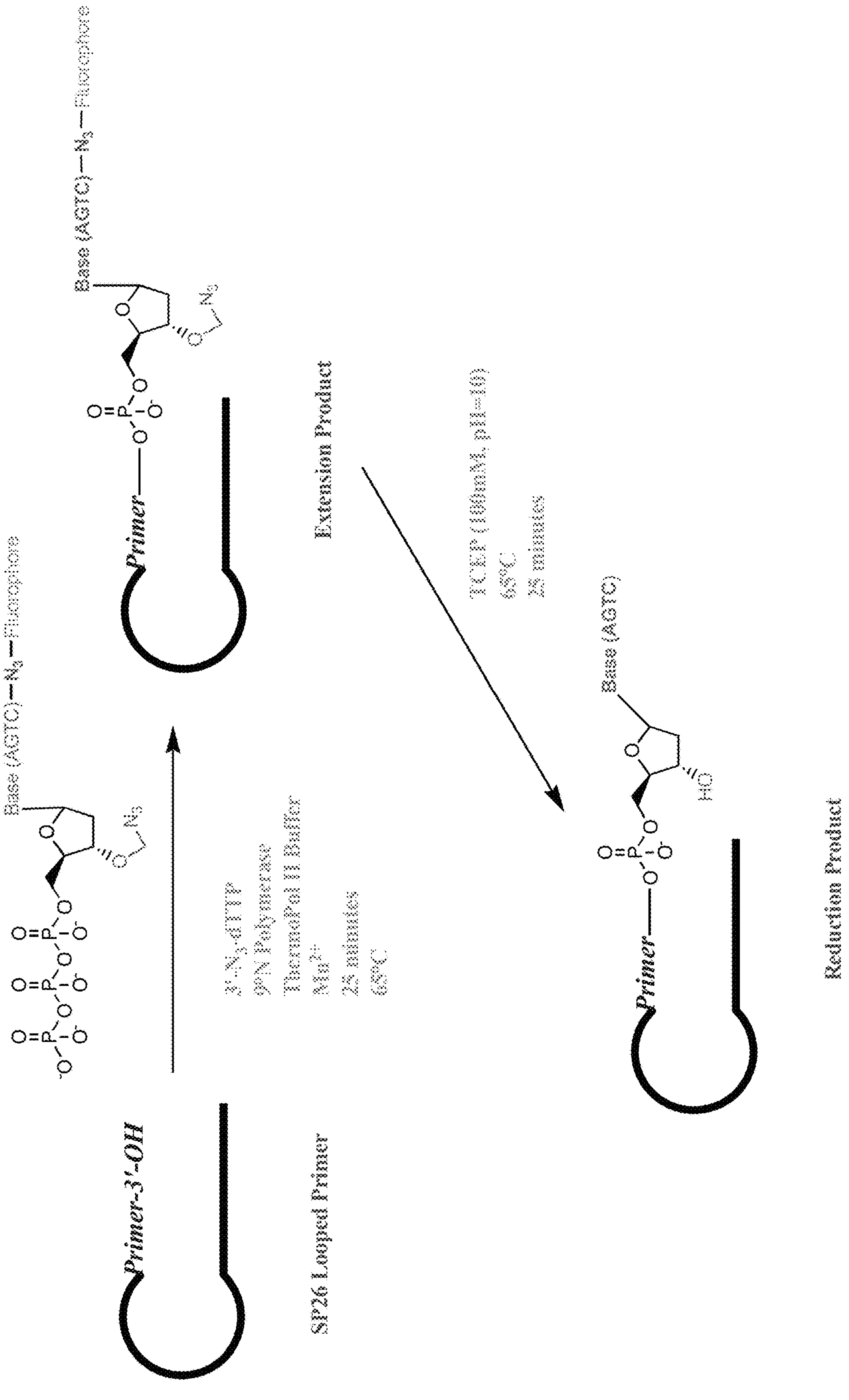
FIG. 9. Solution incorporation and reduction scheme of 3'-O-Azido-dNTPs-Azido-Dye.
Figure 10:
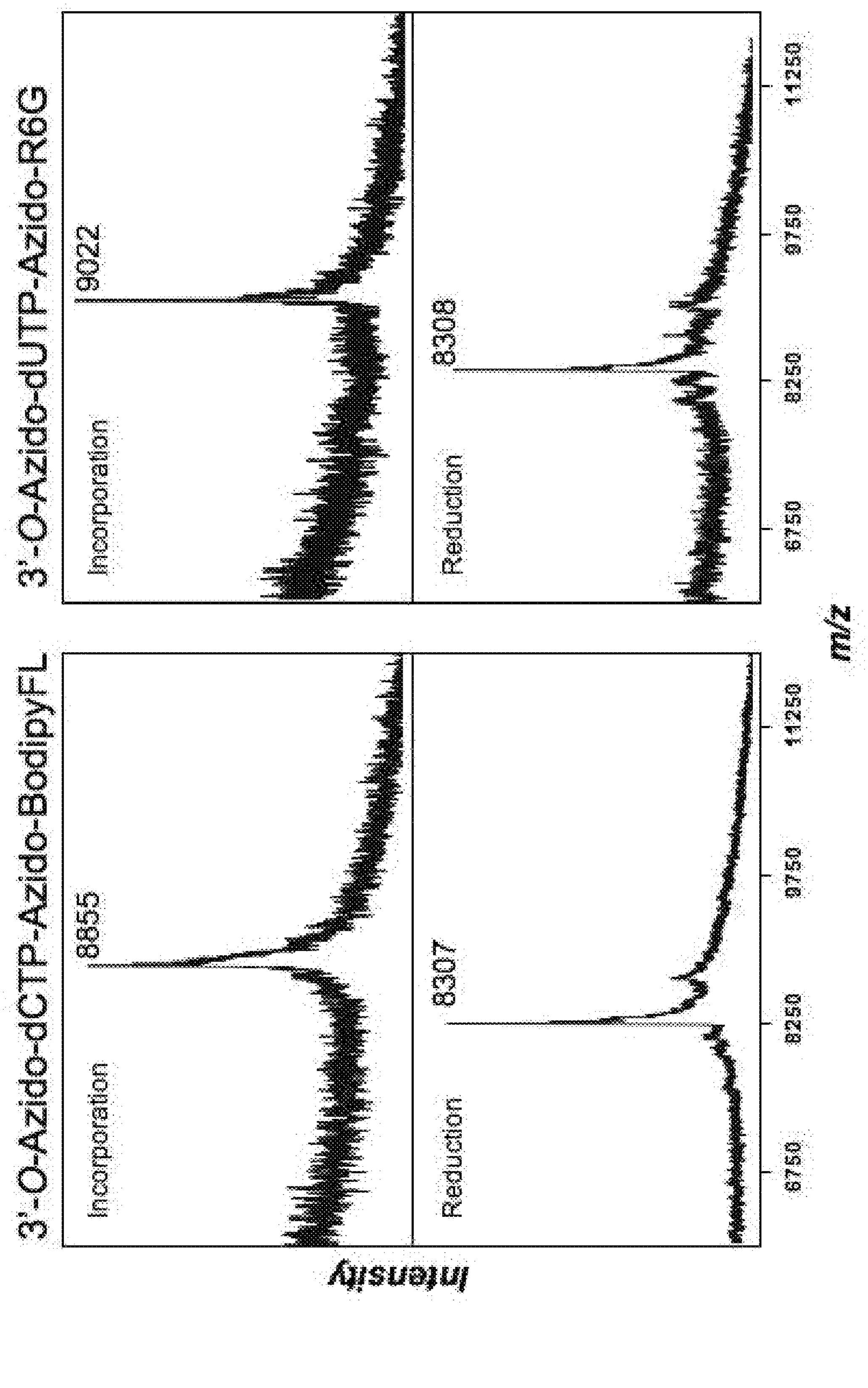
FIG. 10. MALDI-TOF MS spectra results for incorporation shown in FIG. 8.

Solution Extension with 3'-O-Azido-dNTPs-Azido-Dye Immediately after establishing the protocol to work with azido-modified nucleotides in SBS, synthetic work for the set of 3'-O-Azido-dNTPs-Azido Linker-Dye was set forth. Two nucleotides, 3'-O-Azido-dCTP—PC-BodipyFL and 3'-O-Azido-dUTP—PC-R6G were successfully synthesized and characterized. To test the incorporation of each nucleotide, extension reactions in solution, similar to those with 3'-O-Azido-dNTPs, were carried out with looped primer (m/z=7966), 9°N Thermopolymerase enzyme, and Mn2+ at 65° C. for 25 minutes. The products were verified through MALDI-TOF MS (FIG. 9). After obtaining the extension products, reduction reactions were performed under various conditions to optimize the process. It was observed that both azido linker and 3' protection group were removed with 100 mM TCEP with pH=10 at 65° C. for 25 minutes (MALDI-TOF MS spectra in FIG. 10).

Surface Extension with 3'-O-Azido-dNTPs-Azido Linker-Dye

Figure 11:
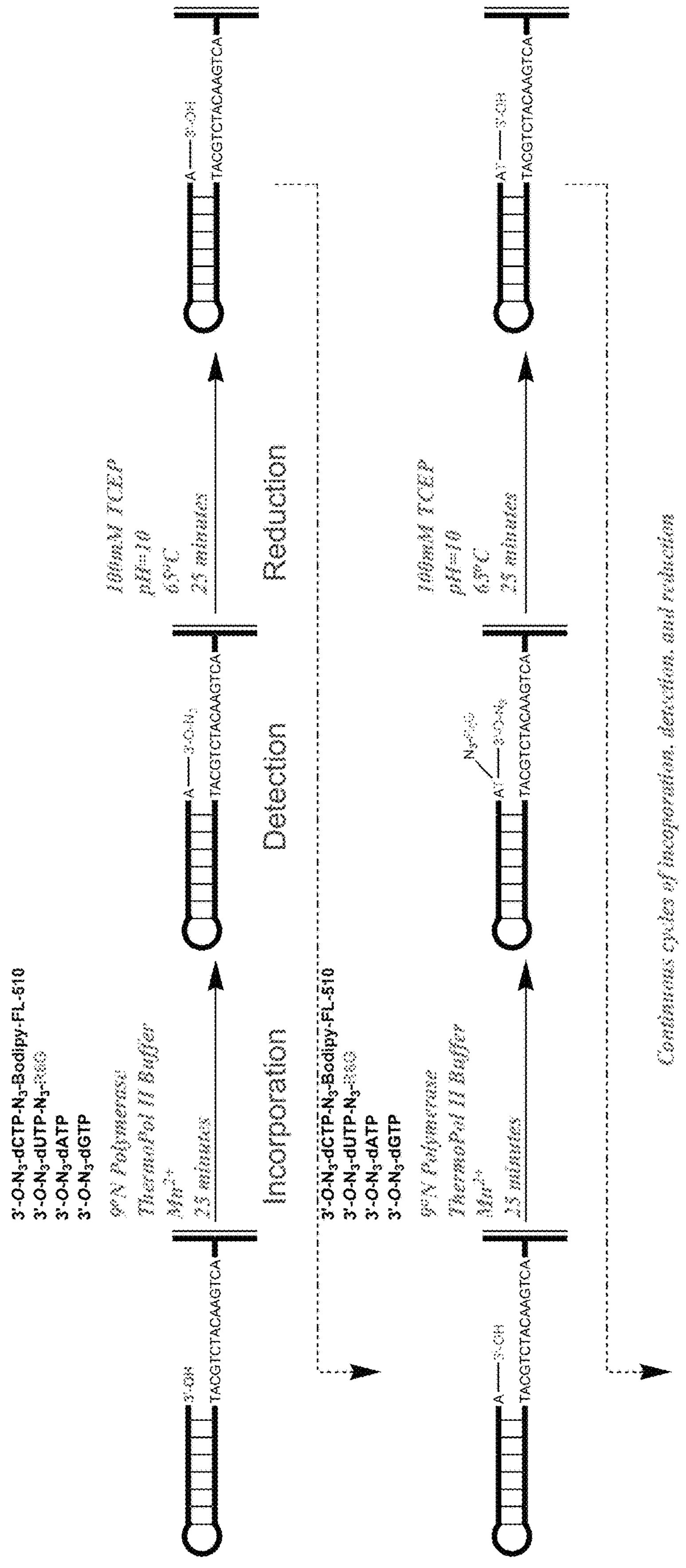
FIG. 11. SBS scheme for 3'-O-Azido-dNTPs-Azido-Dye.
Figure 12:
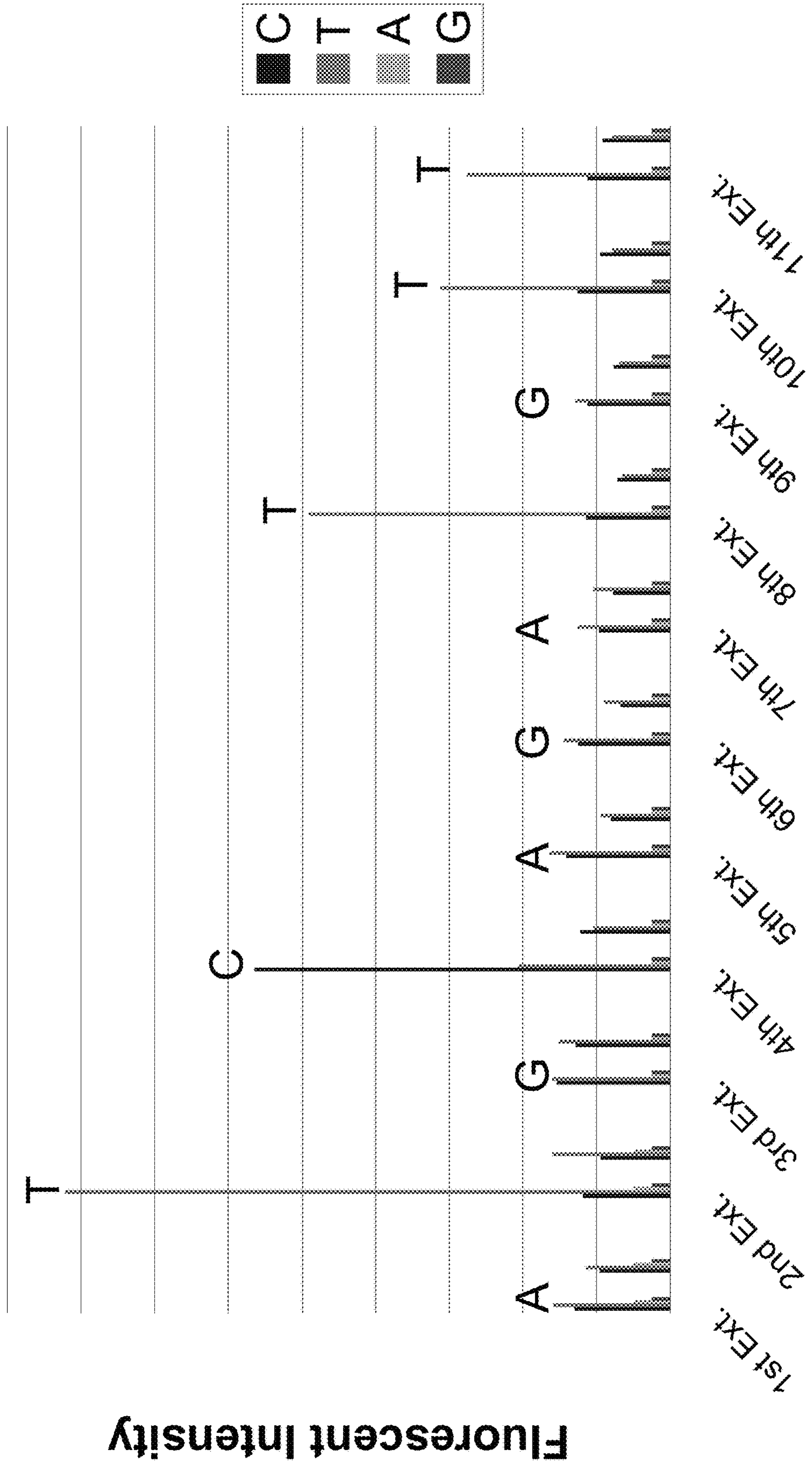
FIG. 12. Results for incorporation shown in FIG. 10.

As a part of the preliminary study, the two chemically cleavable fluorescent nucleotide analogs were used in an SBS reaction to identify the sequence of a self-primed DNA template (130 base pairs) immobilized on a solid surface. A reaction mixture of 3'-O-Azido-dCTP-Azido-BodipyFL, 3'-O-Azido-dUTP-Azido-R6G, 3'-O-Azido-dATP, and 3'-O-Azido-dGTP were prepared for the incorporation. A synchronization step was performed with the full set of 3'-O-Azido-dNTPs after incorporation to extend any remaining priming strand. After detection of the fluorescent signal, the chip surface was immersed in reduction solution (100 mM TCEP, pH=10) and incubated for 25 minutes at 65° C. to cleave both the fluorophore and 3'-O-Azido group. Upon confirmation of the removal of fluorophore, the cycles of extension, detection, and reduction were repeated to sequence the following bases (FIGS. 11 and 12).

SBS on Surface with 3'-O-Azido-dNTPs-PC/Azido-Dye

Upon completing the synthesis of both 3'-O-Azido-dNTPs-PC-Dye and 3'-O-Azido-dNTPs-Azido-Dye sets, sequencing by synthesis of DNA templates attached on solid surface will be carried out. By carefully optimizing incorporation and cleavage conditions, the goal will be the achievement of maximum base read length of each template with high consistency.

PCR Product Attachment on Beads

To expand the efficiency and increase the throughput of SBS, it is ideal to attach large quantities of different DNA templates to solid surface so that each one of these templates can be sequenced during a single cycle of SBS simultaneously. One approach will be to affix PCR product on a single bead, and then immobilize copious amount of such beads on one glass chip. Various types of beads, such as magnetic, melamine, and sepharose, will be tested in order to select one with efficient attachment to surface, durable stability during reaction cycles, and minimal unspecific absorption of fluorophores. By coupling the micro-beads chip with the azido modified reversible terminator nucleotides, SBS technology will reach the next plateau of high-throughput DNA sequencing.

Design and Synthesis of 3'-O-Modified NRTs and Cleavable Fluorescent Dideoxynucleotide Terminators for the Hybrid SBS.

Four 3'-O-azidomethyl-modified NRTs (3'-O—$N_3$-dNTPs) (FIG. 6) were synthesized and evaluated for the hybrid SBS. The 3'-O-azidomethyl group on the DNA extension product generated by incorporating each of the NRTs was efficiently removed by the Staudinger reaction by using aqueous Tris(2-carboxyethyl) phosphine (TCEP) solution (36,37) followed by hydrolysis to yield a free 3'-OH group for elongating the DNA chain in subsequent cycles of the hybrid SBS (FIG. 13A).

To demonstrate the feasibility of carrying out the hybrid SBS on a DNA chip, four cleavable fluorescent dideoxynucleotides ddNTP-$N_3$-fluorophores (ddCTP-$N_3$-Bodipy-FL-510, ddUTP-$N_3$-R6G, ddATP-$N_3$—ROX, and ddGTP-$N_3$-Cy5) were synthesized (FIGS. 14-22). The ddNTP-$N_3$-fluorophores would be combined with the 4 NRTs (FIG. 6) to perform the hybrid SBS. Modified DNA polymerases have been shown to be highly tolerant to nucleotide modifications with bulky groups at the 5 position of pyrimidines (C and U) and the 7 position of purines (A and G) (27). Thus, a unique fluorophore was attached to the 5 position of C/U and the 7 position of A/G through a cleavable linker, which is also based on an azido-modified moiety (37) as a trigger for cleavage, a mechanism that is similar to the removal of the 5'-O-azidomethyl group (FIG. 13B). The ddNTP-$N_3$-fluorophores are found to efficiently incorporate into the growing DNA strand to terminate DNA synthesis for sequence determination. The fluorophore on a DNA extension product, which is generated by incorporation of the cleavable fluorescent ddNTPs, is removed rapidly and quantitatively by TCEP from the DNA extension product in aqueous solution.

Figure 19:
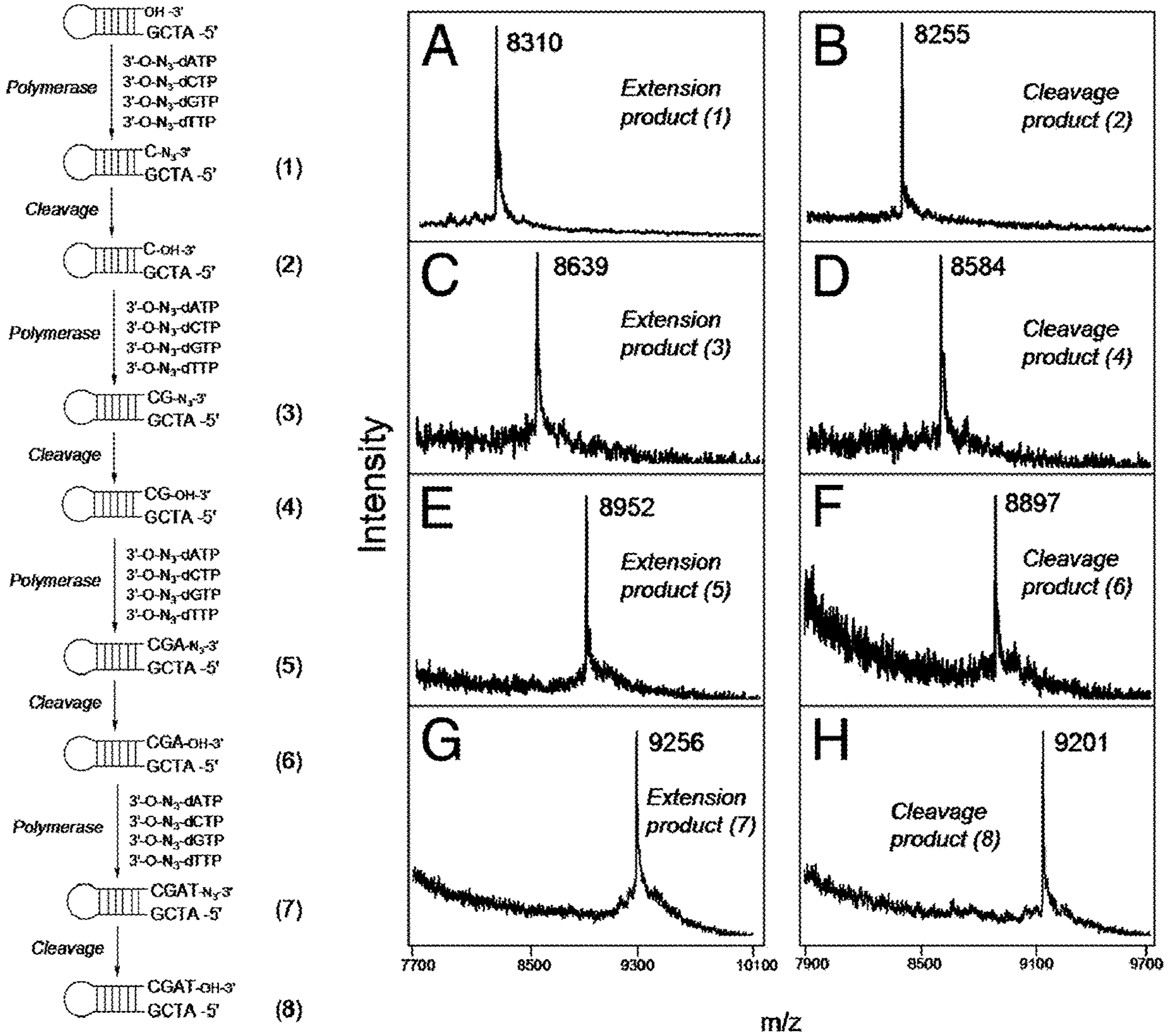

Continuous Polymerase Extension by Using 3'-O-Modified NRTs and Characterization by MALDI-TOF Mass Spectrometry To verify that the 3'-O—$N_3$-dNTPs incorporate accurately in a base specific manner, four continuous DNA extension reaction and cleavage were carried out in solution by using 3'-O—$N_3$-dNTPs as substrates. This allowed the isolation of the DNA product at each step for detailed molecular structure characterization as shown in FIG. 19. The first extension product 5'-primer-C—$N_3$-3' was desalted and analyzed using MALDI-TOF MS (FIG. 19(A)). This product was then incubated in aqueous solution to remove the azidomethyl moiety to yield the cleavage product with a free 3'OH group, which was also analyzed using MALDI-TOF MS (FIG. 19(B)). As can be seen from FIG. 19(A), the MALDI-TOF MS spectrum consist of a distinct peak corresponding to the DNA extension product 5'-primer-C—$N_3$3' (m/z 8,310), which confirms that the NRT can be incorporated base-specifically by DNA polymerase into a growing DNA strand. FIG. 19(B) shows the cleavage result on the DNA extension product. The extended DNA mass peak at m/z 8,310 completely disappeared, whereas the peak corresponding to the cleavage product 5'-primer-C-3' appears as the sole dominant peak at m/z 8,255, which establishes that TCEP incubation completely cleaves the 3'-O-azidomethyl group with high efficiency. The next extension reaction was carried out by using this cleaved product, which now has a free 3'-OH group, as a primer to yield a second extension product, 5'-primer-CG$N_3$-3' (m/z 8,639; FIG. 19C). As described above, the extension product was cleaved to generate product for further MS analysis yielding a single peak at m/z 8,584 (FIG. 19(D)). The third extension reaction to yield 5'-primer-CGA-$N_3$-3' (m/z 8,952; FIG. 19(E)), the fourth extension to yield 5'-primer-CGAT-$N_3$-3' (m/z 9,256; FIG. 19(G)) and their cleavage to yield products (m/z 8,897; FIG. 19(F)) and (m/z 9,201; FIG. 19(H)) were similarly carried out and analyzed by MALDI-TOF MS. These results demonstrate that all four 3'-O—$N_3$-dNTPs are successfully synthesized and efficiently incorporated base-specifically into the growing DNA strand in a continuous polymerase reaction as reversible terminators and the 3'-OH capping group on the DNA extension products is quantitatively cleaved by TCEP.

Figure 20:
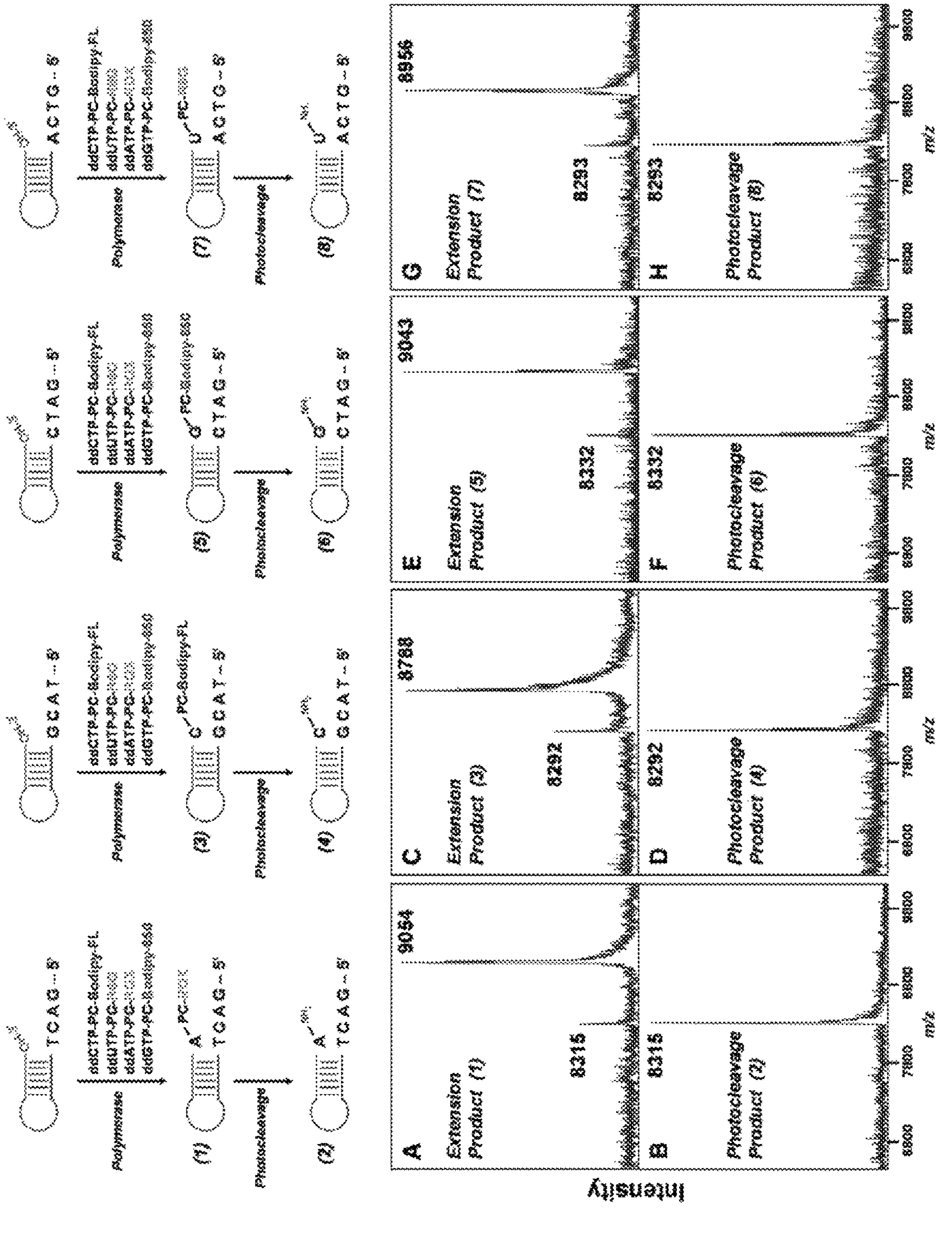

Polymerase Extension by Cleavable Fluorescent Dideoxynucleotide Terminators and Characterization by MALDI-TOF Mass Spectrometry To verify that the four cleavable fluorescent ddNTPs (ddCTP-$N_3$-Bodipy-FL-510, ddUTP-$N_3$-R6G, ddATP-$N_3$—ROX, and ddGTP-$N_3$-Cy5) (FIG. 14) are incorporated accurately in a base-specific manner in a polymerase reaction, single-base extension reactions with four different self-priming DNA templates whose next complementary base was either A, C, G, or T were carried out in solution. After the reaction, the four different primer extension products were analyzed by MALDI-TOF MS as shown in FIG. 20. Single clear mass peaks at 9,180, 8,915, 9,317, and 9,082 (m/z) corresponding to each primer extension product with no leftover starting materials were produced by using ddNTP-$N_3$-fluorophores (FIGS. 20 A, C, E, and G). Brief incubation of the DNA extension products in an aqueous TCEP solution led to the cleavage of the linker tethering the fluorophore to the dideoxynucleotide. FIGS. 20 B, D, F, and H shows the cleavage results for the DNA products extended with ddNTP-$N_3$-fluorophores. The mass peaks at 9,180, 8,915, 9,317, and 9,082 (m/z) have completely disappeared, whereas single peaks corresponding to the cleavage products appear at 8,417, 8,394, 8,433, and 8,395 (m/z), respectively. These results demonstrate that cleavable fluorescent ddNTPs are successfully synthesized and efficiently terminated the DNA synthesis in a polymerase reaction and that the fluorophores are quantitatively cleaved by TCEP. Thus, these ddNTP analogues meet the key requirements necessary for performing the hybrid SBS in combination with the NRTs.

4-Color DNA Sequencing by Synthesis on a Chip Using Photocleavable Fluorescent Dideoxynucleotide/3'-Modified Photocleavable Nucleotide Combination Remnant of Sanger Sequencing.

Figure 21:
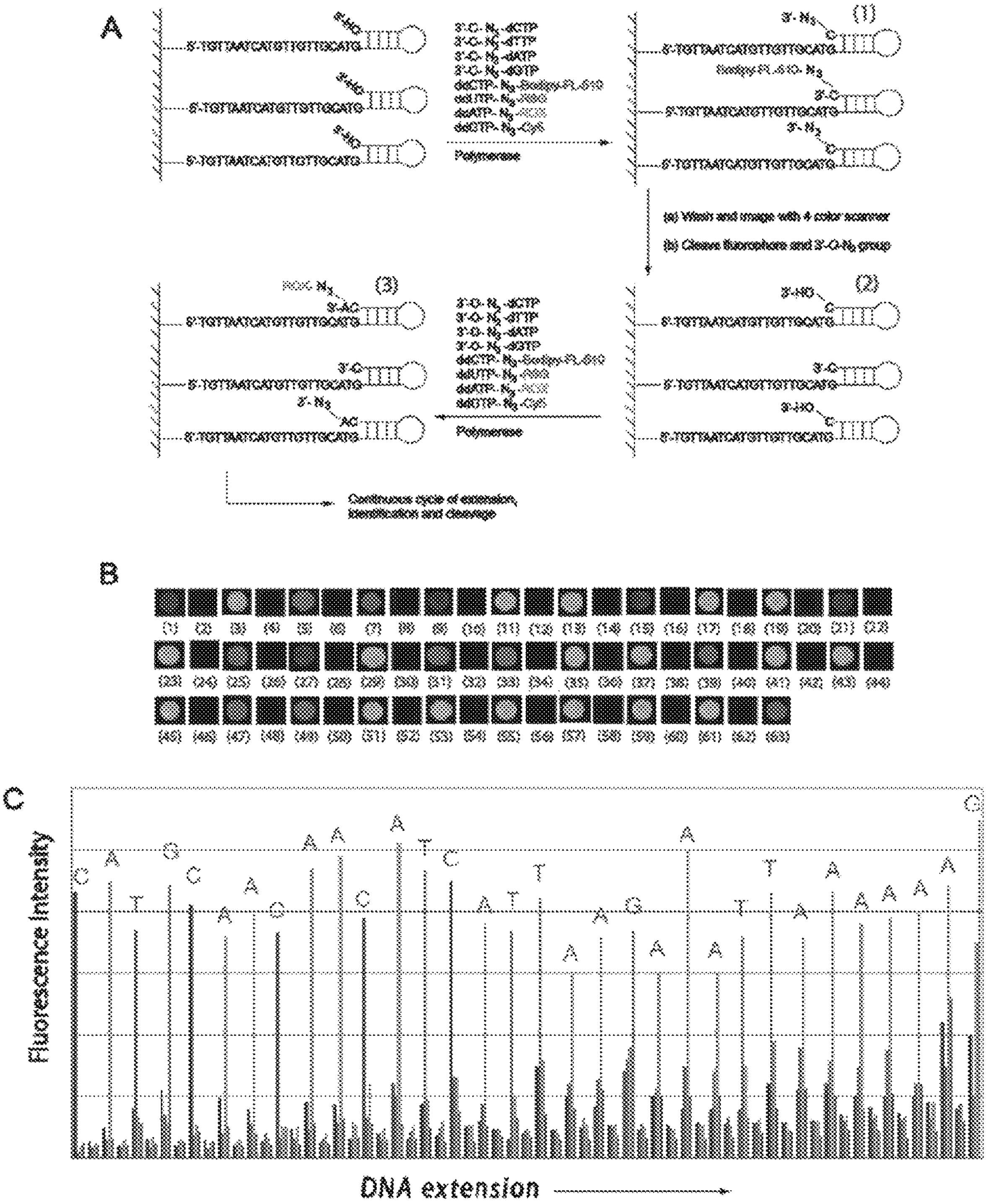
FIGS. 21A-C.

In the four-color hybrid SBS approach, the identity of the incorporated nucleotide is determined by the unique fluorescent emission from the four fluorescent dideoxynucleotide terminators, while the role of the 3'-O-modified NRTs is to further extend the DNA strand to continue the determination of the DNA sequence. Therefore, the ratio between the amount of ddNTP-$N_3$-fluorophores and 3'-O—$N_3$-dNTPs during the polymerase reaction determines how much of the ddNTP-$N_3$-fluorophores incorporate and thus the corresponding fluorescent emission strength. With a finite amount of immobilized DNA template on a solid surface, initially the majority of the priming strands should be extended with 3'-O—$N_3$-dNTPs, while a relative smaller amount should be extended with ddNTP-$N_3$-fluorophores to produce fluorescent signals that are above the fluorescent detection system's sensitivity threshold for sequence determination. As the sequencing cycle continues, the amount of the ddNTP-$N_3$-fluorophores need to be gradually increased to maintain the fluorescence emission strength for detection. Following these guidelines, we performed the hybrid SBS on a chip-immobilized DNA template using the 3'-O—$N_3$-dNTP/ddNTP-$N_3$-fluorophore combination and the results are shown in FIG. 21. The general four-color sequencing reaction scheme on a chip is shown in FIG. 21A.

De novo sequencing reaction on the chip was initiated by extending the self-priming DNA by using a solution consisting of four 3'-O—$N_3$-dNTPs and four ddNTP-$N_3$-fluorophores, and 9° N DNA polymerase. The hybrid SBS allows for the addition of all eight, nucleotide substrates simultaneously to unambiguously determine DNA sequences. This reduces the number of steps needed to complete the sequencing cycle, while increasing the sequencing accuracy because of competition among the substrates in the polymerase reaction. The DNA products extended by ddNTP-$N_3$-fluorophores, after fluorescence detection for sequence determination and cleavage, are no longer involved in the subsequent polymerase reaction cycles because they are permanently terminated. Therefore, further polymerase reaction only occurs on a DNA strand that incorporates the 3'-O—$N_3$-dNTPs, which subsequently turn back into natural nucleotide on cleavage of the 3'-OH capping group, and should have no deleterious effect on the polymerase binding to incorporate subsequent nucleotides for growing the DNA chains. However, successive addition of the previously designed cleavable fluorescent NRTs (22, 37, 38) into a growing DNA strand during SBS leads to a newly synthesized DNA chain with a leftover propargyl amino group at each nucleobase. This may interfere with the ability of the enzyme to efficiently incorporate the next incoming nucleotide, which will lead to loss of synchrony and thereby reduction in the read length. This challenge might potentially be overcome by reengineering DNA polymerases that efficiently recognize and accept the modified DNA strand, or by alternative design of the fluorescent NRTs (39).

To negate any lagging fluorescence signal that is caused by a previously unextended priming strand, a synchronization step was added to reduce the amount of unextended priming strands after the initial extension reaction shown in the scheme of FIG. 21A. A synchronization reaction mixture consisting of just the four 3'-O—$N_3$-dNTPs in relatively high concentration was used along with the 9°N DNA polymerase to extend, any remaining priming strands that retain a free 3'-OH group to synchronize the incorporation.

Figure 22:
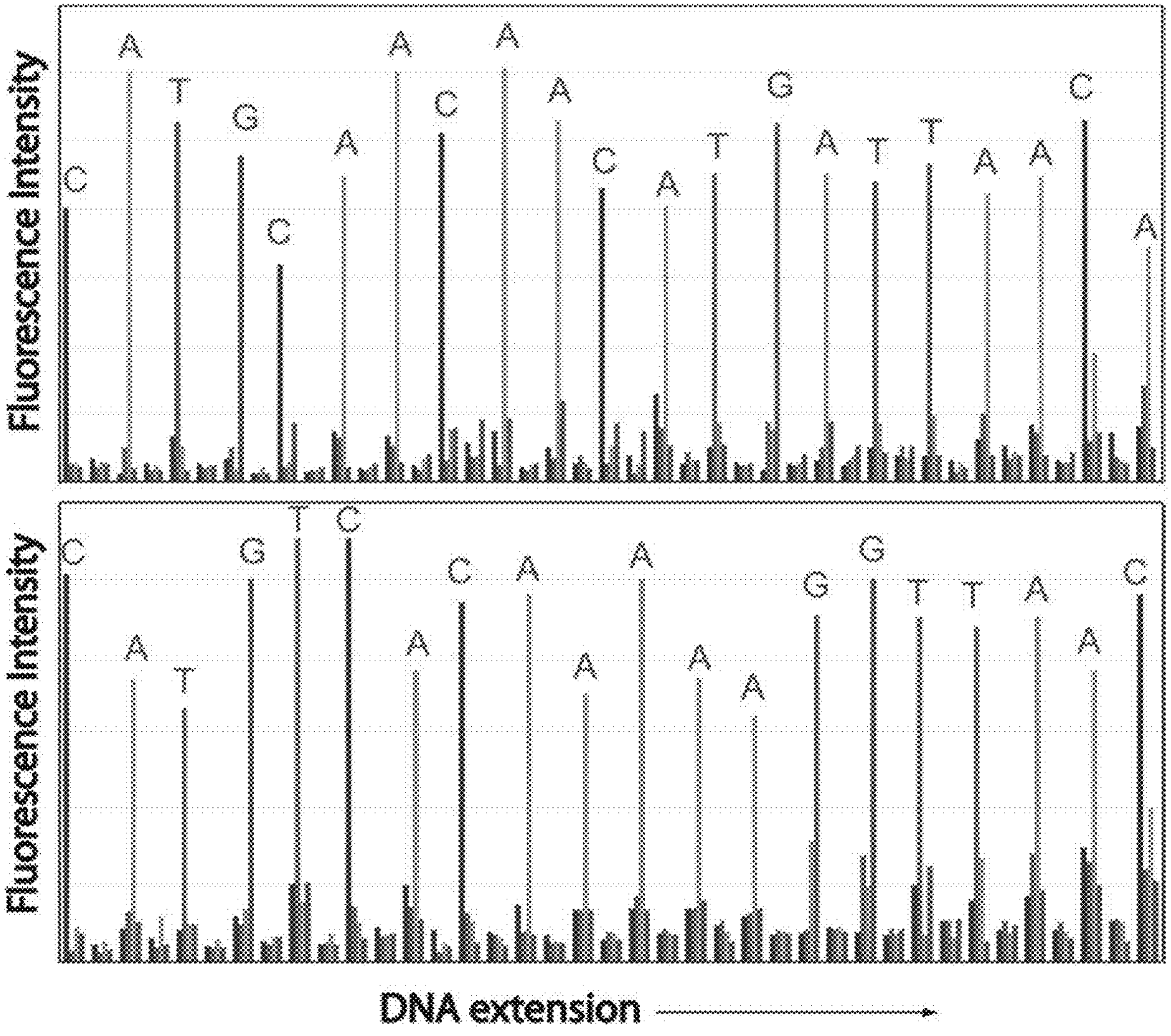
FIG. 22. A plot (four-color sequencing data) of raw fluorescence emission intensity obtained by using 3'-O-N3-dNTPs and ddNTP-$N_3$-fluorophores at the four designated emission wavelengths of the four cleavable fluorescent dideoxynucleotides.

The four-color images from a fluorescence scanner for each step of the hybrid SBS on a chip is shown in FIG. 21B, The first extension of the primer by the complementary fluorescent ddNTP, ddCTP-$N_3$-Bodipy-FL-510, was confirmed by observing a blue signal (the emission from. Bodipy~FL~510) [FIG. 21B (1)]. After fluorescent signal detection, the surface was immersed in a TCEP solution to cleave both the fluorophore from the DNA product extended with ddNTP-$N_3$-fluorophores and the 3'-O-azidomethyl group from the DNA product extended with 3'-O—$N_3$-dNTPs. The surface of the chip was then washed, and a negligible residual fluorescent signal was detected, confirming cleavage of the fluorophore [FIG. 21B (2)]. This was followed by another extension reaction with the 3'-O—$N_3$-dNTP/ddNTP-$N_3$-fluorophore solution to incorporate the next nucleotide complementary to the subsequent base on the template. The entire process of incorporation, synchronization, detection, and cleavage was performed multiple times to identify 32 successive bases in the DNA template. The plot of the fluorescence intensity vs. the progress of sequencing extension (raw four-color sequencing data) is shown in FIG. 21C. The DNA sequences are unambiguously identified with no errors from the four-color raw fluorescence data without any processing. Similar four color sequencing data were obtained for a variety of DNA template (FIG. 22)

Strategy 1: Template "Walking" by Unlabeled Nucleotides

Figure 23:
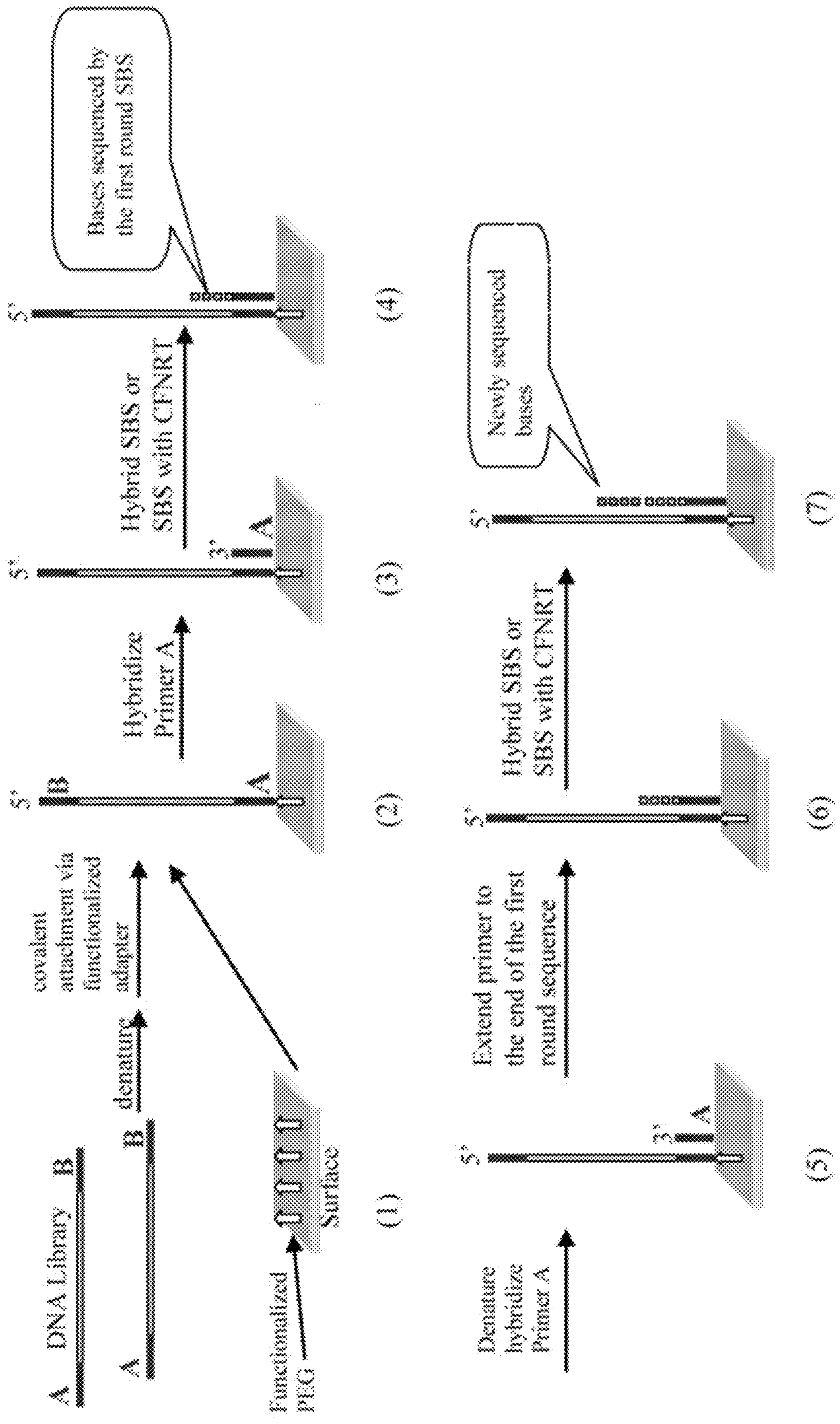
FIG. 23. "Walking" Strategy 1

The fundamental rationale behind this template "walking" strategy is the removal of the sequenced strand and reattaching of the original primer to allow the extension, or walking, of the template with a combination of natural and modified nucleotides to the end of the first round sequence so that SBS can be carried out from that point. Since the original sequenced strand is stripped away, including those terminated with ddNTPs, all the templates become available for "walking". Given that "walking" is carried out with either natural or 3'-modified nucleotides, the subsequent round of SBS is performed on nascent DNA strands for maximum read length. The advantage of template "walking" is its ability to restore all the templates after the denature step, includes those that are terminated with ddNTPs, so the next cycle of SBS can restart with potentially the same amount of nascent DNA as the previous round. The "walking" methodology is applicable to both hybrid SBS and SBS with C—F—NRTs, and has the potential to dramatically increase the read lengths of these SBS technologies (FIG. 23).

Template "Walking" for Hybrid SBS

1. Hybrid SBS (1st Round)

Figure 26:
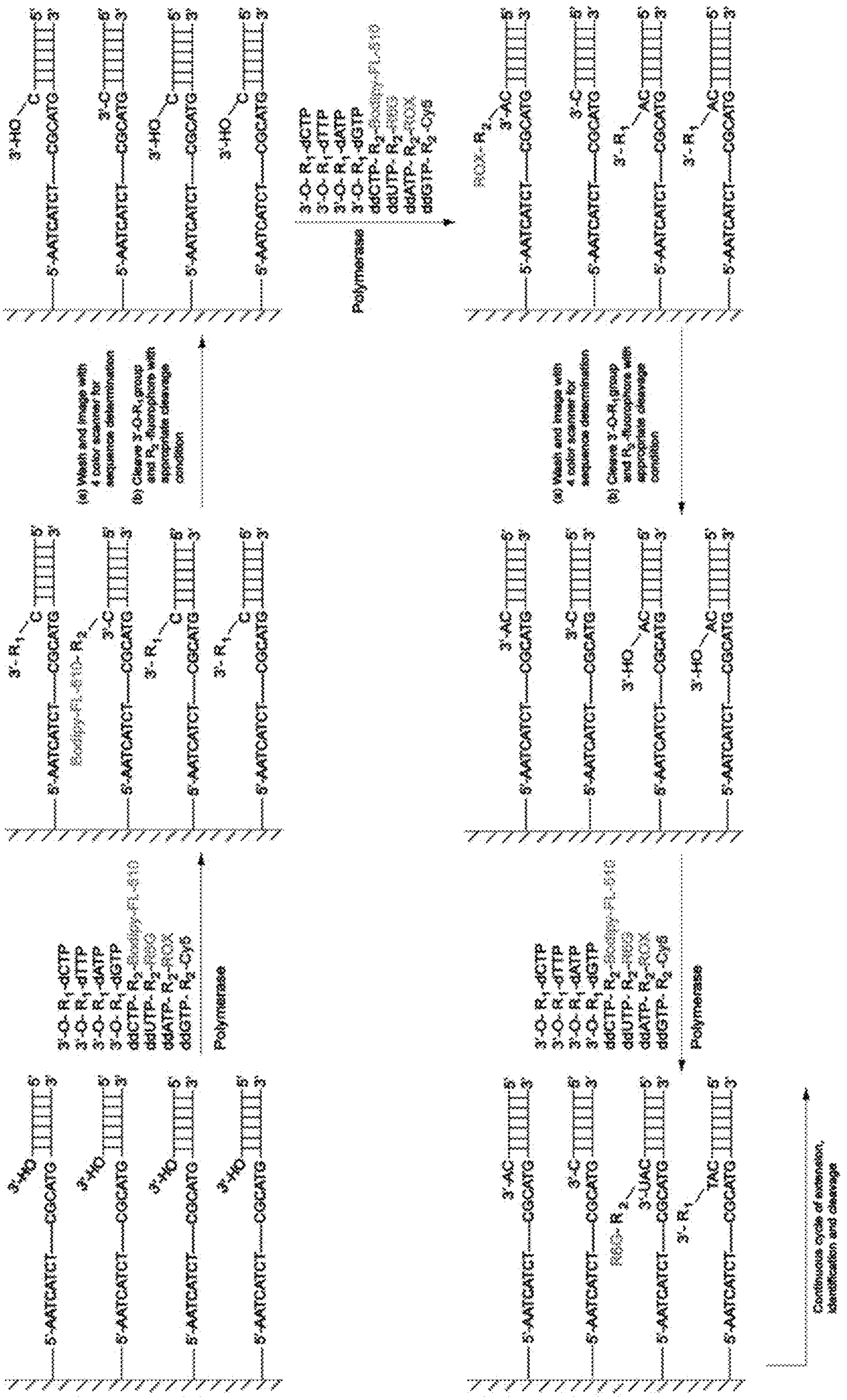
FIG. 26. Hybrid SBS scheme

DNA sequencing by synthesis (SBS) on a solid surface during polymerase reaction offers a paradigm to efficiently decipher multiple DNA sequences in parallel. Hybrid SBS is a hybrid DNA sequencing method between the Sanger dideoxy chain terminating reaction and SBS. In this approach, four nucleotides (FIG. 24) modified as reversible terminators by capping the 3'-OH with a small reversible moiety so that they are still recognized by DNA polymerase as substrates to extend the DNA chain, are used in combination with a small percentage of four cleavable fluorescent dideoxynucleotides (FIG. 25) to perform SBS. Sequences are determined by the unique fluorescence emission of each fluorophore on the DNA products terminated by ddNTPs, while the role of the 3'-O-modified dNTPs is to further extend the DNA strand to continue the determination of the DNA sequence. Upon removing the 3'-OH capping group from the DNA products generated by incorporating the 3'-O-modified dNTPs and the fluorophore from the DNA products terminated with the ddNTPs, the polymerase reaction reinitiates to continue the sequence determination (FIG. 26). Such incorporation, fluorescence measurement and dye removal is repeatedly conducted until the detectable fluorescence intensity is not distinguishable, indicating a situation in which all the elongated primers are terminated with ddNTP. To overcome this "halted sequencing" due to ddNTP termination, a "walking" step is carried out to reset the templates.

2. Template "Walking"

Immediately after the first round of SBS, all of the elongated primers ended terminated with ddNTPs are removed from the template by denaturing. The templates are freed again and available for further sequencing reactions. To achieve template "walking", the same starting primer is annealed to the template again and enzymatic incorporation is conducted to fill the gap between first and second stages of SBS. Five strategies are available for the walking process. Each approach has its advantages and shortcomings, which are summarized in the following.

Figure 27:
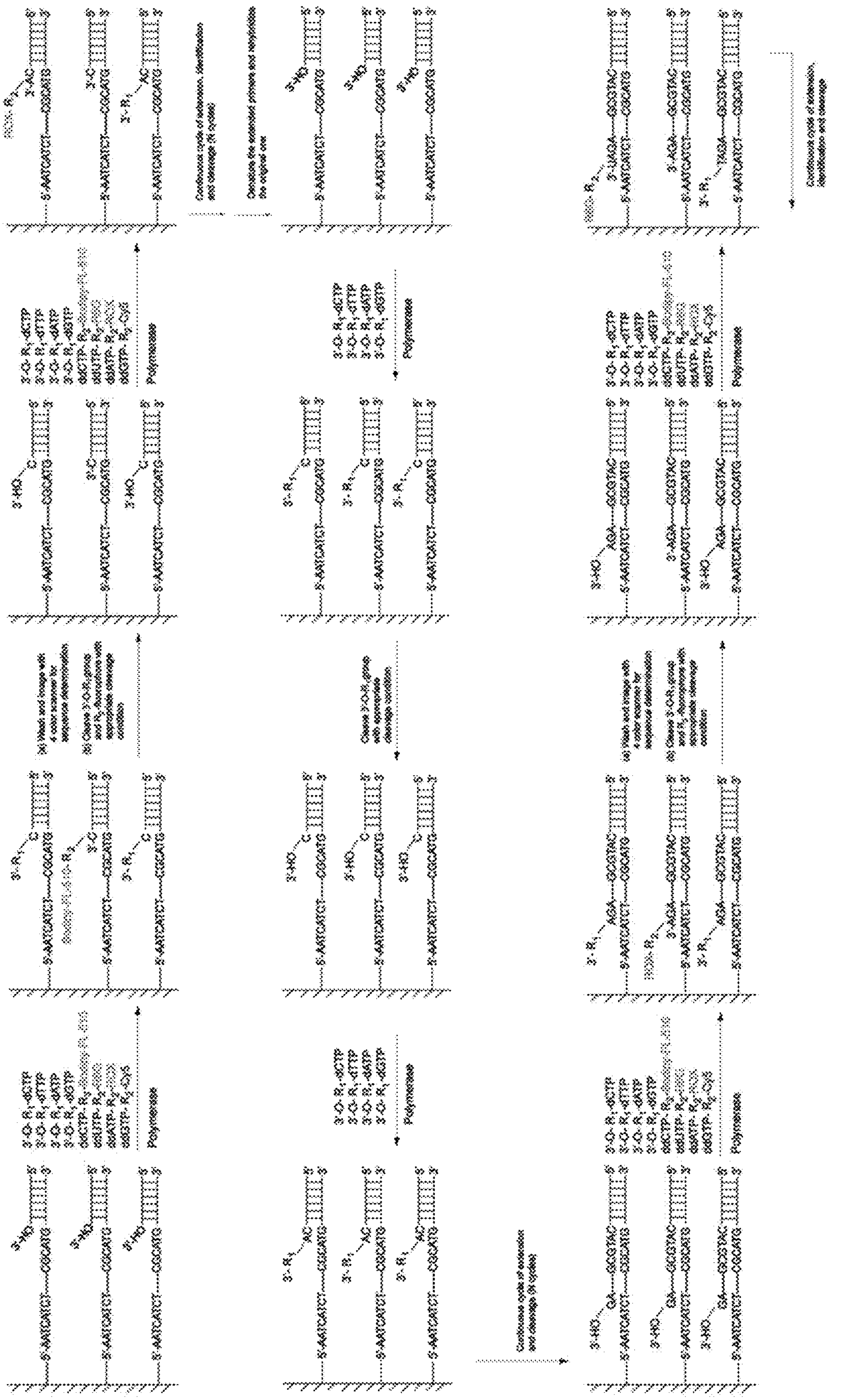
FIG. 27. Template "Walking" Method 1

Method 1. Nucleotide reversible terminators (3'-O—$R_1$-dNTPs) are used as substrates to perform enzymatic incorporation (FIG. 27). After incorporation, specific chemical reaction is applied to regenerate 3'-OH to ensure the subsequent incorporation. The number of repeated cycles of such incorporation and cleavage will exactly match the actual read length in the first stage of SBS, so that this "filling gap" incorporation stops at the same point where the longest ddNTP primer reaches.

Figure 28:
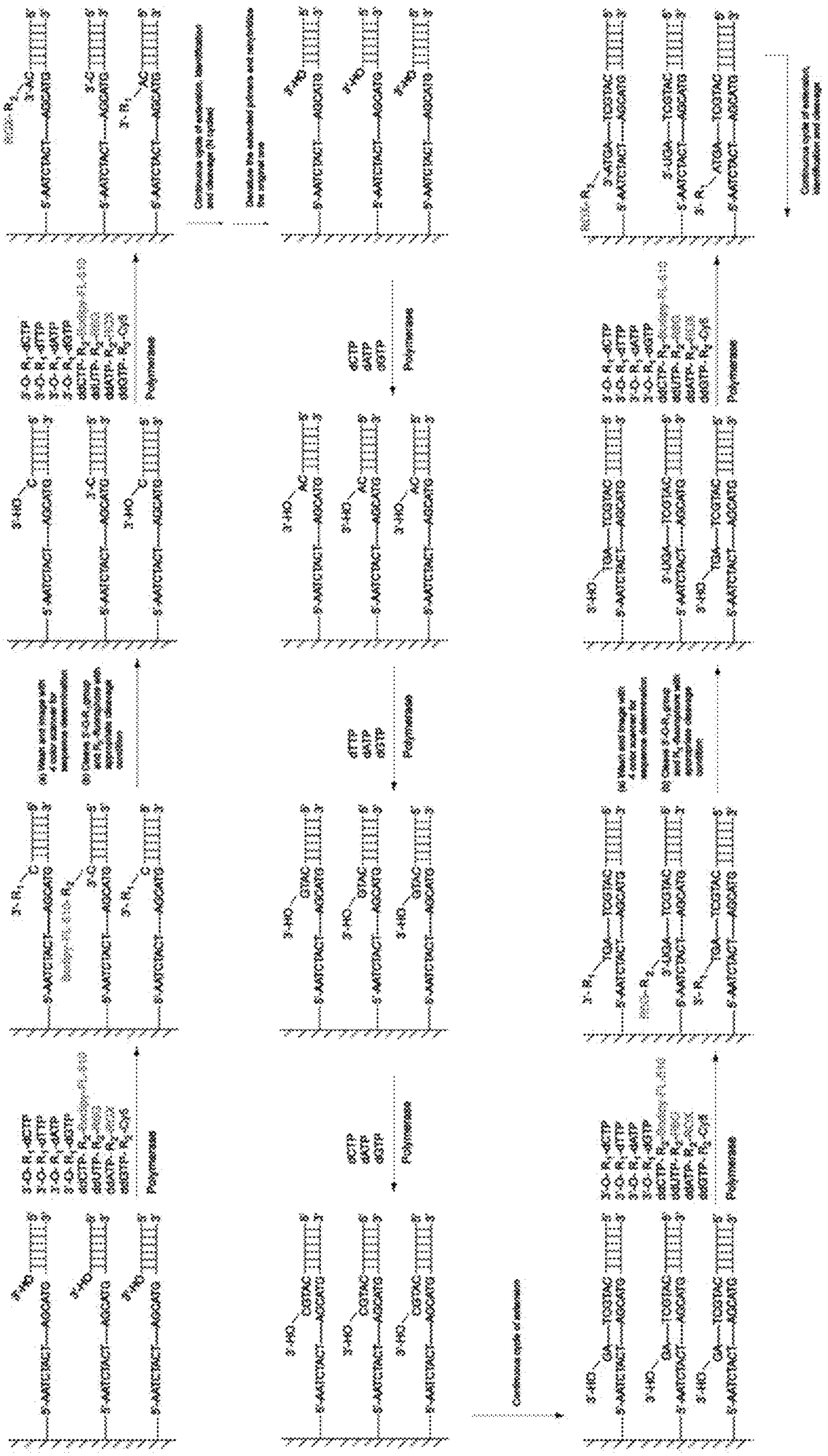
FIG. 28. Template "Walking" Method 2

Methods 2, 3, and 4. Enzymatic incorporation is conducted using two sets of nucleotides as substrates (FIG. 28). For example, the first set of nucleotides composed of dCTP, dATP, and dGTP (sans dTTP) was used to perform incorporation, so that the polymerase reaction stops once it reaches a base "A" in template. Then enzymatic incorporation is resumed with the second set of nucleotides composed of dTTP, dATP, and dGTP (sans dCTP), resulting in a polymerase reaction that stops at the base "G" in template. The repeated cycles of such incorporations fill the gap between first and second stages of SBS.

Figure 29:
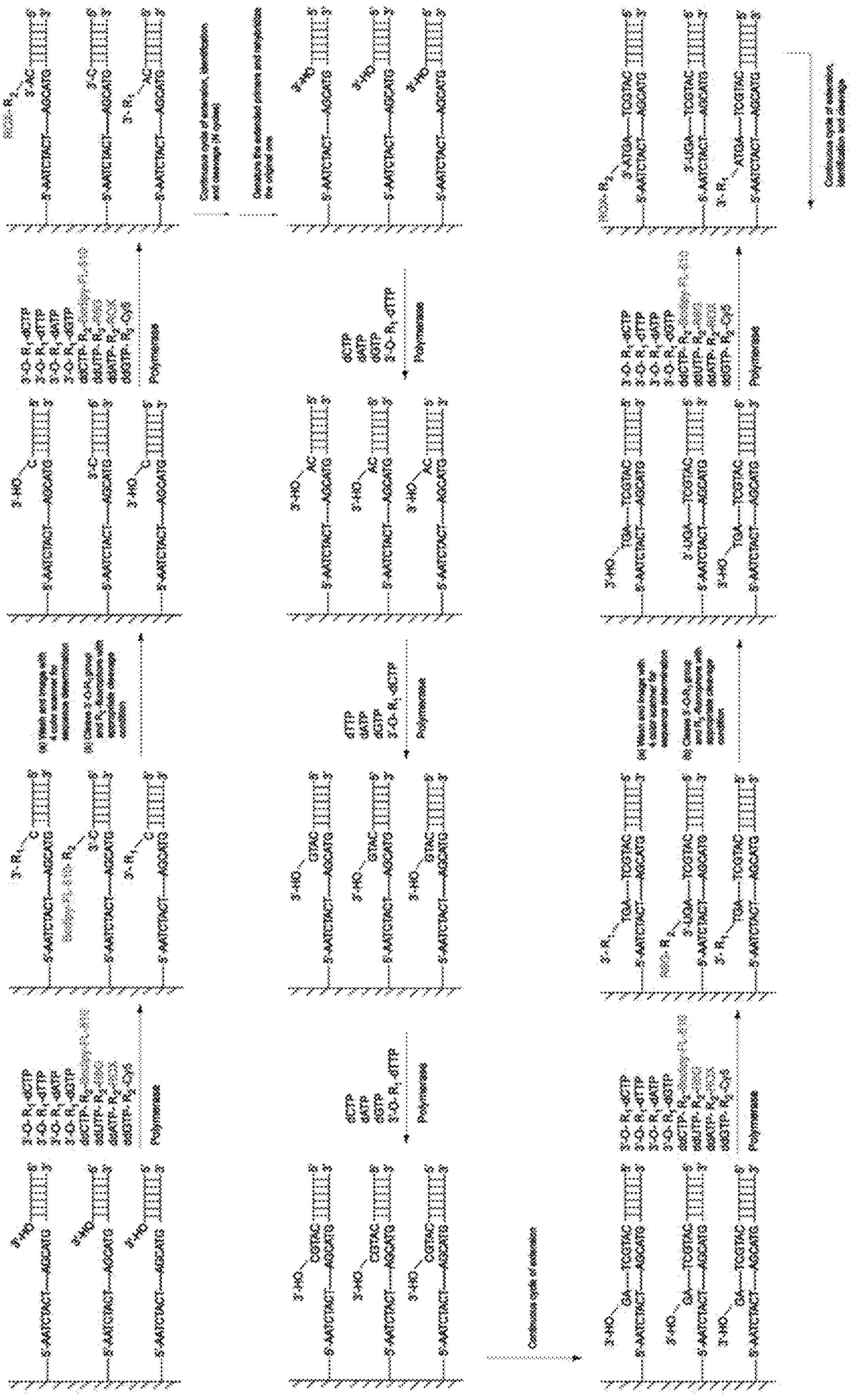
FIG. 29. Template "Walking" Method 3
Figure 30:
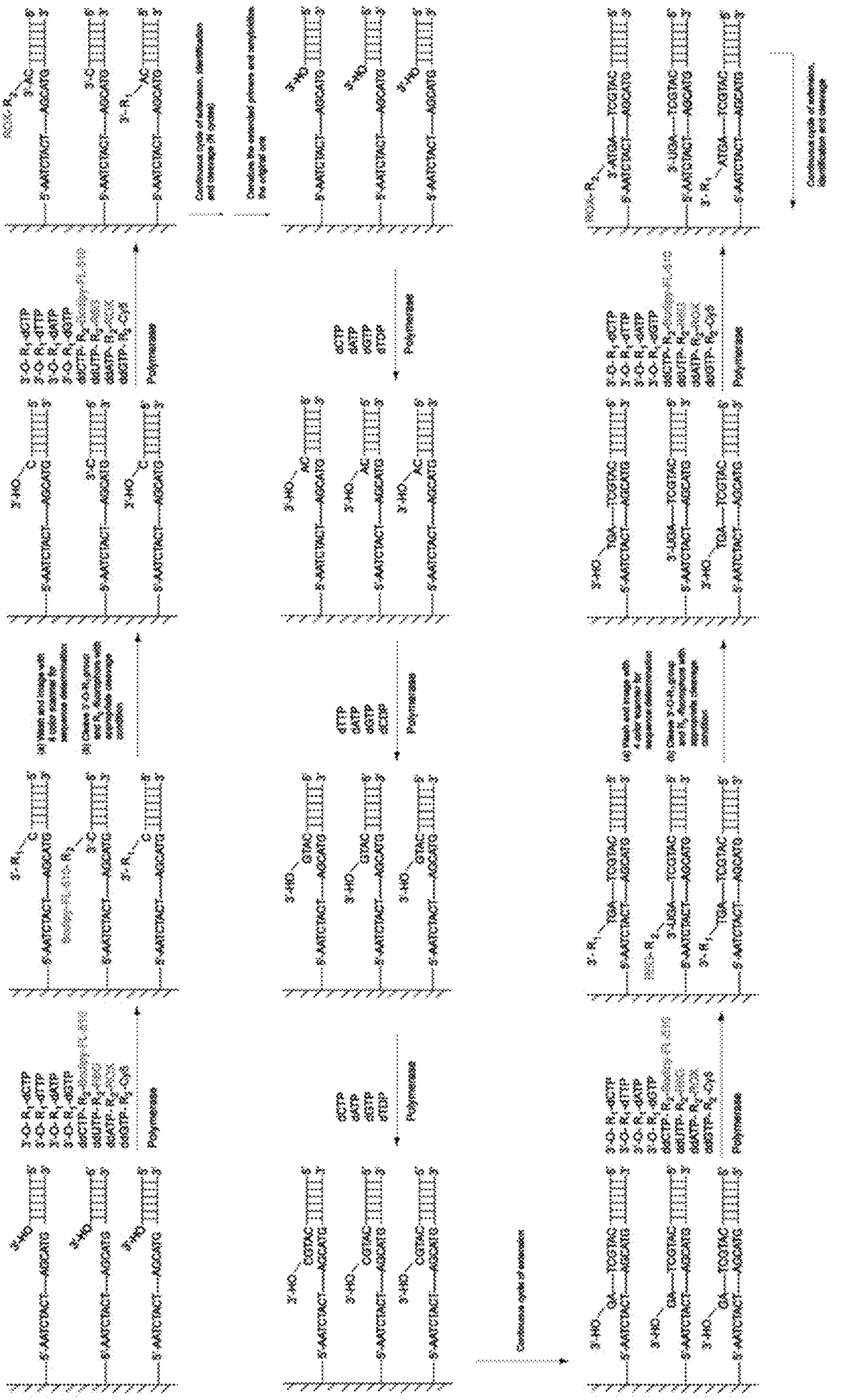
FIG. 30. Template "Walking" Method 4

To minimize the mis-incorporation rate, another enzyme substrate which can be recognized but not incorporated by the polymerase is assigned to each set of nucleotides. For instance, if the DNA polymerase used can only incorporate dNTP but not 3' blocked nucleotides, 3'-O—$R_1$-dTTP will be combined with dCTP, dATP and dGTP as the first set, while 3'-O—$R_1$-dCTP will be combined with dTTP, dATP and dGTP as the second set to elongate the primer (FIG. 29). Alternatively, deoxyribonucleotides diphosphate can also play such role, replacing the 3'-O—$R_1$-dNTPs, during enzymatic incorporation (FIG. 30).

Figure 31:
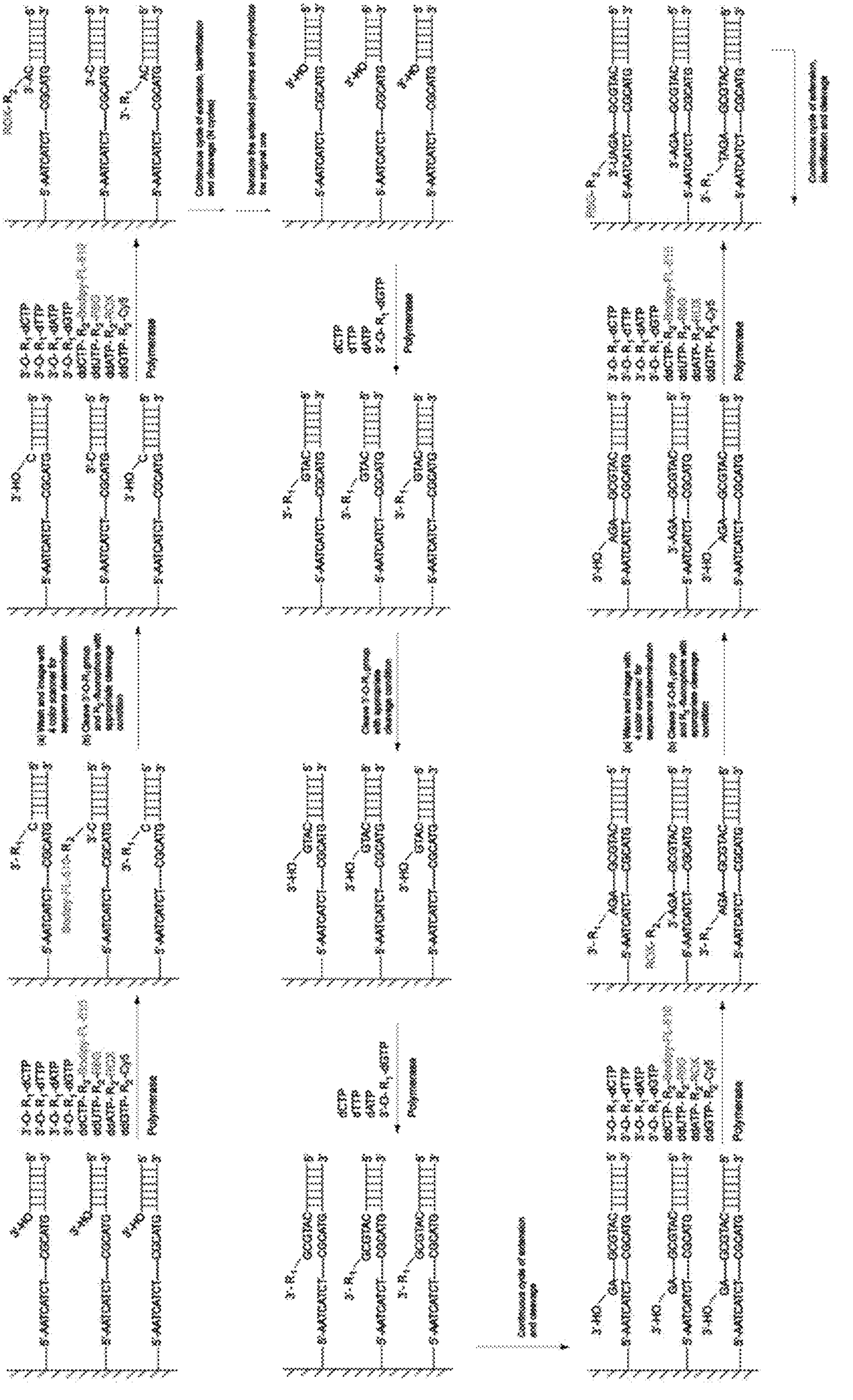
FIG. 31. Template "Walking" Method 5

Method 5. Enzymatic incorporation is conducted using three dNTPs and another nucleotide reversible terminator as substrates (FIG. 31). Primer elongation will only be stopped once it incorporates nucleotide reversible terminator. After incorporation, specific chemical reaction is applied to regenerate 3'-OH which ensure consecutive incorporation of the next round. Repeated cycles of such incorporation and cleavage will fill the gap between first and second stages of SBS.

3. Re-Initiation of Hybrid SBS

Once the "walking" process is completed, the second stage of SBS is conducted using mixture of nucleotide reversible terminators and fluorescently labeled dideoxynucleotides as incorporation substrates same as described above. Another cluster of bases on the template can be continuously revealed, leading to the doubling of the original read length. The SBS-walking-SBS process is repeated to generate maximum read length.

Examples

1. Design and Synthesis of 3'-O-Modified NRTs and Cleavable Fluorescent Dideoxynucleotide Terminators for the Hybrid SBS Four 3'-O-azidomethyl-modified NRTs (3'-O—$N_3$-dNTPs) were synthesized and evaluated (FIG. 32) for use in the hybrid SBS approach. The 3'-O-modified NRTs containing an azidomethyl group to cap the 3'-OH on the sugar ring were synthesized based on similar method to that reported by Zavgorodny et al. The 3'-O-azidomethyl group on the DNA extension product generated by incorporating each of the NRTs is efficiently removed by the Staudinger reaction using aqueous Tris(2-carboxy-ethyl) phosphine (TCEP)

solution followed by hydrolysis to yield a free 3'-OH group for elongating the DNA chain in subsequent cycles of the hybrid SBS (FIG. 34A).

To demonstrate the feasibility of carrying out the hybrid SBS on a DNA chip, four cleavable fluorescent dideoxy-nucleotide terminators were designed and synthesized, ddNTP-$N_3$-Fluorophores (ddCTP-$N_3$-Bodipy-FL-510, ddUTP-$N_3$-R6G, ddATP-$N_3$—ROX and ddGTP-$N_3$-Cy5) (FIG. 33). The ddNTP-$N_3$-Fluorophore were used in combination with the four NRTs (FIG. 32) to perform the hybrid SBS. Modified DNA polymerases have been shown to be highly tolerant to nucleotide modifications with bulky groups at the 5-position of pyrimidines (C and U) and the 7-position of purines (A and G). Thus, a each unique fluorophore was attached to the 5 position of C/U and the 7 position of A/G through a cleavable linker. The cleavable linker is also based on an azido modified moiety as a trigger for cleavage, a mechanism that is similar to the removal of the 3'-O-azidomethyl group (FIG. 34B).

2. Four-Color DNA Sequencing on a Chip by the Hybrid SBS Approach

Figure 35:
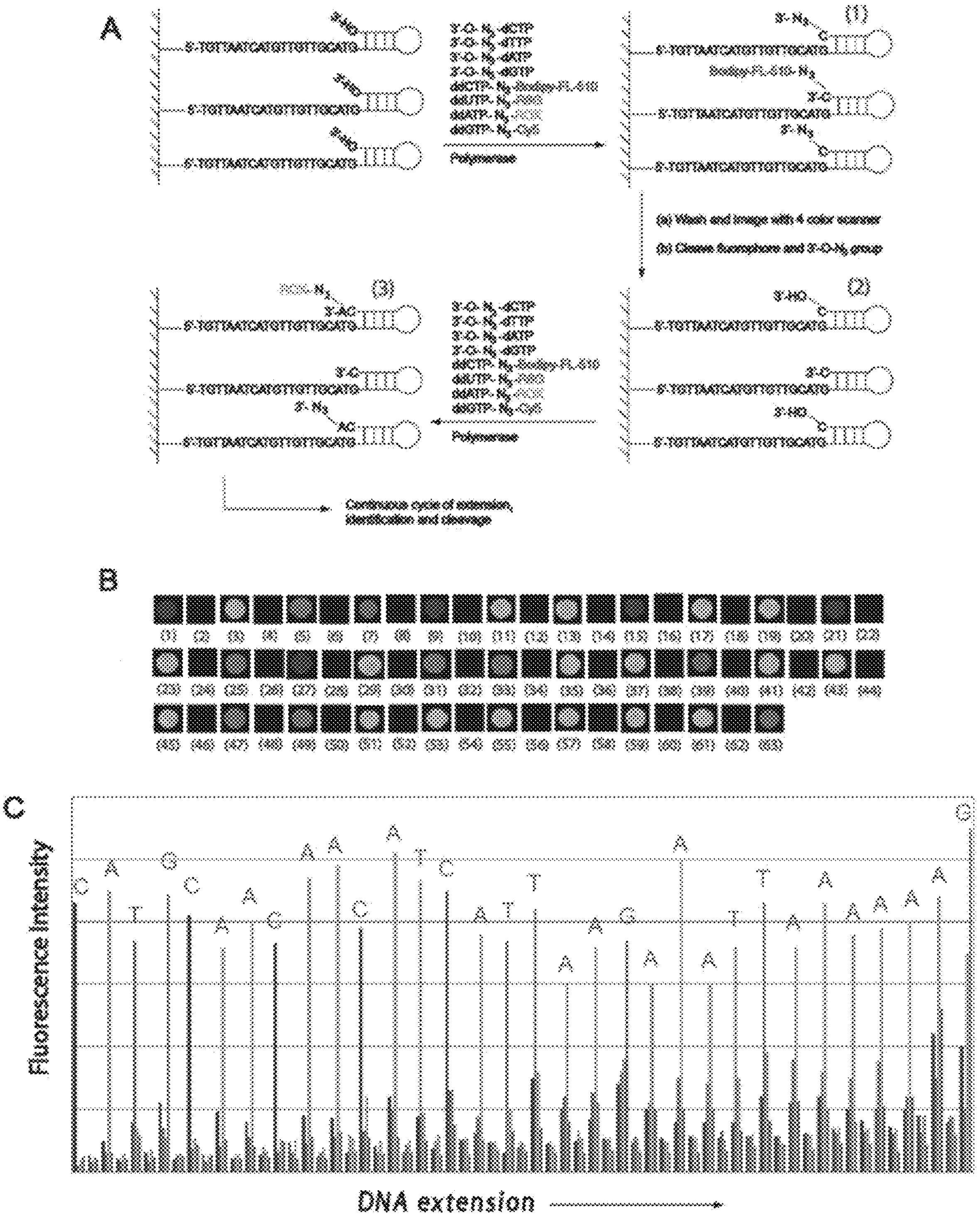
FIG. 35. Four-color DNA sequencing by the hybrid SBS approach
Figure 36:
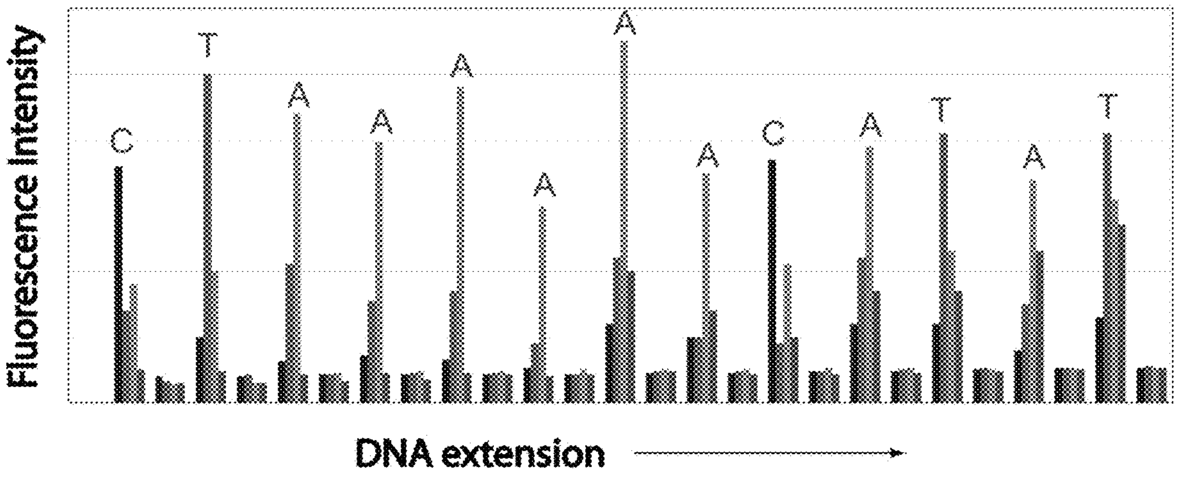
FIG. 36. Four-color DNA sequencing by the hybrid SBS after template "walking"

Hybrid SBS was performed on a chip-immobilized DNA template using the 3'-O—$N_3$-dNTP/ddNTP-$N_3$-fluorophore combination and the results are shown in FIG. 35. The general four-color sequencing reaction scheme on a chip is shown in FIG. 35. The de novo sequencing reaction on the chip was initiated by extending the self-priming DNA using a solution containing the combination of the four 3'-O—$N_3$-dNTPs and the four ddNTP-$N_3$-fluorophores, and 9°N DNA polymerase.

The four-color images from a fluorescence scanner for each step of the hybrid SBS on a chip is shown in FIG. 35. The entire process of incorporation, synchronization, detection and cleavage was performed multiple times to identify 32 successive bases in the DNA template. The plot of the fluorescence intensity vs. the progress of sequencing extension (raw 4-color sequencing data) is shown in FIG. 35. The DNA sequences were unambiguously identified with no errors from the 4-color raw fluorescence data without any processing.

3. Primer Reset and 2nd Round SBS

To demonstrate the concept of walking, the same self-priming DNA was immobilized on surface as template. After identifying the first 32 bases unambiguously with no errors by the first round hybrid SBS, the primer was reset for the second round SBS by elongating the original primer over the sequenced region via enzymatic incorporations. A solution containing dATP, dTTP, dCTP and 3'-O—$N_3$-dGTP was used to perform the polymerase reaction. 9°N DNA polymerase incorporates 3' unblocked nucleotides more efficiently, leading to certain percentage of primers not fully extended by 3'-O—$N_3$-dGTP. To minimize this effect, a synchronization step was added to reduce the amount of out-of-phase primers after the initial extension reaction. A synchronization reaction mixture consisting of just 3'-O—$N_3$-dGTP in relative high concentration was used along with the 9°N DNA polymerase. The 3'-O-azidomethyl group on the DNA extension product generated by incorporating 3'-O—$N_3$-dGTP was efficiently removed by using aqueous Tris(2-carboxy-ethyl) phosphine (TCEP) solution to yield a free 3'-OH group for elongating the DNA chain in subsequent cycles of enzymatic incorporation. The entire process of incorporation, synchronization and cleavage were conducted repeatedly until the sequenced bases during the first round SBS were "walked" over. After the primer was reset by the enzymatic incorporation, the second stage of SBS was conducted using mixture of nucleotide reversible terminators and fluorescently labeled dideoxynucleotides as incorporation substrates same as described above. Another 13 bases were successfully identified after template "walking" (FIG. 14).

Template "Walking" for SBS with CFNRTs

1. SBS with C—F—NRTs

Figure 37:
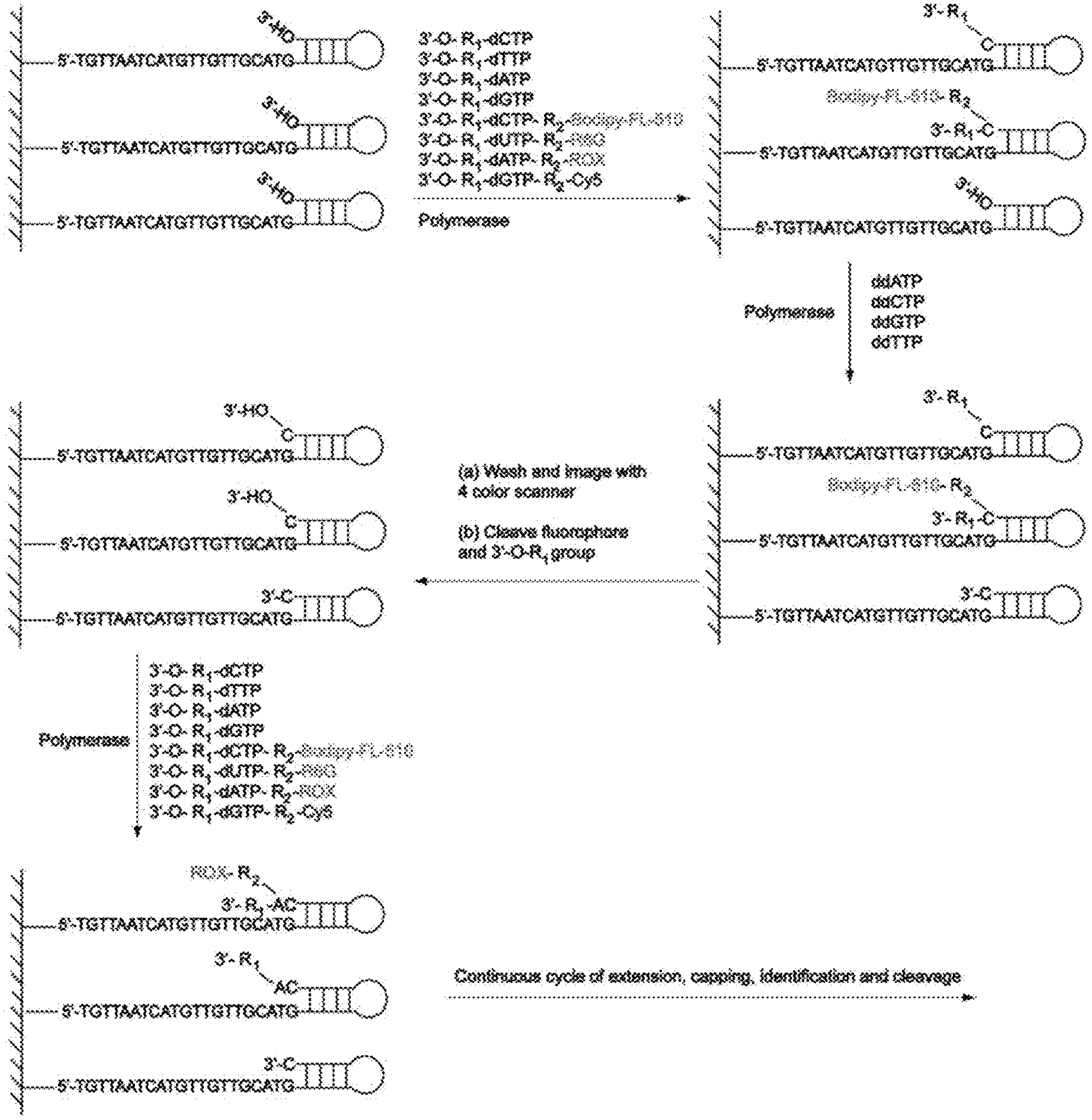
FIG. 37. General Scheme for SBS with C—F—NRTs

DNA sequencing by synthesis (SBS) on a solid surface during polymerase reaction offers a paradigm to efficiently decipher multiple DNA sequences in parallel. Disclosed is the development of a DNA sequencing method that involves the extension of target DNA strand with modified cleavable fluorescent nucleotide reversible terminators (C—F—NRTs, 3'-O—$R_1$-dNTPs-$R_2$-fluorophore) in combination with cleavable nucleotide reversible terminators (C-NRTs, 3'-O—$R_1$-dNTPs). A set of four C—F—NRTs is produced via dual modifications by capping the 3'-OH group with a small chemical moiety and tethering a fluorophore through a cleavable linker to either the 7-position of the purines (A, G) or the 5-position of the pyrimidines (C, T) so that they are still recognized as substrates by DNA polymerase. Another set of four C-NRTs is modified similarly as the C—F—NRTs except no fluorophore is attached, which results in a reduction of the size of C-NRTs and the increment of DNA polymerase incorporation efficiency. In this approach, an extension mixture composed of the C-NRTs with a small percentage of the C—F—NRTs is used to perform SBS. Sequences are determined by the unique fluorescence emission of each fluorophore on the DNA products terminated by the C—F—NRTs. Immediately following the detection step, a synchronization reaction is performed using only the C-NRTs to extend the un-extended DNA strands. A dideoxynucleotides (ddNTPs) capping step is carried out afterwards to completely rid of the remaining un-extended DNA. Upon removing the 3'-OH capping group from the DNA products generated by incorporating both C—F—NRTs and C-NRTs and the fluorophore from the C—F—NRTs, the polymerase reaction reinitiates to continue the sequence determination. The following scheme (FIG. 37) illustrates the general process for SBS with C—F—NRTs.

Figure 39:
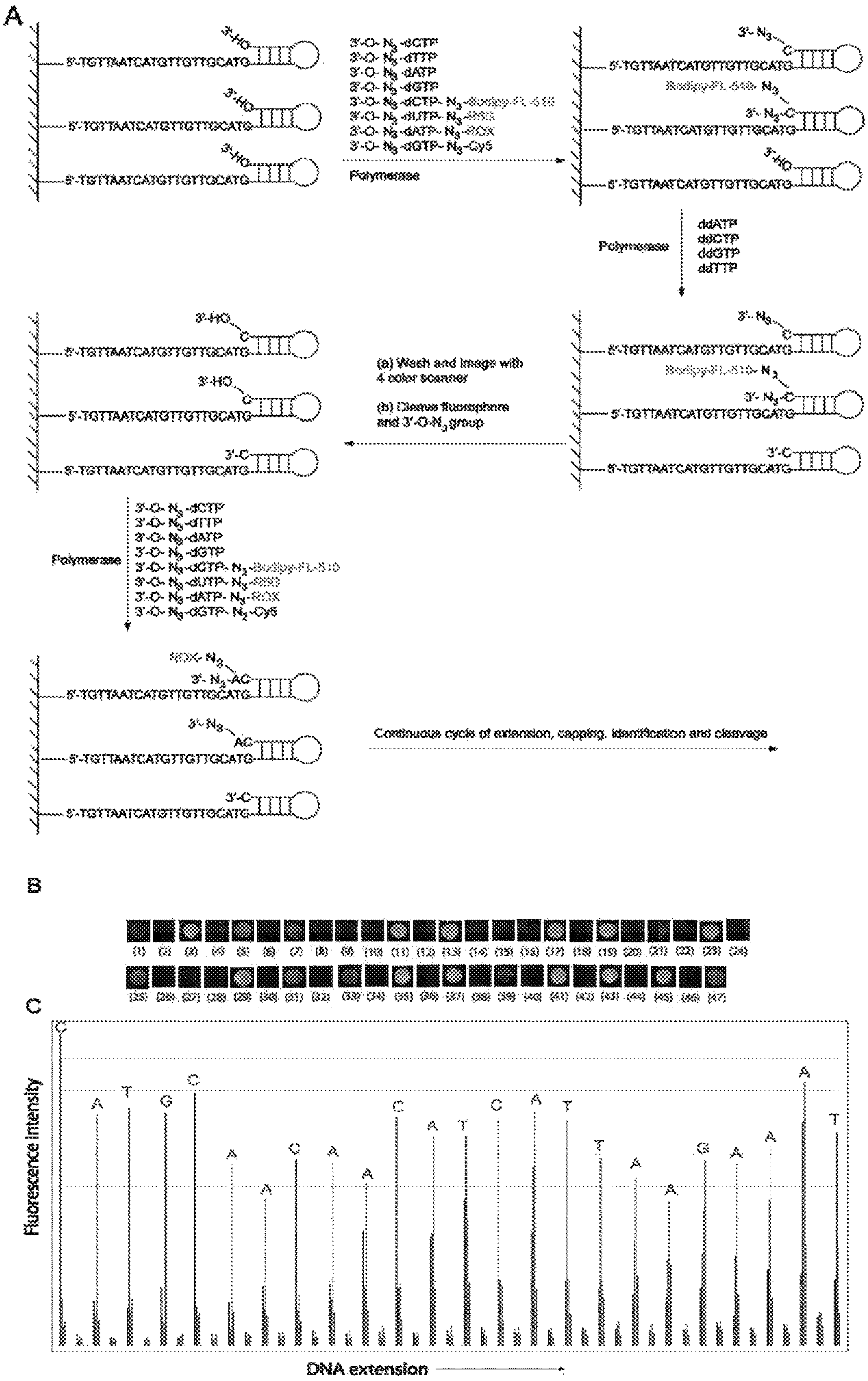
FIGS. 39A-C. Four-color DNA SBS with 3'-O—$N_3$-dNTPs-$N_3$-fluorophore.
Figure 40:
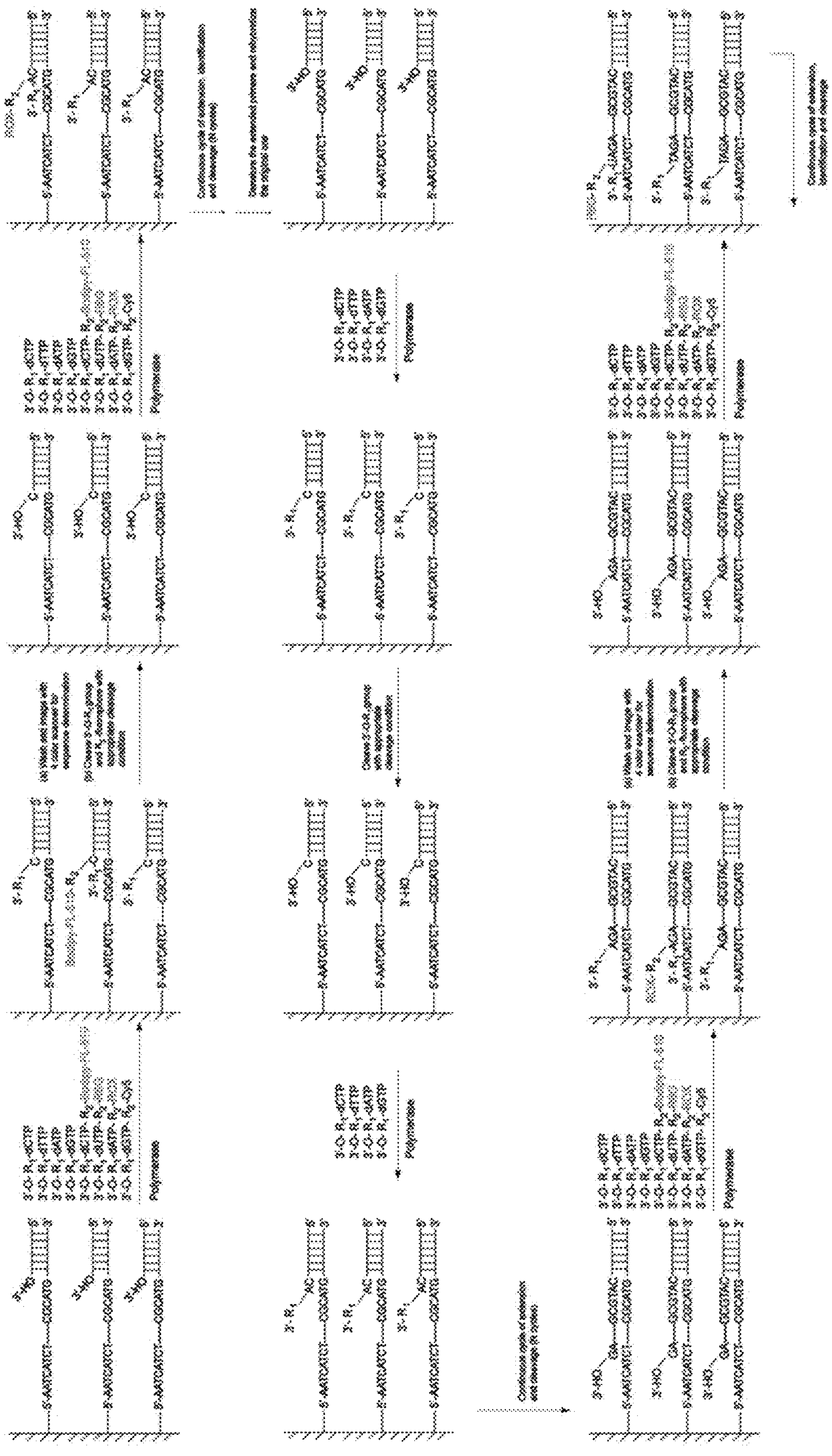
FIG. 40. Template "Walking" Method 1 for SBS with C—F—NRTs
Figure 41:
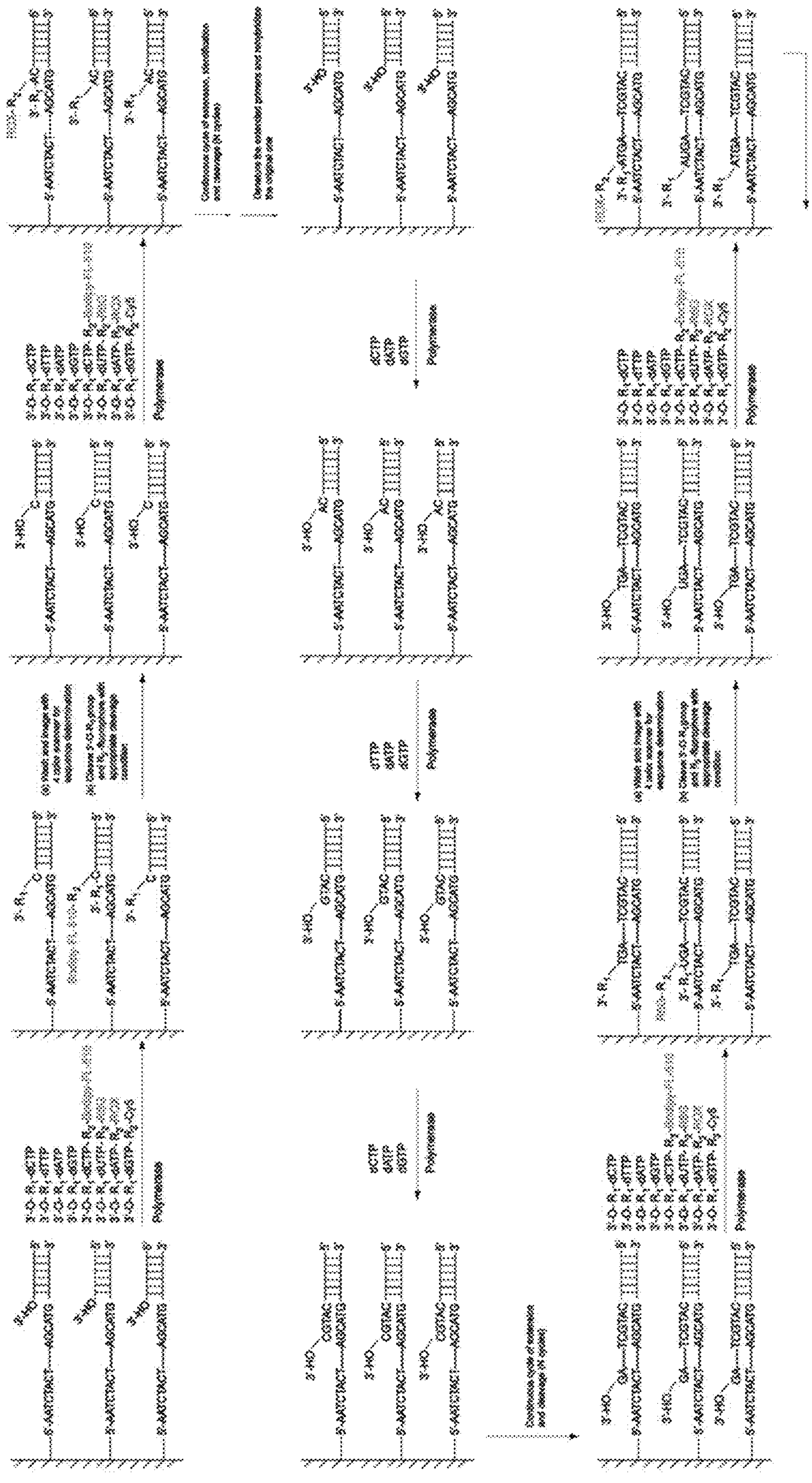
FIG. 41. Template "Walking" Method 2 for SBS with C—F—NRTs
Figure 42:
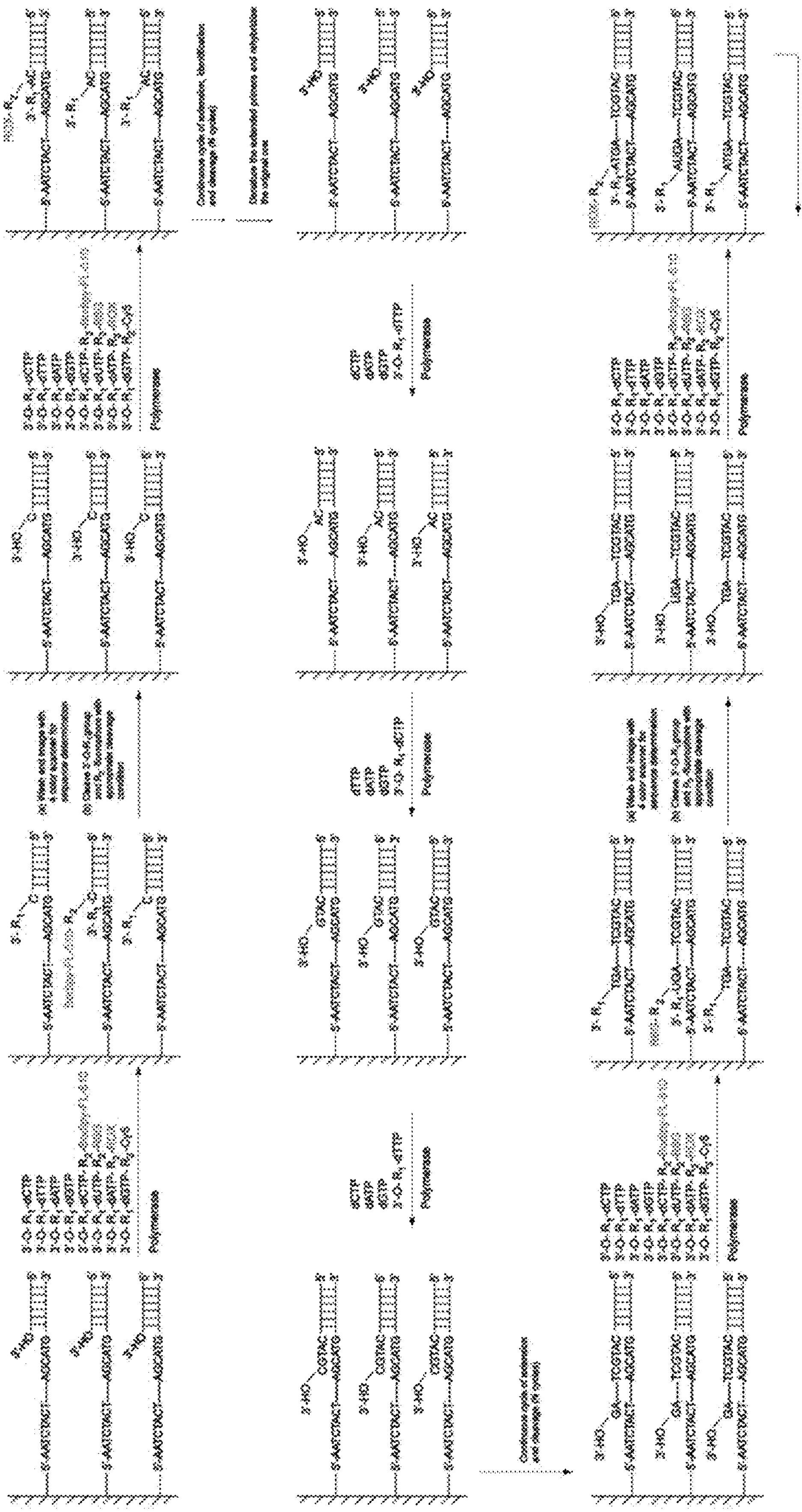
FIG. 42. Template "Walking" Method 3 for SBS with C—F—NRTs
Figure 43:
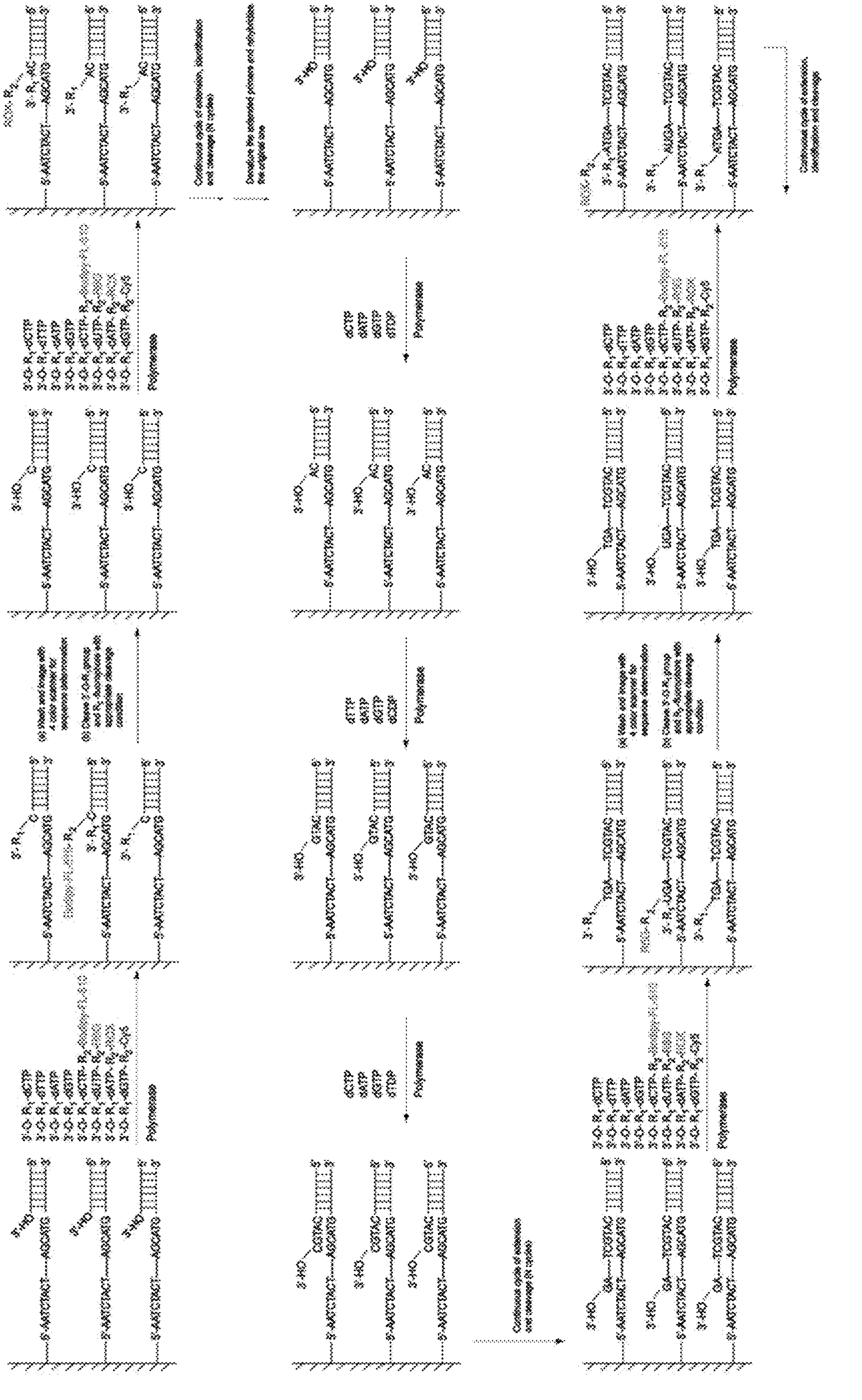
FIG. 43. Template "Walking" Method 4 for SBS with C—F—NRTs
Figure 44:
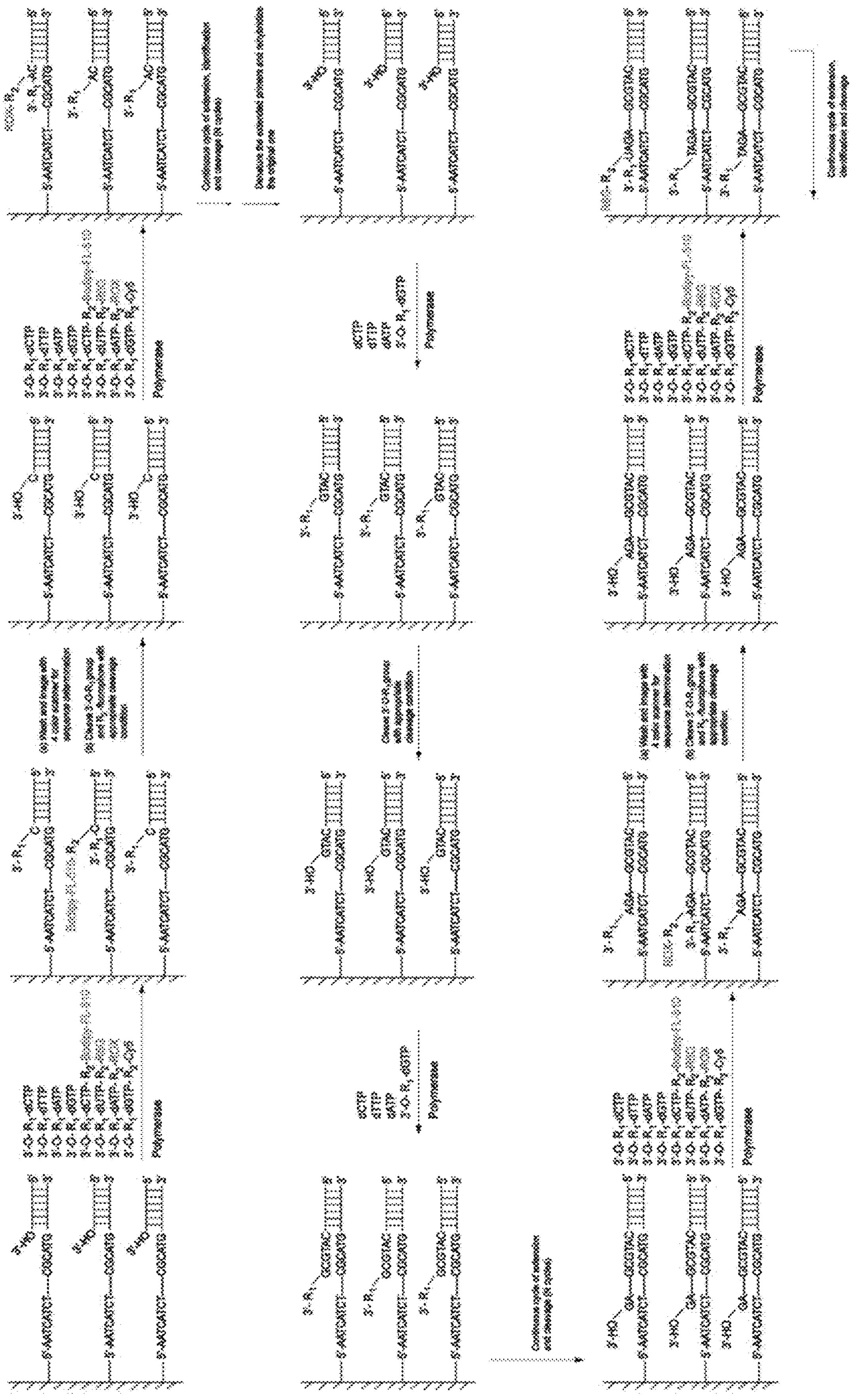
FIG. 44. Template "Walking" Method 5 for SBS with C—F—NRTs

Four 3'-O—$N_3$-dNTPs-$N_3$-fluorophore (FIG. 38) and four 3'-O—$N_3$-dNTPs (FIG. 32) were synthesized, using an azidomethyl group as a chemically reversible capping moiety in the 3'-O-modified C—F—NRTs and C-NRTs, and an azido-based cleavable linker to attach the fluorophores to the C—F—NRTs, After fluorescence detection for sequence determination, the azidomethyl capping moiety on the 3'-OH and the fluorophore attached to the DNA extension product via the azido-based cleavable linker are efficiently removed using tris(2-carboxyethyl)phosphine (TCEP) in aqueous solution compatible with DNA. Various DNA templates, including those with homopolymer regions were accurately sequenced with read length of over 20 bases using this SBS method on a chip and a four-color fluorescent scanner (FIG. 39).

Four C—F—NRTs (3'-O—$N_3$-dNTPs-$N_3$-fluorophore) were synthesize along with four C-NRTs (3'-O—$N_3$-dNTPs) for the implementation of our four-color de novo DNA sequencing by synthesis approach. During the incorporation stage of SBS, a mixture of the two sets of NRTs is used to extend the DNA strand. Only a small percentage of the 3'-O—$N_3$-dNTPs-$N_3$-fluorophore is used in the mixture so that the majority of the product is extended with the less bulky 3'-O—$N_3$-dNTPs. This approach leads to a more efficient DNA polymerase reaction since the smaller 3'-O—$N_3$-dNTPs are much easier to incorporate. Another advantage of having most of the DNA extended with 3'-O—$N_3$-dNTPs is the fact that after cleavage of the 3'-OH capping group on the product, nascent strand of DNA that have no traces of modification is restored. Such DNA does not have any adverse effect on the DNA polymerase during the subsequent incorporation of the complementary nucleotide. For DNA extended with the 3'-O—$N_3$-dNTPs-$N_3$-fluorophore, which serve as the signal producer, the 3'-OH is also restored after the cleavage step so that the next stage of SBS can be carried out. Therefore, it is possible to recover all the DNA templates after each round of sequencing, dramatically increasing the potential read-length of our SBS methodology. After the incorporation reaction, two separate capping steps, first with 3'-O—$N_3$-dNTPs and then with ddNTPs, are performed. The rationale behind the first capping reaction is to maximize the amount of extension products and to ensure the minimal loss of templates. In case there is any un-extended product after the first capping step, the second capping with ddNTPs is mostly likely to permanently terminate these DNA strands so that all templates are synchronized. Without these precautionary synchronization procedures, mixed fluorescent signals will prevent the identification of the correct nucleotide incorporated. Since both 3'-O—$N_3$-dNTPs-$N_3$-fluorophore and 3'-O—$N_3$-dNTPs are reversible terminators, which allow the sequencing of each base in a serial manner, they can accurately determine the homopolymeric regions of DNA. In addition, due to the fact that all of the steps of our SBS approach are performed on a DNA chip, there is no longer a need for electrophoretic DNA fragment separation as in the classical Sanger sequencing method.

Even though theoretically SBS with C—F—NRTs can be executed without losing templates, the utilization of ddNTPs capping does reduce the number of available templates during the actual sequencing reaction. In addition, the incorporation and cleavage of C—F—NRTs leave a tail on the modified nucleotides that can potentially reduce the incorporation efficiency the subsequent base. Hence template "walking" can be applied to increase read length for this SBS methodology.

2. Template "Walking"

Immediately after the first round of SBS, DNA templates are denatured by heat or mild alkali conditions to rid of the extended primer. The same original primer is re-hybridized to the template chain, and one of the five "walking" methods described in the previous section can be applied to reset the start point for the next round of SBS at the end of the first sequencing run (FIGS. 40, 41, 42, 43, and 44).

3. Re-Initiation of SBS with C—F—NRTs

Once the "walking" process is completed, the primer is extended to the end of the previous round of SBS. At this point, hybrid SBS is carried out to identify the subsequent bases. If the process can be repeated more times, it should be theoretically possible to achieve long and significant read length.

Strategy 2: Template "Walking" with Universal Bases

Figure 45:
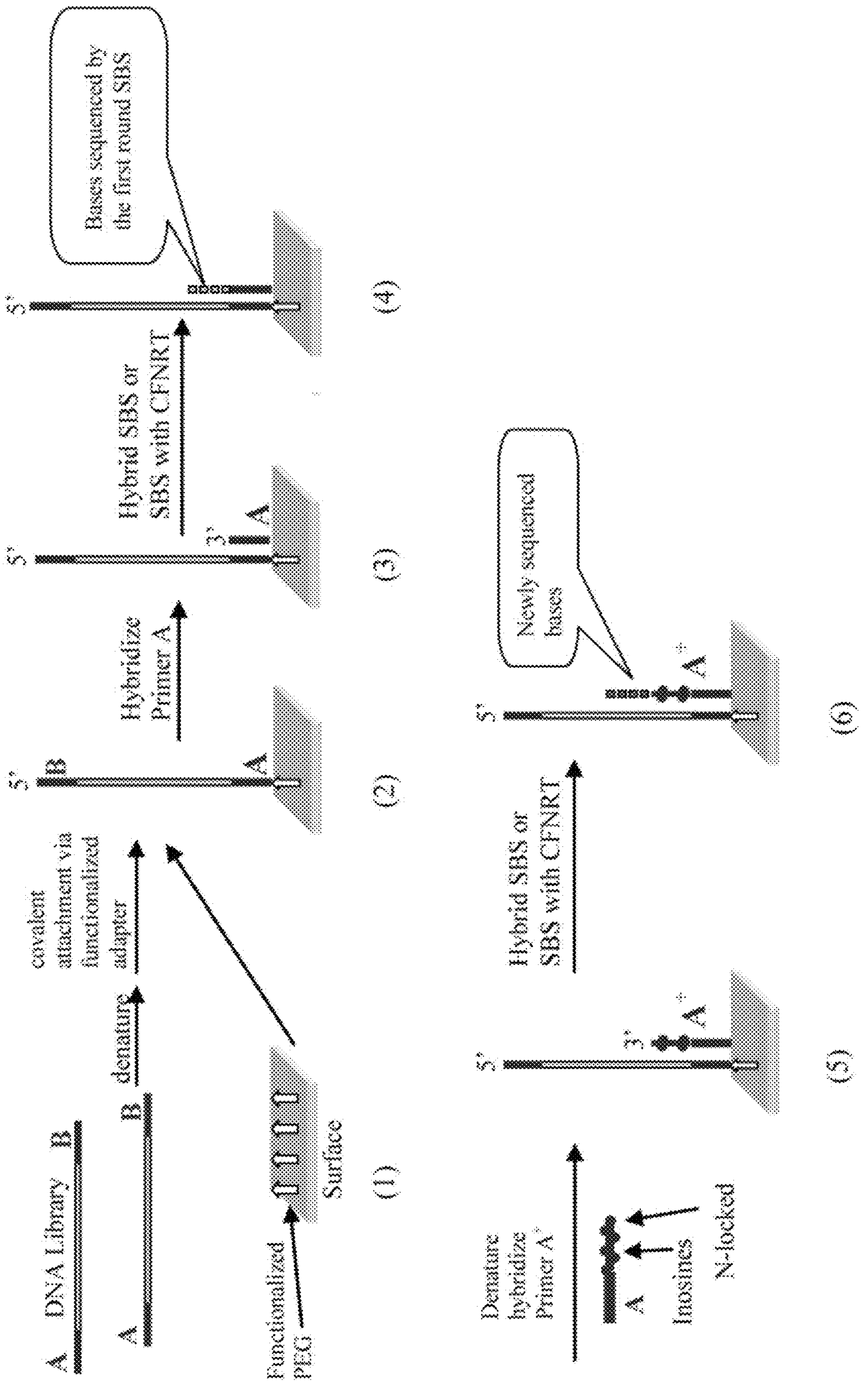
FIG. 45. "Walking" Strategy 2

In this variation on the Strategy 1, the reset is achieved not with nucleotide walking, but with the use of a longer primer partially consisting of universal nucleotides for the second round. Attachment of the template DNA to the surface and the first few steps of the procedure are identical to the first method. However, after stripping the first extended primer for the initial 20 base readout, a long primer with the following features will be hybridized to the template: (a) the first half is identical to the initial primer; (b) the second half is composed almost entirely of universal bases. One possible candidate for the universal base is inosine, which, in its deoxynucleoside form, can base pair with all four nucleotides, though its affinity for C and A is significantly higher than for G and T; a second possibility is 5-nitroindole; (c) the last one or two anchoring bases of the long primers are degenerate with each of the four possible bases being represented. Because the universal bases can form hydrogen bonds with any of the other four bases with some efficiency, they have the capacity to bind to the first 20 or so bases of the sequence. However, the melting temperature of the ensuing hybridization is reduced substantially by the run of inosines, a few of the bases in the first half and the two 3'-anchoring bases can be substituted with locked nucleotides. Locked nucleic acids have a chemical bond between the 2' and 4' carbons of the ribose. While slower to associate with their complementary base, once hybridized, they tend not to dissociate. Thus, they provide a nice solution to ensure that the long primer remains attached appropriately to the template. In addition, the percentage of locked nucleosides in the primer can be manipulated to achieve higher hybridization strength. After hybridization of the above long primer, a second round of either Hybrid SBS or SBS with C—F—NRTs can be performed (FIG. 45).

An alternative approach to Strategy 2 is the use of a detachable loop primer, possibly with a labile sugar and glycosylase treatment. After the first round of sequencing, the loop is removed by enzymatic cleavage and denaturation, and then a new identical loop is attached. In a modification that is a composite of "walking" Strategy 1 and 2, the new loop primer can be composed of an initial portion identical to the first loop primer, a "loop out" region that bypasses the first set of sequenced nucleotides, and a degenerate anchoring nucleotide to initiate the second round of sequencing.

Strategy 3: Multiple Primers "Walking"

In this third strategy, one or two additional primer annealing sites are introduced into the DNA to be sequenced at a distance just about equal to the number of bases that can be sequenced from the first primer.

Figure 46:
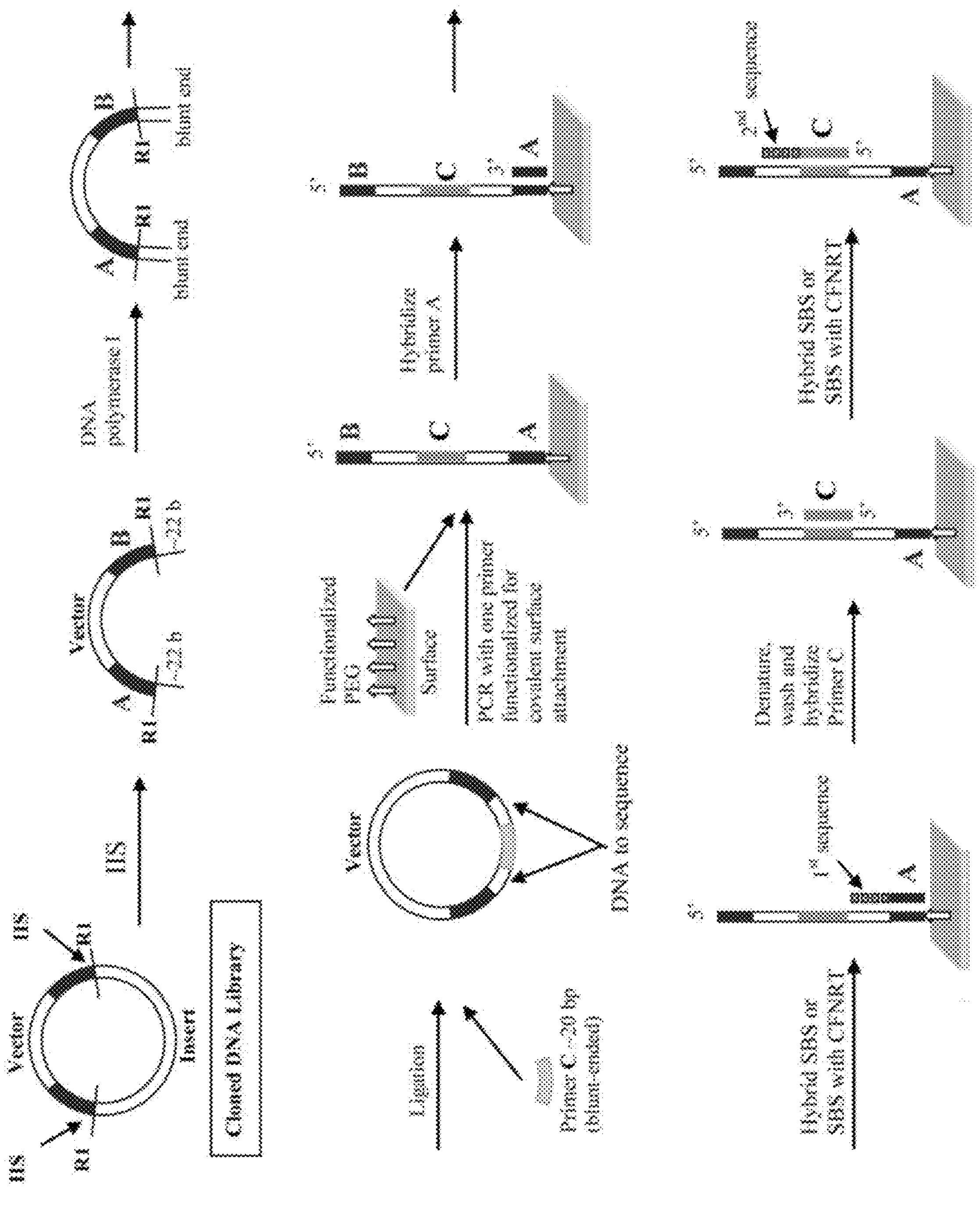
FIG. 46. "Walking" Strategy 3

As illustrated in FIG. 46, template preparation for SBS will utilize the cloning of genomic DNA into a specially designed vector containing type IIS or III restriction sites (MmeI and EcoP15 I) flanking the genomic DNA cloning site. In this procedure size fractionated DNA (minimal length 100 bp) will be ligated into the cloning vector using blunt-end ligation. Upon cloning, the resulting recombinant plasmids will be re-cut at one of the type IIS/III sites and the sticky ends will be filled in with Klenow enzyme. Next, specific sequencing primers will be introduced via ligation inside the genomic DNA inserts, 22 bases distant from the first primer in the case of MmeI or 27 bases away in the case of EcoP15 I. After insertion of the internal priming sites, the constructs will be re-cloned in *E. coli*, the recombinant plasmids isolated and the inserts re-amplified by PCR at vector-insert junctions and attached to the beads for sequencing. Alternatively, emulsion or polony PCR strategies can be used to accomplish attachment of single molecules to individual beads or slide locations and their subsequent amplification at a much lower cost than cloning. In any case, once the DNA is immobilized, the first round of Hybrid SBS or SBS with C—F—NRTs will be primed from the flanking primer, then after stripping these extended primers, the second set of sequencing reactions will be initiated at the internal primer. It should be noted that with this scheme, the two sequenced portions come from opposite ends of the initial DNA, and are in essence paired end reads.

Several novel modifications of this approach can address the desire of many investigators to sequence an entire 100-base stretch of DNA, the length of a typical exon including surrounding intronic bases adjacent to the splice site. For instance, one can prepare a construct with two internal primers. In this case, the initial vector will be designed with MmeI at one flank and EcoP15I on the other; using two consecutive restriction, cloning and circularization steps, the final construct will consist of four alternative priming sites (two on the insert flanks and two internal), which in the case of 100 bp segments of genomic DNA will guarantee their complete sequencing with 25-30 cycles of SBS and three primer resets. The extra cycles would enable some of the sequence reads to run into the next primer, which would help to confirm the direction (e.g., the last sequence might end with the MmeI or EcoP15I site. Other tricks would include modifying the ends of the primers to allow looping and reverse direction sequencing, incorporation of one or two decoding bases in the internal primers to confirm directions, and deconvoluting the results after all the data is generated. One would want to have a single set of primers for sequencing, regardless of which strand is attached. In order to achieve this, and to overcome the non-directional nature of their insertion, the internal primer or primers will be designed as palindromes so that sequencing can be initiated in either direction.

Materials and Methods

Figure 15:
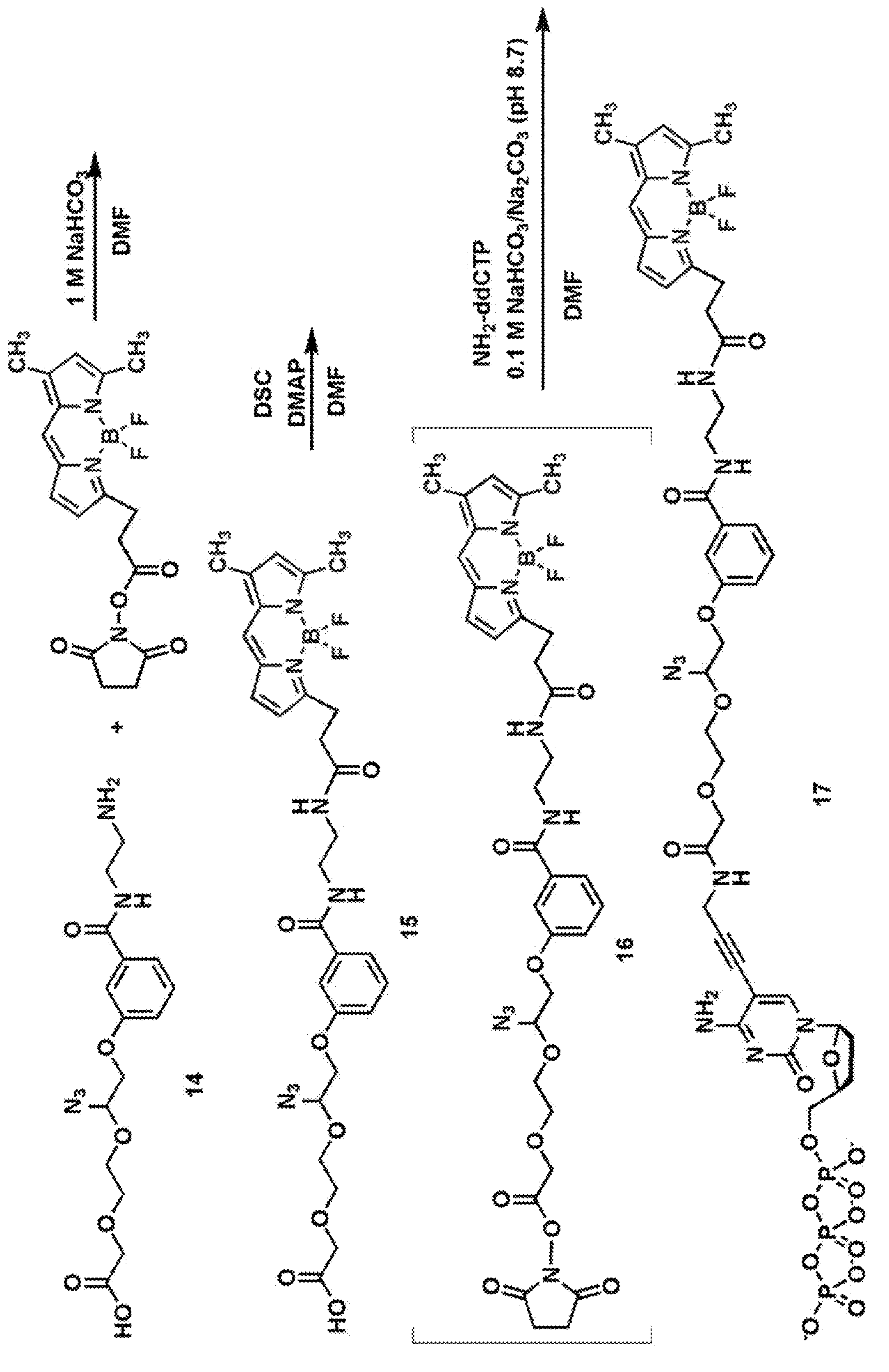
FIG. 15. Synthesis of ddCTP-$N_3$-Bodipy-FL-510

Synthesis of ddCTP-$N_3$-Bodipy-FL-510 a. Azido-Bodipy-FL-510 (FIG. 15, Compound 15). (2-{2-[3-(2-Amino-ethylcarbamoyl)-phenoxy]-1-azido-ethoxy}-ethoxy)-acetic acid 14 (7.0 mg, 0.019 mmol) prepared according to the literature[1] was dissolved in DMF (300 μl) and 1 M $NaHCO_3$ aqueous solution (100 μl). A solution of Bodipy-FL-510 NHS (N-hydroxysuccinimide) ester (Invitrogen) (5.0 mg, 0.013 mmol) in DMF (400 μl) was added slowly to the above reaction mixture and then stirred at room temperature for 5 hours with exclusion of light. The crude product was purified on a preparative silica gel TLC plate ($CHCl_3/CH_3OH$, 1:4) to afford 15 (7.6 mg; 91%). $^1H$ NMR (400 MHz, $CD_3OD$) δ7.34-7.42 (m, 4H), 710-7.14 (m, 1H), 6.90 (d, J=4.0 Hz, 1H), 6.29 (d, J=4.0 Hz, 1H), 6.20 (s, 1H), 5.00 (t, J=5.2 Hz, 1H), 4.22-4.25 (m, 1H), 4.10-4.14 (m, 1H), 3.96-4.01 (m, 2H), 3.91 (s, 2H), 3.83-3.88 (m, 1H), 3.70-3.71 (m, 2H), 3.43-3.48 (m, 3H), 3.20-3.24 (m, 2H), 2.61-2.65 (m, 2H), 2.57 (s, 3H), 2.49 (s, 3H); MS (Fab+) calcd for $C_{29}H_{34}BF_2N_7O_7$ [$(M+H)^+$]: 642.4, found: 642.5.

b. ddCTP-$N_3$-Bodipy-FL-510 (FIG. 15, Compound 17). To a stirred solution of 15 in dry DMF (2 ml), DSC (N, N'-disuccinimidyl carbonate) (3.4 mg, 13.2 μmol) and DMAP (4-dimethylaminopyridine) (1.6 mg, 13.2 μmol) were added. The reaction mixture was stirred at room temperature for 2 hours. TLC indicated that 15 was completely converted to compound 16, which was directly used to couple with amino-ddCTP (13 μmol) in $NaHCO_3$/$Na_2CO_3$ buffer (pH=8.7, 0.1 M) (300 μl). The reaction mixture was stirred at room temperature for 3 hours with exclusion of light. The reaction mixture was purified by a preparative silica gel TLC plate ($CH_3OH/CH_2Cl_2$, 1:1). The crude product was further purified on reverse-phase HPLC to afford 17 (retention time=34.0 min). Compound 17 was further evaluated by performing a single base extension reaction to yield a DNA extension product which was characterized by MALDI-TOF MS (m/z 8915) (FIG. 20C).

Figure 16:
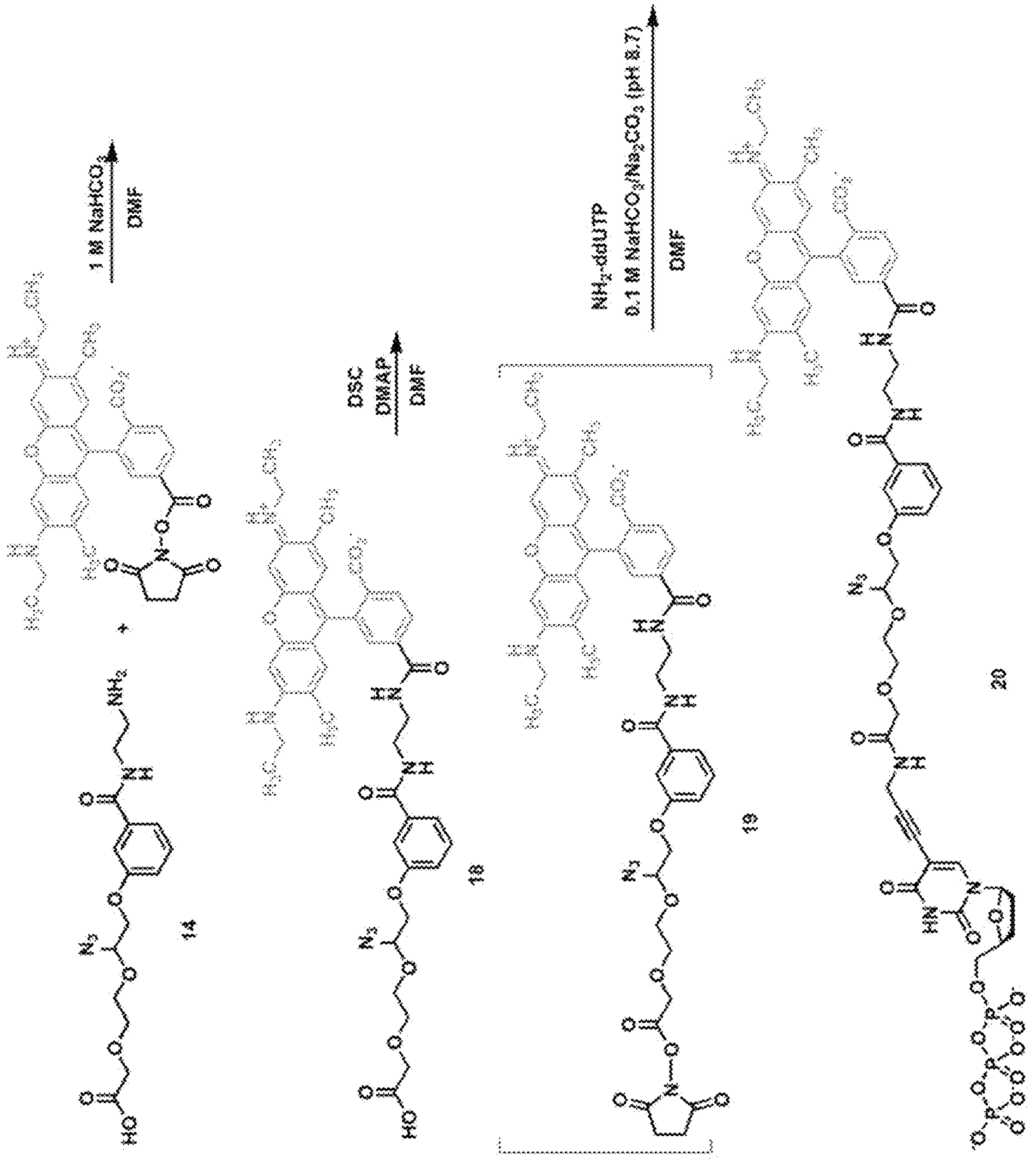
FIG. 16. Synthesis of ddUTP-$N_3$-R6G

Synthesis of ddUTP-$N_3$-R6G a. Azido-R6G (FIG. 16, Compound 18). The preparation procedure was similar to the synthesis of 15. The crude product was purified by a preparative silica gel TLC plate ($CH_3OH/CH_2Cl_2$, 2:5) to afford 18 (8.2 mg; 89%). 1H NMR (400 MHz, $CD_3OD$) δ 8.12-8.08 (m, 2H), 7.68 (d, J=1.6 Hz, 1H), 7.49-7.45 (m, 1H), 7.38-7.36 (m, 2H), 7.32-7.30 (m, 1H), 7.26-7.22 (m, 1H), 7.14-7.12 (m, 1H), 7.06-7.05 (m, 1H), 6.96 (s, 2H), 6.87 (s, 3H), 5.05 (t, J=5.0 Hz, 1H), 4.15-4.14 (m, 1H), 4.04-4.03 (m, 1H), 3.94-3.92 (m, 2H), 3.86-3.80 (m, 3H), 3.67-3.62 (m, 6H), 3.51 (q, J=7.2 Hz, 4H), 2.08 (s, 6H), 1.36 (t, J=7.2 Hz, 6H); HRMS (Fab+) calcd for $C_{42}H_{46}N_7O_{10}$ [$(M+H)^+$]: 808.3306, found 808.3267.

b. ddUTP-$N_3$-R6G (FIG. 16, Compound 20). The preparation procedure was similar to the synthesis of 17. The crude product was purified on reverse-phase HPLC to afford 20 (retention time=32.9 min). Compound 20 was further evaluated by performing a single base extension reaction to yield a DNA extension product which was characterized by MALDI-TOF MS (m/z 9082) (FIG. 20G).

Figure 17:
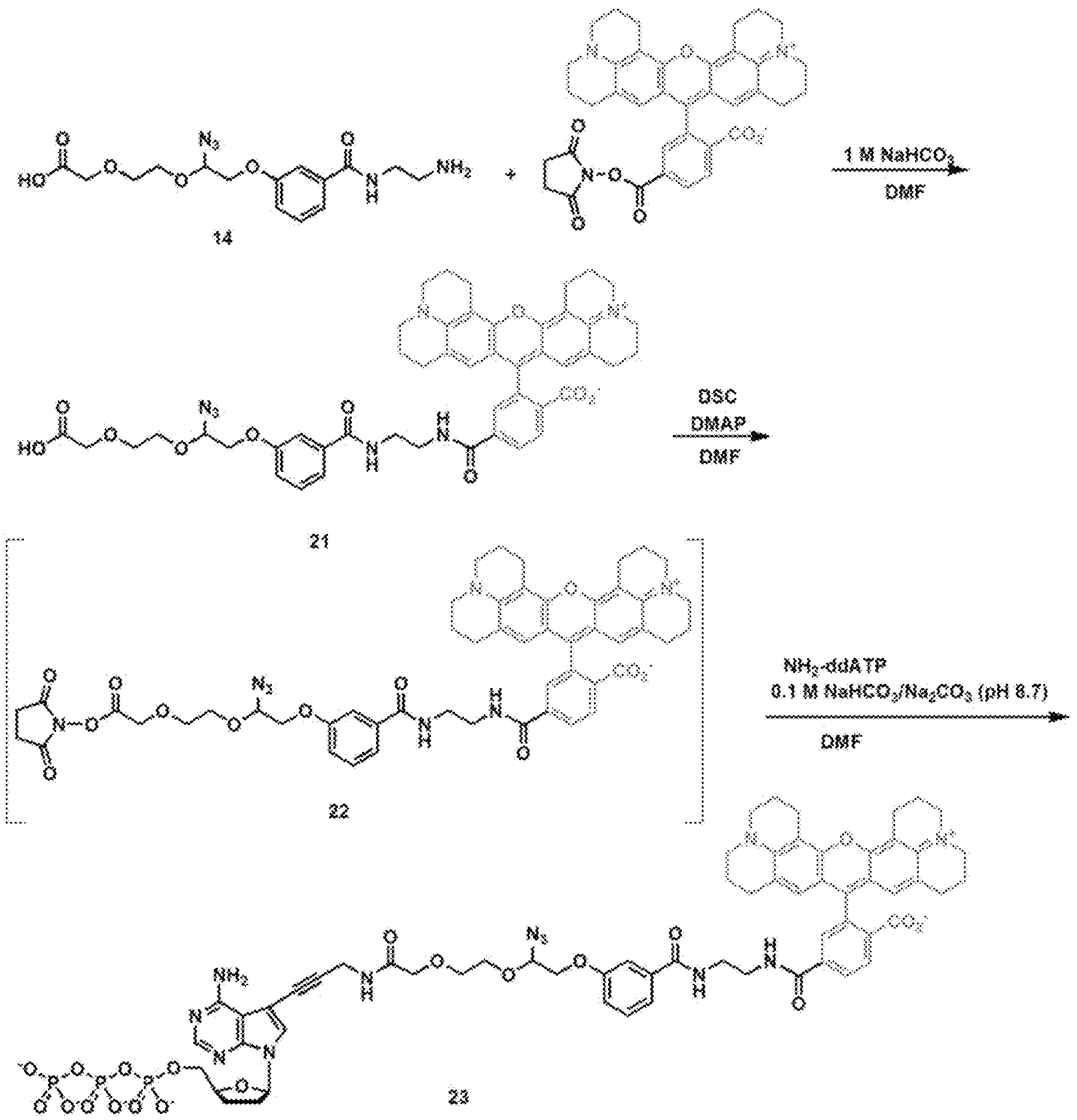
FIG. 17. Synthesis of ddATP-$N_3$—ROX

Synthesis of ddATP-$N_3$—ROX a. Azido-ROX (FIG. 17, Compound 21). The preparation procedure was similar to the synthesis of 15. The crude product was purified by a preparative silica gel TLC plate ($CH_3OH/CH_2Cl_2$, 2:5) to afford 21 (6.3 mg; 90%). $^1H$ NMR (400 MHz, $CD_3OD$) δ 8.24 (d, J=3.2 Hz, 2H), 7.65 (s, 1H), 7.49-7.46 (m, 1H), 7.38-7.35 (m, 1H), 7.32-7.30 (m, 1H), 7.26-7.23 (m, 1H), 7.14-7.12 (m, 1H), 7.05-7.04 (m, 1H), 6.70 (s, 2H), 6.87 (s, 3H), 5.02 (t, J=4.0 Hz, 1H), 4.26-4.23 (m, 1H), 4.16-4.12 (m, 2H), 4.00-3.97 (m, 2H), 3.90-3.71 (m, 3H), 3.67-3.45 (m, 8H), 3.04-3.01 (m, 4H), 2.66-2.56 (m, 4H), 2.09-2.08 (m, 4H), 1.90-1.89 (m, 4H); HRMS (Fab+) calcd for $C_{48}H_{50}N_7O_{10}$ [$(M+H)^+$]: 884.3619, found 884.3622.

b. ddATP-azido-ROX (FIG. 17, Compound 23). The preparation procedure was similar to the synthesis of 17. The crude product was purified on reverse-phase HPLC to afford 23 (retention time=36.1 min). Compound 23 was further evaluated by performing a single base extension reaction to yield a DNA extension product which was characterized by MALDI-TOF MS (m/z 9180) (FIG. 20A).

Figure 18:
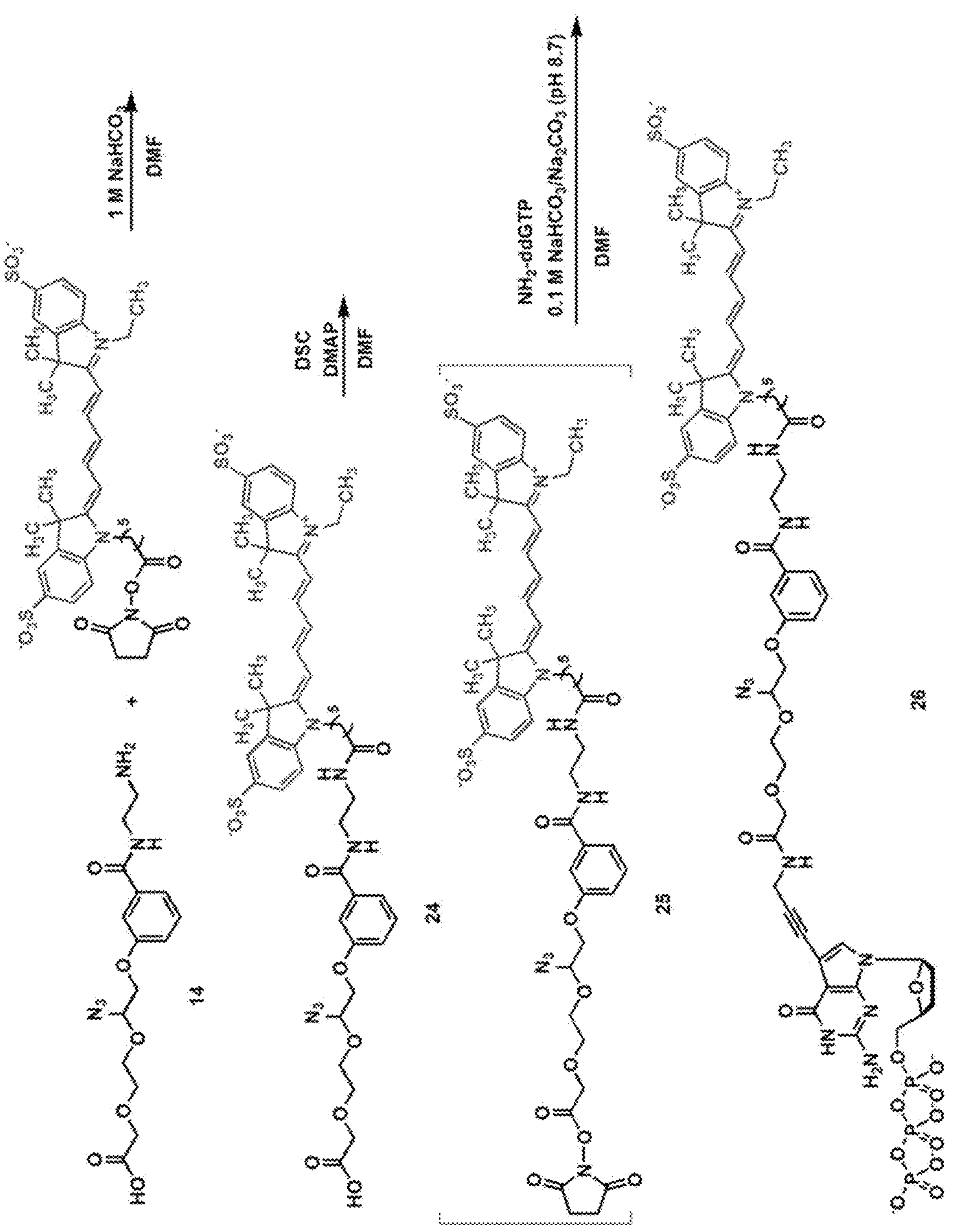
FIG. 18. Synthesis of ddGTP-$N_3$-Cy5

Synthesis of ddGTP-$N_3$-Cy5 a. Azido-Cy5 (FIG. 18, Compound 24). The preparation procedure was similar to the synthesis of 15. The crude product was purified by a preparative silica gel TLC plate ($CH_3OH/CH_2Cl_2$, 2:5) to afford 18 (5.6 mg; 84%). $^1H$ NMR (400 MHz, $CD_3OD$) δ 8.35-8.28 (m, 2H), 7.90-7.86 (m, 3H), 7.46-7.44 (m, 2H), 7.37-7.35 (m, 2H), 7.30-7.28 (d, J=8.0 Hz, 1H), 7.12-7.10 (m, 1H), 6.72 (t, J=12.4 Hz, 1H), 6.37-6.29 (m, 1H), 5.03 (t, J=4.8 Hz, 1H), 4.25-4.24 (m, 1H), 4.22-4.10 (m, 3H), 4.04-3.98 (m, 3H), 3.92 (s, 2H), 3.89-3.86 (m, 1H), 3.72-3.71 (m, 2H), 3.50-3.47 (m, 2H), 3.41-3.38 (m, 2H), 2.57 (m, 1H), 2.24-2.20 (m, 2H), 1.76 (s, 12H), 1.69-1.65 (m, 2H), 1.43-1.36 (m, 6H); MS (Fab+) calcd for $C_{48}H_{58}N_7O_{13}S_2$ [$(M+H)^+$]: 1006.4, found 1006.6.

b. ddGTP-$N_3$-Cy5 (FIG. 18, Compound 26). The preparation procedure was similar to the synthesis of 17. The crude product was purified on reverse-phase HPLC to afford 26 (retention time=31.6 min). Compound 26 was further evaluated by performing a single base extension reaction to yield a DNA extension product which was characterized by MALDI-TOF MS (m/z 9261) (FIG. 20E).

Continuous DNA Polymerase Reaction Using Four 3'-O-Modified Cleavable Nucleotides as Reversible Terminators in Solution.

The four NRTs (3'-O—$N_3$-dATP, 3'-O—$N_3$-dCTP, 3'-O—$N_3$-dGTP and 3'-O—$N_3$-dTTP) have been characterized, by performing four continuous DNA-extension reactions sequentially using a self-priming DNA template (5'-ATCGGCGCCGCGCCTTGGCGCGGCGC-3' (SEQ ID No:1). The four nucleotides in the template immediately adjacent to the annealing site of the primer are 3'-GCTA-5', which allows the evaluation of the incorporation and cleavage efficiency of the 4 NRTs. First, a polymerase extension reaction using a pool of all four NRTs along with the self-priming DNA template was performed producing a single base extension product. The reaction mixture for this, and all subsequent extension reactions, consisted of 80 pmol of self-priming DNA template, 160 pmol of 3'-O—$N_3$-dNTPs, 1× Thermopol II reaction buffer (New England Biolabs), 40 nmol of $MnCl_2$ and 1 unit of 9° N DNA polymerase (exo-) A485L/Y409V (New England Biolabs) in a total reaction volume of 20 µl. The reaction consisted of incubation at 94° C. for 5 min, 4° C. for 5 min, and 65° C. for 20 min. Subsequently, the extension product was desalted by using a ZipTip and analyzed by Voyager DE MALDI-TOF mass spectrometry (Applied Biosystems). For cleavage, the desalted DNA extension product bearing the 3'-O-azidomethyl group was first resuspended with 5 µl of 50 mM EDTA solution to quench the polymerase activity. This DNA solution was then mixed with 10 µl of 225 mM TCEP solution (pH 9.0) and incubated at 65° C. for 15 min to yield a cleaved DNA product which was characterized by MALDI-TOF MS. The DNA product with the 3'-O-azidomethyl group removed to generate a free 3'-OH group was purified by using an Oligonucleotide Purification Cartridge (Applied Biosystems) and used as a primer for a second extension reaction using 3'-O—$N_3$-dNTPs. The second extended DNA product was then purified by ZipTip and cleaved as described above. The third and the fourth extensions were carried out in a similar manner by using the previously extended and cleaved product as the primer.

Polymerase Extension Reaction Using Cleavable Fluorescent Dideoxynucleotide Terminators in Solution and Characterization by MALDI-TOF MS.

The four cleavable fluorescent dideoxynucleotide terminators, ddNTP-$N_3$-fluorophores (ddCTP-$N_3$-Bodipy-FL-510, ddUTP-$N_3$-R6G, ddATP-$N_3$—ROX, and ddGTP-$N_3$-Cy5) have been characterized, by performing four separate DNA-extension reactions, each with a different self-priming DNA template allowing the four ddNTP analogues to be incorporated. The resulting DNA extension products were analyzed by MALDI-TOF MS. The following four self-priming DNA templates (26-mer hairpin DNA with a 4-base 5'-overhang) were used for the extension: 5'-GACTGCGCCGCGCCTTGGCGCGGCGC-3' (SEQ ID No:2) for ddATP-$N_3$—ROX; 5'-ATCGGCGCCGCGCCTTGGCGCGGCGC-3' (SEQ ID No:3) for ddCTP-$N_3$-Bodipy-FL-510; 5'-GATCGCGCCGCGCCTTGGCGCGGCGC-3' (SEQ ID No:4) for ddGTP-$N_3$-Cy5; and 5'-GTCAGCGCCGCGCCTTGGCGCGGCGC~3' (SEQ ID No:5) for ddUTP-$N_3$-R6G. Each of the extension reactions consisted of all four ddNTP-$N_3$-fluorophores (e.g., 120 pmol each of ddCTP-$N_3$-Bodipy-FL-510, ddUTP-$N_3$-R6G, ddATP-$N_3$—ROX, and ddGTP-$N_3$-Cy5) along with 60 pmol of the self-priming DNA template, 1× Thermopol II reaction buffer, 40 nmol of $MnCl_2$ and 1 unit of 9°N DNA polymerase (exo-) A485L/Y4Q9V in a total reaction volume of 20 µl. The reaction consisted of incubations at 94° C. for 5 min, 4° C. for 5 min, and 65° C. for 20 min. Subsequently, the extension product was purified by reverse-phase HPLC using established procedures (40). The fraction containing the desired product was collected and freeze-dried for analysis by MALDI-TOF MS and cleavage. For cleavage of the DNA extension product bearing the ddNTP-$N_3$-fluorophores, the purified DNA product was resuspended in 50 ml of 100 mM TCEP solution (pH 9.0) at 65° C. for 15 min and then analyzed by MALDI-TOF MS.

4-Color DNA Sequencing by Synthesis on a Chip Using Photocleavable Fluorescent Dideoxynucleotide/3'-Modified Photocleavable Nucleotide Combination Remnant of Sanger Sequencing.

Ten microliters of a solution consisting of ddCTP-$N_3$-Bodipy-FL-510 (10 fmol), ddUTP-$N_3$-R6G (20 fmol), ddATP-$N_3$—ROX (40 fmol), ddGTP-$N_3$-Cy5 (20 fmol), 3'-O—$N_3$-dCTP (22 µmol), 3'-O—$N_3$-dTTP (22 µmol), 3'-O—$N_3$-dATP (22 µmol), 3'-O—$N_3$-dGTP (4 µmol), 1 unit of 9°N mutant DNA polymerase(exo-) A485L/Y409V, 20 nmol of $MnCl_2$ and 1× Thermopol II reaction buffer was spotted on the DNA chip. The nucleotide complementary to the DNA template was allowed to incorporate into the primer at 62° C. for 15 min. To synchronize any unextended templates, an extension solution consisting of 38 pmol each of 3'-O—$N_3$-dTTP, 3'-O—$N_3$-dATP, 3'-O—$N_3$-dGTP and 75 pmol of 3'-O—$N_3$-dCTP, 1 unit of 9°N mutant DNA polymerase(exo-) A485L/Y409V, 20 nmol of $MnCl_2$ and 1× Thermopol II reaction buffer was added to the same spot and incubated at 62° C. for 15 min. After washing with SPSC buffer containing 0.1% Tween 20 for 1 min, the chip was rinsed with $dH_2O$, and then scanned with a 4-color fluorescence ScanArray Express scanner (Perkin-Elmer Life Sciences) to detect the fluorescence signal. To perform the cleavage, the DNA chip was placed inside a chamber filled with 100 mM TCEP (pH 9.0) and incubated at 65° C. for 10 min. After washing the surface with $dH_2O$, the chip was scanned again to measure the background fluorescence signal. This process was followed by the next polymerase extension reaction using the 3'-O—$N_3$-dNTP/ddNTP-$N_3$-fluorophore solution with the subsequent synchronization, washing, fluorescence detection, and cleavage processes performed as described above. The 3'-O—$N_3$-dNTP/ddNTP-$N_3$-fluorophore ratio was adjusted to obtain relatively even fluorescence signals. The above reaction cycles were repeated multiple times to obtain de novo DNA sequencing data on a DNA template immobilized on a chip.

Construction of a Chip with Immobilized Self-Priming DNA Template

The 5'-amino-labeled self-priming DNA template 5'-$NH_2$-CAC-TCA-CAT-ATG-TTT-TTT-AGC-TTT-TTT-AAT-TTC-TTA-ATG-ATG-TTG-TTG-CAT-GCG-ACT-TAA-GGC-GCT-TGC-GCC-TTA-AGT-CG-3' (SEQ ID No:6) was purchased from IDT (Coralville, IA). The DNA template was dissolved at 40 µM in 50 mM sodium phosphate buffer, pH 8.5 and spotted using SpotArray 72 arraying robot (Perkin Elmer) onto high density CodeLink microarray slides (GE Healthcare). After spotting, the slides were incubated at ambient temperature (~24° C.) for 20 hours in a humid chamber containing saturated sodium chloride solution (75% humidity) to allow for 5'-tethering of the spotted amino-modified DNA templates to the slide surface functionalized with succinimide ester groups. Upon the incubation the slides were removed from the humid chamber and stored in vacuum desiccator at room temperature until further use. The principal advantage of the hairpin structure introduced into the 3'-portion of the self-priming DNA template is its higher stability and the increased priming efficiency for DNA polymerases as compared to a separate primer/template complex, which is prone to spontaneous dissociation.

3'-O—$N_3$-dNTP/ddNTP-$N_3$-Fluorophore Ratio Used for Four-Color DNA Sequencing on a Chip To obtain de novo DNA sequencing data on a DNA template immobilized on a chip, the SBS cycle was repeated multiple times using the combination mixture of solution A consisting of 3'-O—$N_3$-dCTP (3 µM), 3'-O—$N_3$-dTTP (3

μM), 3'-O—$N_3$-dATP (3 μM) and 3'-O—$N_3$-dGTP (0.5 μM) and solution B consisting of ddCTP-$N_3$-Bodipy-FL-510 (50 nM), ddUTP-$N_3$-R6G (100 nM), ddATP-$N_3$—ROX (200 nM) and ddGTP-$N_3$-Cy5 (100 nM) in each polymerase extension reaction. The following volumes of solution A and B in each SBS cycle were used to achieve relatively even fluorescence signals.

| SBS Cycle | Solution A (μl) | Solution B (μl) |
|---|---|---|
| 1st | 7.3 | 0.2 |
| 2nd | 7.3 | 0.2 |
| 3rd | 7.3 | 0.2 |
| 4th | 7.3 | 0.2 |
| 5th | 7.2 | 0.3 |
| 6th | 7.2 | 0.3 |
| 7th | 7.2 | 0.3 |
| 8th | 7.2 | 0.3 |
| 9th | 7.0 | 0.5 |
| 10th | 7.0 | 0.5 |
| 11th | 7.0 | 0.5 |
| 12th | 7.0 | 0.5 |
| 13th | 6.5 | 1.0 |
| 14th | 6.5 | 1.0 |
| 15th | 6.5 | 1.0 |
| 16th | 6.5 | 1.0 |
| 17th | 6.0 | 1.5 |
| 18th | 6.0 | 1.5 |
| 19th | 6.0 | 1.5 |
| 20th | 5.5 | 2.0 |
| 21st | 5.5 | 2.0 |
| 22nd | 5.5 | 2.0 |
| 23rd | 5.0 | 2.5 |
| 24th | 5.0 | 2.5 |
| 25th | 5.0 | 2.5 |
| 26th | 4.5 | 3.0 |
| 27th | 4.0 | 3.5 |
| 28th | 3.5 | 4.0 |
| 29th | 3.0 | 4.5 |
| 30th | 2.5 | 5.0 |
| 31st | 2.0 | 5.5 |
| 32nd | 0 | 7.5 |

DISCUSSION

Four 3'-O-modified cleavable reversible terminator nucleotides (3'-O—$N_3$-dNTPs) along with four fluorescent ddNTPs have been synthesized and characterized, and used them to produce 4-color de novo DNA sequencing data on a chip by Sanger/SBS hybrid sequencing approach that has the following advantages. With the 3'-O—$N_3$-dNTPs, after cleavage of the 3'OH capping group of the DNA extension product, there are no traces of modification left on the growing DNA strand. Therefore, there are no adverse effects on the DNA polymerase for incorporation of the next complementary nucleotide. Second, the cleavable fluorescent ddNTPs and 3'-O—$N_3$-dNTPs permanent and reversible terminators, respectively, which allow the interrogation of each base in a serial manner, a key procedure enabling accurate determination of homopolymeric regions of DNA. In addition, because all of the steps of the nucleotide incorporation, fluorescence detection for sequence determination, cleavage of the fluorophore, and the 3'-O-azidomethyl group are performed on a DNA chip, there is no longer a need for electrophoretic DNA fragment separation as in the classical Sanger sequencing method.

In the four-color hybrid SBS approach, the identity of the incorporated nucleotide is determined by the unique fluorescence emission from the four fluorescent dideoxynucleotides, whereas the role of the 3'-O-modified NRTs is to further extend the DNA strand. Therefore, the ratio of the ddNTP-$N_3$-fluorophores and 3'-O—$N_3$-dNTPs during the polymerase reaction determines how much of the ddNTP-$N_3$-fluorophores incorporate and, thus, the corresponding fluorescence emission strength. With a finite amount of immobilized DNA template on a solid surface, initially the majority of the priming strands should be extended with 3'-O—$N_3$-dNTPs, whereas a relatively smaller amount should be extended with ddNTP-$N_3$-fluorophores to produce sufficient fluorescent signals that are above the fluorescence detection system's sensitivity threshold for sequence determination. As the sequencing cycle continues, the amount of the ddNTP-$N_3$-fluorophores needs to be gradually increased to maintain the fluorescence emission strength for detection.

We have experimentally determined the ratio of the 3'-O—$N_3$-dNTPs and ddNTP-$N_3$-fluorophores to yield sequencing read length of 32 bases. The signal strength at base 32 is as strong as that of the first base (FIG. 21C), indicating it should be possible to increase the read length of the hybrid SBS further by optimizing the extension conditions to reduce the background fluorescence in the later sequencing cycles. The ultimate read length of this hybrid SBS system depends on three factors: the number of starting DNA molecules on each spot of a DNA chip, the reaction efficiency, and the detection sensitivity of the system. The read length with the Sanger sequencing method commonly reaches >700 bp. The hybrid SBS approach described here may have the potential to reach this read length, especially with improvements in the sensitivity of the fluorescent detection system, where single molecules can be reliably detected.

With sequencing read length from 14 to 30 bases in the next generation DNA sequencing systems, massive parallel digital gene expression analogous to a high-throughput SAGE (41) approach has been reported reaching single copy transcript sensitivity (42), and CHIP-Seq (43-45) based on sequencing tags of ~25 bases has led to many new discoveries in genome function and regulation. It is well established that millions of different PCR template's can be generated on a solid surface through emulsion PCR or clonal amplification (45, 20). Thus, future implementation of the hybrid SBS approach on a high-density bead array platform will provide a high-throughput and accurate DNA sequencing system with wide applications in genome biology and biomedical research.

REFERENCES

1. Walter, G.; Allan, M., Nucleotide Sequence of the Lac Operator. Proceedings of the National Academy of Science 1973, 17, 3581-3584.
2. Sanger, F.; Nicklen, S.; Coulson, A. R., DNA Sequencing with Chain-terminating Inhibitors. Proceedings of the National Academy of Science 1977, 74, 5463-5467.
3. Ju, J.; Ruan, C.; Fuller, C. W.; Glazer, A. N.; Mathies, R. A., Fluorescence Energy Transer Dye-Labeled Primers for DNA Sequencing and Analysis. Proceedings of the National Academy of Science 1995, 92, 4347-4351.
4. Kan, C. W.; Doherty, E. A.; Barron, A. E., A Novel Thermogelling Matrix for Microchannel DNA Sequencing Based on Poly-N-alkooxyalkylacrylamide Copoloymers. Electrophoresis 2003, 24, 4161-4169.
5. Prober, J. M.; Trainor, G. L.; Dam, R. J.; Hobbs, F. W.; Robertson, C. W.; Zagursky, R. J.; Cocuzza, A. J.; Jensen, M. A.; Baumeister, K., A System for Rapid DNA Sequencing with Fluorescent Chain-Terminating Dideoxynucleotides. Science 1987, 238, 336-341.

6. Smith, L. M.; Sanders, J. Z.; Kaiser, R. J.; Hughes, P.; Dodd, C.; Connell, C. R.; Heiner, C.; Kent, S. B.; Hood, L. E., Fluorescence Detection in Automated DNA Sequence Analysis. Nature 1986, 321, 674-679.
7. Bai, X.; Edwards, J. R.; Ju, J., Molecular Engineering Approaches for DNA Sequencing and Analysis. Expert Review of Molecular diagnostics 2005, 5, 797-808.
8. Collins, F. S.; Green, E. D.; Guttmacher, A. E.; Guyer, M. S., A Vision for the Future of Genomics Research. Nature 2003, 422, 835-847.
9. Drmanac, S.; Kita, D.; Labat, I.; Hauser, B.; Schmidt, C.; Burczak, J. D.; Drmanac, R., Accurate Sequencing by Hybridization for DNA Diagnostics and Individual Genomics. Nature Biotechnology 1998, 16, 54-58.
10. Edwards, J. R.; Itagaki, Y.; Ju, J., DNA Sequencing Using Biotinylated Dideoxynucleotides and Mass Spectrometry. Nucleic Acids Research 2001, 29, e104-e104.
11. Fu, D. J.; Tang, K.; Braun, A.; Reuter, D.; Darnofer-Demar, B.; Little, D. P.; O'Donnell, M. J.; Cantor, C. R.; Koster, H., Sequencing Exons 5 to 8 of the p53 Gene by MALDI-TOF Mass Spectrometry. Nature Biotechnology 1998, 16, 381-384.
12. Roskey, M. T.; Juhasz, P.; Smirnov, I. P.; Takach, E. J.; Martin, S. A.; Haff, L. A., DNA Sequencing by Delayed Extraction-matrix-assisted Laser Desorption/ionization Time of Flight Mass Spectrometry. Proceedings of the National Academy of Science 1996, 93, 4724-4729.
13. Kasianowicz, J. J.; Brandin, E.; Branton, D.; Deamer, D. W., Characterization of Individual Polynucleotide Molecules Using a Membrane Channel. Proceedings of the National Academy of Science 1996, 93, 13770-13773.
14. Meller, A.; Nivon, L.; Brandin, E.; Golovchenko, J.; Branton, D., Rapid Nanopore Discrimination Between Single Polynucleotide Molecules. Proceedings of the National Academy of Science 2000, 97, 1079-1084.
15. Vercoutere, W.; Hilt, S. T.; Olsen, H.; Deamer, D.; Haussier, D.; Akeson, M., Rapid Discrimination Among Individual DNA Hairpin Molecules at Single-nucleotide Resolution Using an Ion Channel. Nature Biotechnology 2001, 17, 248-252.
16. Howorka, S.; Cheley, S.; Bayley, H., Sequence-specific Detection of Individual DNA Strands Using Engineered Nanopores. Nature Biotechnology 2001, 19, 636-639.
17. Gu, L. Q.; Braha, O.; Conlan, S.; Cheley, S.; Bayley, H., Stochastic Sensing of Organic Analytes by a Pore-forming Protein Containing a Molecular Adapter. Nature 1999, 398, 686-670.
18. Shendure, J.; Porreca, G. J.; Reppas, N. B.; Lin, X.; McCutcheon, J. P.; Rosenbaum, A. M.; Wang, M. D.; Zhang, K.; Mitra, R. D.; Church, G. M., Accurate Multiplex Polony Sequencing of an Evolved Bacterial Genome. Science 2005, 309, 1728-1732.
19. Hyman, E. D., A New Method of Sequencing DNA. Analytical Biochemistry 1988, 174, 423-436.
20. Margulies, M.; Egholm, M.; Altman, W. E.; Attiya, S.; Bader, J. S.; Bemben, L. A.; Berka, J.; Braverman, M. S.; Chen, Y. J.; Chen, Z.; et al., Genome Sequencing in Microfabricated High-density Picolitre Reactors. Nature 2005, 437, 376-380.
21. Ronaghi, M., Pyrosequencing Sheds Light on DNA Sequencing. Genome Research 2001, 11, 3-11.
22. Ju, J.; Kim, D. H.; Bi, L.; Meng, Q.; Bai, X.; Li, Z.; Li, X.; Marma, M. S.; Shi, S.; Wu, J.; Edwards, J. R.; Romu, A.; Turro, N. J., Four-color DNA Sequencing by Synthesis Using Cleavable Fluorescent Nucleotide Reversible Terminators. Proceedings of the National Academy of Science 2006, 103, 19635-19640.
23. Metzker, M. L.; Raghavachari, R.; Richards, S.; Jacutin, S. E.; Civitello, A.; Burgess, K.; Gibbs, R. A., Termination of DNA Synthesis by Novel 3'-modified-deoxyribonucleoside 5'-triphosphates. Nucleic Acids Research 1994, 22, 4259-4267.
24. Lu, G.; Burgess, K., A Diversity Oriented Synthesis of 3'-O-modified Nucleoside Triphosphates for DNA 'Sequencing by Synthesis'. Bioorganic & Medicinal Chemistry Letters 2006, 16, 3902-3905.
25. Metzker, M. L., Emerging Technologies in DNA Sequencing. Genome Research 2005, 15, 1767-1776.
26. Pelletier, H.; Sawaya, M. R.; Kumar, A.; Wilson, S. H.; Kraut, J., Structures of Ternary Complexes of Rat DNA Polymerase Beta, a DNA Template-primer, and ddCTP. Science 1994, 264, 1891-1903.
27. Rosenblum, B. B.; Lee, L. G.; Spurgeon, S. L.; Khan, S. H.; Menchen, S. M.; Heiner, C. R.; Chen, S. M., New Dye-labeled Terminators for Improved DNA Sequencing Patterns. Nucleic Acids Research 1997, 25, (4500-4504).
28. Zhu, Z.; Chao, J.; Yu, H.; Waggoner, A. S., Directly Labeled DNA Probes Using Fluorescent Nucleotides with Different Length Linkers. Nucleic Acids Research 1994, 22, 3418-3422.
29. Seo, T. S.; Bai, X.; Kim, D. H.; Meng, Q.; Shi, S.; Ruparel, H.; Li, Z.; Turro, N. J.; Ju, J., Four-color DNA Sequencing by Synthesis on a Chip Using Photocleavable Fluorescent Nucleotides. Proceedings of the National Academy of Science 2005, 102, (5926-5931).
30. Kolb, H. C.; Finn, M. G.; Sharpless, K. B., Click Chemistry: Diverse Chemical Function from a Few Good Reactions. Angewandte Chemie International Edition 2001, 40, 2004-2021.
31. Seo, T. S.; Li, Z.; Ruparel, H.; Ju, J., Click Chemistry to Construct Fluorescent Oligonucleotides for DNA Sequencing. Journal of Organic Chemistry 2003, 68, 609-612.
32. Bi, L.; Kim, D. H.; Ju, J., Design and Synthesis of a Chemically Cleavable Fluorescent Nucleotide, 3'-O-Allyl-dGTP-allyl-Bodipy-FL-510, as a Reversible Terminator for DNA Sequencing by Synthesis. Journal of American Chemical Society 2006, 128, (2542-2543).
33. Pillai, V. N. R., Photoremovable Protecting Groups in Organic Synthesis. Synthesis 1980, 1, 1-26.
34. Meng, Q.; Kim, D. H.; Bai, X.; Bi, L.; Turro, N. J.; Ju, J., Design and Synthesis of a Photocleavable Fluorescent Nucleotide 3'-O-Allyl-dGTP—PC-Bodipy-FL-510 as a Reversible Terminator for DNA Sequencing by Synthesis. Journal of Organic Chemistry 2006, 71, 3248-3252.
35. Gololobov, Y. G.; Zhmurova, I. N.; Kasukin, L. F., Sixty Years of Staudinger Reaction. Tetrahedron 1981, 37, 437-472.
36. Saxon E, Bertozzi C R (2000) Science 287:2007-2010.
37. Milton J, Ruediger S, Liu X (2006) United States Patent Application US20060160081A1.
38. Barnes, C., Balasubramanian, S., Liu, X., Swerdlow, H., Milton, J. (2006) U.S. Pat. No. 7,057,026.
39. Wu, W., et al. (2007) Nucleic Acid Research 35:6339-6349
40. Zavgorodny S, et al. (2000) Nucleosides, Nucleotides Nucleic Acids 19:1977-1991.
41. Velculescu V E, Zhang L, Vogelstein B, Kinzler K W (1995) Science 270:484-487.
42. Kim J B, Porreca G J, Song L, Greenway S C, Gorham J M, Church G M, Seidman C E, Seidman J G (2007) Science 316:1481-1484.
43. Mikkelsen T S, Ku M, Jaffe D B, Issac B, Lieberman E, Giannoukos G, Alvarez P, Brockman W, Kim T K, Koche R P, et al. (2007) Nature 448:553-560.

44. Johnson D S, Mortazavi A, Myers R M, Wold B (2007) Science 316: 1497-1502.
45. Barski A, Cuddapah S, Cui K, Roh T Y, Schones D E, Wang Z, Wei G, Chepelev I, Zhao K (2007) Cell 129: 823-837.

What is claimed is:

1. A method for sequencing a DNA template of at least 24 nucleotides comprising detecting the identities of deoxyribonucleotide analogues of adenine, guanine, cytosine, and thymine incorporated into the end of a growing strand of complementary DNA synthesized using a DNA polymerase in a DNA polymerase reaction, wherein the deoxyribonucleotide analogues act as reversible terminators in the DNA polymerase reaction and wherein the reversible terminators comprise labeled and unlabeled deoxyribonucleotide analogues, a) wherein at least a first labeled deoxyribonucleotide analogue is derived from the group consisting of labeled deoxyribonucleotide analogues A-D:

(A)

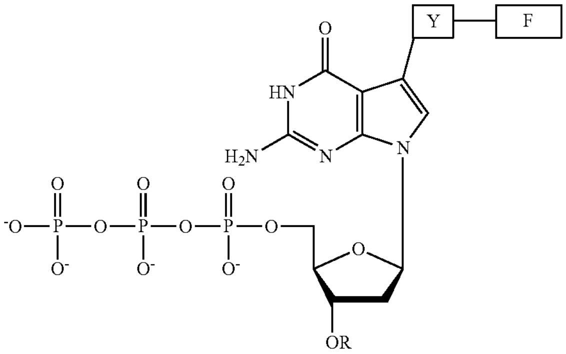

;

(B)

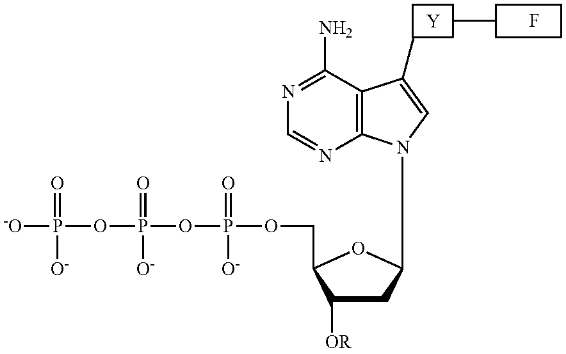

;

(C)

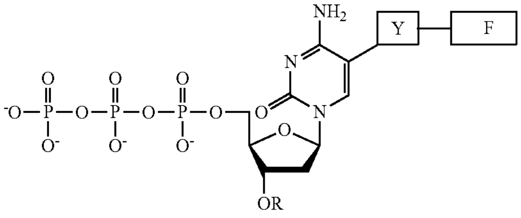

; and (D)

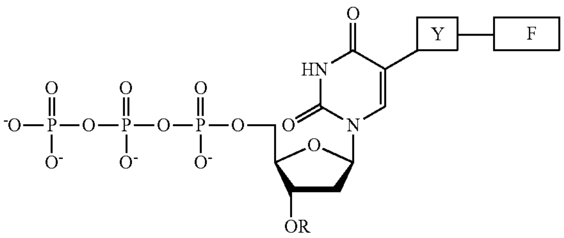

;

b) wherein at least a second labeled deoxyribonucleotide analogue is derived from the group consisting of labeled deoxyribonucleotide analogues A-D, wherein the second labeled deoxyribonucleotide analogue in b) is different from the first labeled deoxyribonucleotide analogue in a); and c) wherein at least a third unlabeled deoxyribonucleotide analogue is derived from the group consisting of unlabeled deoxyribonucleotide analogues A'-D':

(A')

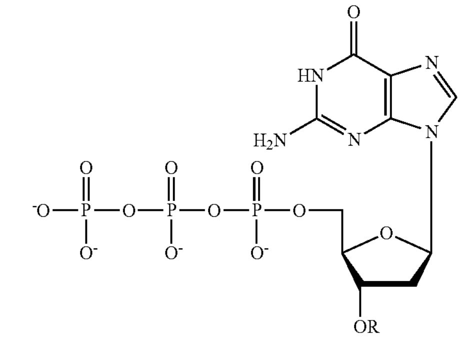

;

(B')

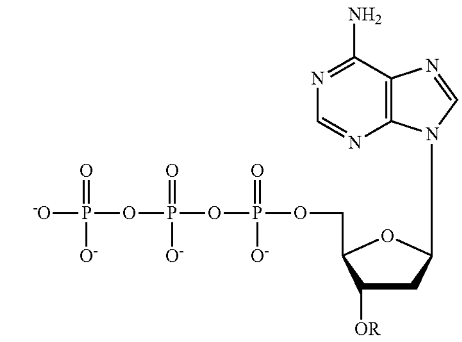

;

(C')

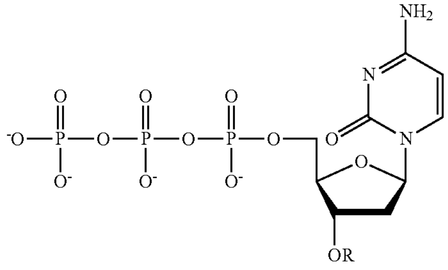

; and (D')

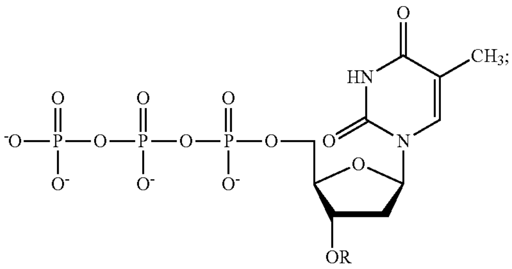

wherein R (a) represents a cleavable, chemical group capping the oxygen at the 3' position of the deoxyribose of the deoxyribonucleotide analogue, (b) does not interfere with recognition of the deoxyribonucleotide analogue as a substrate by the DNA polymerase or with incorporation of the deoxyribonucleotide analogue into the growing DNA strand during the DNA polymerase reaction, and (c) is stable during the DNA polymerase reaction;

wherein the covalent bond between the 3'-oxygen and R is stable during the DNA polymerase reaction;

wherein the F on each of the deoxyribonucleotide analogues represents a distinguishable, detectable moiety;

wherein L represents a cleavable, chemical linker which (a) does not interfere with recognition of the deoxyribonucleotide analogue as a substrate by the DNA polymerase or with incorporation of the deoxyribonucleotide analogue into the growing DNA strand during the DNA polymerase reaction and (b) is stable during the DNA polymerase reaction;

wherein (i) the deoxyribonucleotide analogue is incorporated into the growing DNA strand as a result of the DNA polymerase reaction, (ii) the incorporated deoxyribonucleotide analogue is identified, and (iii) the cleavable chemical linker L, and the covalent bond between the 3'-oxygen and R are cleaved under conditions compatible with DNA sequencing to allow the incorporation and detection of the next deoxyribonucleotide analogue;

wherein the deoxyribonucleotide analogue:

i) is recognized as a substrate by the DNA polymerase for incorporation into the growing DNA strand during the DNA polymerase reaction, ii) is efficiently and accurately incorporated at the end of the growing DNA strand during the DNA polymerase reaction, iii) produces a 3'—OH group on the deoxyribose upon cleavage of R under conditions compatible with DNA sequencing, and iv) no longer includes the detectable moiety on the base upon cleavage of L under conditions compatible with DNA sequencing; and wherein if the deoxyribonucleotide analogue is:

(A) or (A'), it forms hydrogen bonds with cytosine or a cytosine deoxyribonucleotide analogue;

(B) or (B'), it forms hydrogen bonds with thymine or a thymine deoxyribonucleotide analogue;

(C) or (C'), it forms hydrogen bonds with guanine or a guanine deoxyribonucleotide analogue; or (D) or (D'), it forms hydrogen bonds with adenine or an adenine deoxyribonucleotide analogue.

2. The method of claim 1, further comprising incorporating a labeled or unlabeled deoxyribonucleotide analogue selected from the group consisting of labeled deoxyribonucleotide analogues A-D or from the group consisting of unlabeled deoxyribonucleotide analogues A'-D', wherein the labeled or unlabeled deoxyribonucleotide analogue is incorporated into the growing DNA strand that has been continuously extended by at least 24 continuous bases as a result of the DNA polymerase reaction.

3. A method for simultaneously sequencing a plurality of different deoxyribonucleic acid templates comprising simultaneously applying the method of claim 1 to the plurality of different deoxyribonucleic acid templates.

4. The method of claim 1, wherein the first labeled deoxyribonucleotide analogue is derived from 3'-O-Azido-dNTPs-Azido-Bodipy-FL-510.

5. The method of claim 1, wherein the second labeled deoxyribonucleotide analogue is derived from 3'-O-Azido-dNTPs-Azido-R6G.

6. The method of claim 1, wherein the third unlabeled deoxyribonucleotide analogue is derived from 3'-O-Azido-dGTP.

* * * * *